(12) United States Patent
Wang et al.

(10) Patent No.: US 6,900,218 B2
(45) Date of Patent: May 31, 2005

(54) PYRUVATE DERIVATIVES

(75) Inventors: Bing Wang, Cupertino, CA (US); Guy Miller, San Jose, CA (US); Satyanarayana Janagani, Santa Clara, CA (US)

(73) Assignee: Galileo Pharmaceuticals, Inc., Santa Clara, CA (US)

( * ) Notice: Subject to any disclaimer, the term of this patent is extended or adjusted under 35 U.S.C. 154(b) by 0 days.

(21) Appl. No.: 10/138,938

(22) Filed: May 3, 2002

(65) Prior Publication Data

US 2003/0013657 A1 Jan. 16, 2003

Related U.S. Application Data

(60) Provisional application No. 60/288,649, filed on May 3, 2001, provisional application No. 60/295,314, filed on Jun. 1, 2001, and provisional application No. 60/368,456, filed on Mar. 27, 2002.

(51) Int. Cl.$^7$ .................. C07D 235/12; C07D 239/74; C07D 277/60; A61K 31/428; A61K 31/517
(52) U.S. Cl. .................. 514/266.1; 514/359; 514/367; 514/394; 544/283; 544/106; 548/121; 548/146; 548/180; 548/310.1; 548/165; 548/182; 548/316.4
(58) Field of Search .................. 564/162, 163, 564/194; 562/440; 560/17, 168; 548/165, 182, 301.4, 180, 121, 146, 310.1, 316.4; 54/316.4; 544/283, 106; 514/266.1, 359, 367, 394

(56) References Cited

U.S. PATENT DOCUMENTS

| | | | | |
|---|---|---|---|---|
| 4,137,320 A | * | 1/1979 | Tedeschi | 514/368 |
| 4,762,848 A | * | 8/1988 | Scheunemann et al. | 514/369 |
| 4,914,206 A | * | 4/1990 | Minamida et al. | 544/376 |
| 5,141,946 A | * | 8/1992 | Katano et al. | 514/302 |
| 5,189,158 A | * | 2/1993 | Feigelson et al. | 540/302 |
| 5,719,147 A | | 2/1998 | Dorn et al. | |
| 5,866,604 A | | 2/1999 | Pellacini et al. | |
| 6,057,312 A | | 5/2000 | Cho et al. | |
| 6,348,617 B1 | | 2/2002 | Ushio et al. | |

FOREIGN PATENT DOCUMENTS

| | | |
|---|---|---|
| EP | 288789 A1 | 11/1988 |
| EP | 795554 A2 * | 9/1997 |
| GB | 2 076 803 A | 12/1981 |
| WO | WO2001002373 A1 * | 1/2001 |
| WO | WO 01/25210 * | 4/2001 |
| WO | WO 01/40206 A1 | 6/2001 |
| WO | WO 02/074301 A1 | 9/2002 |

OTHER PUBLICATIONS

Labrou Journal of Protein Chemistry 18(7): 729–733, 1999.*
Capozzi et al., Tetrahedron Letters 38(28): 5041–5044, 1997.*
Sayed et al., Egyptian Journal Of Pharmaceutical Sciences 37(1–6): 295–302,1996.*
Labrou et al., Journal of Chromatography A 718(11): 35–44, 1995.*
Shahripour et al., Journal of Medicinal Chemistry 38(15): 2893–2905.*
Abdel–Rahman al., Pakistan Journal of Scientific and Industrial Research 35(3): 69–72, 1992.*
Lattrell et al., Justus Liebigs Annalen der Chemie 6: 921–922, 1974.*
Alper et al., Journal of Organic Chemistry 38(21) 3742–3744, 1973.*
Alper et al., Journal of Organic Chemistry 36910) 1352–1355, 1971.*
Haskell et al., Journal of Medicinal Chemistry 13(4): 697–704, 1970.*
Westphal, G. et al. (1976) "Reactions with Pyridinium Pyruvates" *Pharamazie* 31(11):770–773. (abstract).
Iwamatsu, K. et al. (1983). "Synthesis and Biological Activity of 7,8–(2–Amino–2–Carboxy)– Ethylthioacetamido–7alpha–Methoxycephalosporin Derivatives" *Journal of Antibiotics*. 36(3):229–241.
Bedeschi, A. et al. (1982). "Synthesis and In Vitro Activity of Some 7–[2–Metholyimino–(Substitiuted Thio)Alkanoyl] Amino Cephalosporanic Acid Derivatives" *Journal of Antibiotics*. 35(6):712–720.
Cavero, M. et al. (2001). "Studies on the intermolecular free radical addition of thionitrites to alkenes: a convenient method of the preparation of alpha–tritylthio oximes and related derivatives" *Tetrahedron Letters* 42:4377–4379.
Gilchrist, T.L. et al. (1987). "Reaction of Azoles with Ethyl Bromoopyruvate Oxime: Alkylation by Substitution and by Elimination–Addition" *J. Chem. Soc. Perkin Trans.* 1(10):2235–2240.
Gilchrist, T. et al. (1979). "Ethyl 3–Bromo–2–hydroxyimino propanoate, a Reagent for the Preparation of Ethyl Esters of alpha–Amino Acids" *Journal of the Chemical Society, Chem. Comm.* 1089–1090.

(Continued)

Primary Examiner—Venkataraman Balasubramanian
(74) Attorney, Agent, or Firm—Foley & Lardner LLP

(57) ABSTRACT

Certain known and novel pyruvate derivatives are particularly active in restoring or preserving metabolic integrity in oxidatively competent cells that have been subjected to oxygen deprivation. These pyruvate-derived compounds include, but are not limited to oximes, amides, pyruvate analogues, modified pyruvate analogues, esters of pyruvate (e.g., polyol-pyruvate esters, pyruvate thioesters, glycerol-pyruvate esters and dihydroxyacetone-pyruvate esters). Such pyruvate derivatives (including single tautomers, single stereoisomers and mixtures of tautomers and/or stereoisomers, and the pharmaceutically acceptable salts thereof) are useful in the manufacture of pharmaceutical compositions for treating a number of conditions characterized by oxidative stress.

4 Claims, No Drawings

OTHER PUBLICATIONS

Sidky, M.M. et al. (1972) "Mannich Bases of Glyoxylanilide 2–Oximes and their Effect on Photosyntetic Electron Transport" *Z. Naturforssch.* 27b:797–799.

Andreichikov, Y.S. et al. (1977). " Chemistry of oxalyl derivatives of methyl ketones. XVII. Synthesis and biological activity of the esters of arlylsulfonylpyruvic acids and their derivatives" *Khimiko–Farmatsevticheskii Zhurnal* 11(10):85–89. (abstract).

Fridman, A.L. et al. (1977). "Reactions of aliphatic diazo compounds. XXX. Synthesis of 2–diazo–3–(arylsulfonlyl) propanoate" *Zh. Organic Khim.* 13 (8):1589–1593. (abstract).

Andreichikov, Y.S. et al. (1977). "Chemistry of oxalyl derivatives of methyl ketones. VIII. Synthesis and properties of arylsulfonylpyroracemic acid esters" *Zh. Organic Khim.* 13(10):2070–2074. (abstract).

Harash et al. (1973). *J.Prakt. Chemincal.* 315:235–242 (abstract).

Eistert, B. et al. (1963) *Justus Liebigs Ann. Chemical.* 666:97–112.

Rossi, S. et al. (1962). *Gazz. Chim. Ital.* 92:1367–1378.

* cited by examiner

PYRUVATE DERIVATIVES

CROSS-REFERENCE TO RELATED APPLICATIONS

This application claims the benefit on the following provisional applications: U.S. Ser. No. 60/288,649, filed May 3, 2001; U.S. Ser. No. 60/295,314, filed Jun. 1, 2001; and U.S. Ser. No. 60/368,456, filed Mar. 27, 2002, each incorporated herein by reference in its entirety. This application is also related to application U.S. Ser. No. 10/138,032, (now U.S. Pat. No. 6,608,196); Ser. Nos. 10/138,726; 10/138,809 (now abandoned) and Ser. No. 10/138,937, each incorporated herein by reference in its entirety.

FIELD OF THE INVENTION

The present invention relates to pyruvate derivatives, particularly to derivatives having cytoprotective activity, and specifically to a series of aromatic and peptidyl pyruvates. The invention is also directed to formulations and methods for treating stroke, myocardial infarction and chronic heart failure, as well as other oxidative stress and/or inflammation related conditions that are typically responsive to cellular enzyme modulation.

BACKGROUND INFORMATION

Pyruvate is a three-carbon (triose) ketoacid that is produced in biological systems in the end stages of glycolysis, a product of sugar metabolism. It is also a breakdown product of certain amino acids (alanine, glycine, cysteine, serine). Pyruvate can be reduced to lactate in the cytoplasm, a fermentative event in mammalian cells, or oxidatively decarboxylated to acetyl CoA in the mitochondrion.

There are known in the art a number of pyruvate derivatives. It has been suggested that pyruvate and certain pyruvate derivatives may have utility in treating certain disorders and promoting health. For example, pyruvate is sold as a dietary supplement for use in promoting weight loss and enhancing energy. It has also been suggested as a therapeutic intervention for clinical management of myocardial insufficiency (Mallet, R. T., 2000, Proc. Soc. Exp. Biol. Med. 223(2): 136–148) and to prevent the adverse effects of myocardial ischemia (U.S. Pat. No. 5,294,641). U.S. Pat. Nos. 5,075,210 and 4,988,245 describe the use of pyruvate or pyruvate salts as a component in a cardioplegic solution and in preservation solutions (perfusion fluids) for heart allografts before transplantation. U.S. Pat. No. 5,395,822 describes the use of certain pyruvate salts to protect against neuronal degeneration as a consequence of ischemia.

U.S. Pat. No. 6,086,789 describes certain pyruvate derivatives as useful for dermatologic indications as well as for treating diabetic ketosis, myocardial ischemia, injured organs and hypercholesterolemia. Specifically, it ascribes these activities to various esters of pyruvate, including polyol-pyruvate esters, pyruvate thioesters, glycerol-pyruvate esters, and dihydroxyacetone-pyruvate ester. Related U.S. Pat. No. 5,968,727 describes the use of pyruvate thiolesters, such as cysteine, methionine and homocysteine, and glycerol pyruvate esters and dihydroxyacetone-pyruvate esters, in organ preservation solutions and for treating ischemia. Similarly, certain pyruvate and pyruvyl amino acid conjugates have been suggested for use in diabetes (e.g., U.S. Pat. Nos. 5,047,427 and 5,256,697).

It has, however, remained desired to provide new therapies for conditions characterized by oxidative stress, and particularly, for providing neuroprotection in the event of cerebral ischemia; especially desired are agents that are effective even if first administered after a significant period of time (e.g., about 5 or more hours) following an ischemic insult.

SUMMARY OF THE INVENTION

The present invention is concerned with certain known and novel pyruvate derivatives that are particularly active in restoring or preserving metabolic integrity in oxidatively competent cells that have been subjected to oxygen deprivation. These pyruvate-derived compounds include, e.g., but are not limited to oximes, amides, pyruvate analogues, modified pyruvate analogues, esters of pyruvate (e.g., polyol-pyruvate esters, pyruvate thioesters, glycerol-pyruvate esters and dihydroxyacetone-pyruvate esters). Such pyruvate derivatives are useful in the manufacture of pharmaceutical compositions for treating a number of conditions characterized by oxidative stress, and particularly, in providing neuroprotection in the event of cerebral ischemia, even when administered a significant time interval after an ischemic insult. In particular, the compositions of the present invention are useful in the treatment of stroke, as demonstrated by providing neuroprotection in a standard experimental model of focal cerebral ischemia. They are also useful in the treatment of myocardial ischemia (myocardial infarction), as well as other indications characterized by oxidative stress and/or inflammation, including, but not limited to, neurodegenerative disorders such as Alzheimer's, dementia, and Parkinson's disease; diabetes; renal disease; pre-menstrual syndrome; asthma, cardiopulmonary inflammatory disorders; chronic heart failure; rheumatoid arthritis; muscle fatigue; intermittent claudication; and for the preservation of allograft tissue for transplantation.

One aspect of the present invention concerns methods of treatment and the manufacture of medicaments therefor, employing the compounds represented by Formula I:

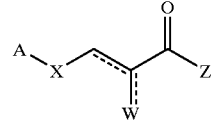

Formula I wherein:
  the dashed line is a double bond one of the indicated positions and a single bond in the other, or (where W is —N(OH)—C(O)—$R^d$) is a single bond in both positions;
  A is: optionally substituted alkyl, optionally substituted cycloalkyl, optionally substituted aryl, optionally substituted aralkyl, optionally substituted heteroaryl, optionally substituted heteroaralkyl, optionally substituted heterocyclyl, optionally substituted heterocycloalkyl, an optionally substituted nucleoside, an optionally substituted amino acid, an optionally substituted di-, tri- or tetra-peptide, —$CH_2$—C(O)—C(O)—O—R' or —CH=C(OH)—C(O)—O—R';
  X is: —N(R')—, —S—, —S(O)—, —$S(O)_2$—, —S—Y—S—, or a covalent bond to the sulfur atom of Cys or to the nitrogen atom of optionally substituted heterocyclyl;
  Y is: optionally substituted aryl, optionally substituted heteroaryl, an optionally substituted nucleoside, an optionally substituted amino acid, or an optionally substituted di-, tri- or tetra-peptide;

W is: =O, =N—OR$^a$, =N—NR$^b$R$^c$, or —N(OH)—R$^d$;

Z is: —OR, —SR, or —NR$^b$R$^c$;

R' is: independently selected from hydrogen, optionally substituted alkyl, optionally substituted cycloalkyl or optionally substituted aryl;

R is: hydrogen, optionally substituted alkyl, optionally substituted cycloalkyl, optionally substituted aryl, optionally substituted aralkyl, optionally substituted heteroaryl, optionally substituted heteroaralkyl, optionally substituted heterocyclyl or optionally substituted heterocycloalkyl;

R$^a$ is: hydrogen, optionally substituted alkyl, optionally substituted aryl, optionally substituted aralkyl, or alkenyl;

R$^b$ is: independently selected from hydrogen, optionally substituted alkyl, optionally substituted aryl, optionally substituted aralkyl or optionally substituted cycloalkyl;

R$^c$ is: independently selected from hydrogen or optionally substituted alkyl; and R$^d$ is: hydrogen, acyl or optionally substituted alkyl; or R$^b$ and R$^c$ together with the nitrogen to which they are attached may form a 5- to 7-membered ring, optionally incorporating one or two additional ring heteroatoms chosen from N, S, or O, and said ring being optionally substituted with one or more substituents independently selected from the group consisting of =O, =S, acyl, optionally substituted alkenyl, optionally substituted alkyl, (optionally substituted alkoxy)carbonyl, and (optionally substituted amino) carbonyl;

including single tautomers, single stereoisomers and mixtures of tautomers and/or stereoisomers, and the pharmaceutically acceptable salts thereof, provided that where X is —S—, W is =O, and Z is OH, A is not 6-amino-3,5-dicyano-4-(optionally substituted phenyl)-pyridin-2-yl.

Another aspect of the present invention concerns the compounds represented by Formula Ia:

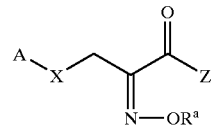

Formula Ia where:

A is: substituted alkyl selected from: —CH$_2$—CH(OH)—CH$_2$—OH, —CH(CH$_3$)—CH(OH)—CH$_2$—OH, —CH(CH$_3$)—C(O)—N(H)—CH$_2$—COOH, —CH(CH$_3$)—C(O)—N(H)—CH$_2$—C(O)—O—CH$_2$—CH$_3$, —CH$_2$—C(O)—N(H)—CH$_2$—COOH, —CH$_2$—CH$_2$—C(O)—N(H)—CH$_2$—COOH, —CH(CH$_3$)—CH$_2$—C(O)—N(H)—CH$_2$—COOH, and —CH$_2$—CH(CH$_3$)—C(O)—N(H)—CH$_2$—COOH, substituted heteroaryl selected from: 5-chloro-1H-benzoimidazol-2-yl, 5-methoxy-1H-benzoimidazol-2-yl, 4-oxo-3,4-dihydro-quinazolin-2-yl, benzoselenazol-2-yl, and 5-substituted-benzothiazol-2-yl; heterocyclyl selected from: thiazol, 2-thioxo-imidazolidin-1-yl and morpholino, an optionally substituted nucleoside, or an optionally substituted di-, tri- or tetra-peptide, or —CH$_2$—C(O)—C(O)—O—R' or —CH=C(OH)—C(O)—O—R';

R is: hydrogen, optionally substituted alkyl, optionally substituted cycloalkyl, optionally substituted aryl, optionally substituted aralkyl, optionally substituted heteroaryl, optionally substituted heteroaralkyl, optionally substituted heterocyclyl or optionally substituted heterocycloalkyl;

R' is: independently selected from hydrogen, optionally substituted alkyl, optionally substituted cycloalkyl or optionally substituted aryl;

X is: —N(R')—, —S—, —S(O)—, —S(O)$_2$—, —S—Y—S—, or a covalent bond to the sulfur atom of Cys or to the nitrogen atom of optionally substituted heterocyclyl;

Y is: optionally substituted aryl, optionally substituted heteroaryl, an optionally substituted nucleoside, an optionally substituted amino acid, or an optionally substituted di-, tri- or tetra-peptide; and Z is: —OR or —SR;

including single tautomers, single stereoisomers and mixtures of tautomers and/or stereoisomers, and the pharmaceutically acceptable salts thereof. The invention also pertains to methods of treatment, pharmaceutical formulations and the manufacture of medicaments employing the compounds of Formula Ia.

Another aspect of the present invention concerns the compounds represented by Formula Ib:

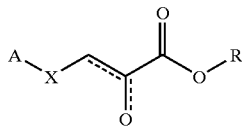

Formula Ib where:

A is: optionally substituted alkyl, optionally substituted cycloalkyl, optionally substituted aryl, optionally substituted aralkyl, optionally substituted heteroaryl, optionally substituted heteroaralkyl, optionally substituted heterocyclyl, optionally substituted heterocycloalkyl, an optionally substituted nucleoside, an optionally substituted amino acid, an optionally substituted di-, tri- or tetra-peptide, —CH$_2$—C(O)—C(O)—O—R' or —CH=C(OH)—C(O)—O—R';

R is: hydrogen, optionally substituted alkyl, optionally substituted cycloalkyl, optionally substituted aryl, optionally substituted aralkyl, optionally substituted heteroaryl, optionally substituted heteroaralkyl, optionally substituted heterocyclyl or optionally substituted heterocycloalkyl;

R$^a$ is: hydrogen, optionally substituted alkyl, optionally substituted aryl, optionally substituted aralkyl, or alkenyl;

R' is: independently selected from hydrogen, optionally substituted alkyl, optionally substituted cycloalkyl or optionally substituted aryl;

X is: —S—, —S(O)—, —S—Y—S—, or a covalent bond to the sulfur atom of Cys or to the nitrogen atom of optionally substituted heterocyclyl;

Y is: optionally substituted aryl, optionally substituted heteroaryl, an optionally substituted nucleoside, an optionally substituted amino acid, or an optionally substituted di-, tri- or tetra-peptide; and Z is: —OR or —SR;

including single tautomers, single stereoisomers and mixtures of tautomers and/or stereoisomers, and the pharmaceutically acceptable salts thereof; provided that:

where X is —S—, A is not optionally substituted alkyl, benzyl or an N-arylpyrroline-2,5-dione-substituted phenyl, and further provided that the compound of Formula 1b is not:
2-hydroxyimino-3-p-tolylsulfanyl-propionic acid ethyl ester.

The invention also pertains to methods of treatment, pharmaceutical formulations and the manufacture of medicaments employing the compounds of Formula 1b.

Another aspect of the present invention concerns the compounds represented by Formula Ic:

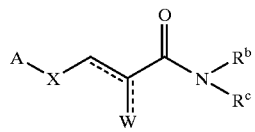

Formula Ic where:
A is: optionally substituted alkyl, optionally substituted cycloalkyl, optionally substituted aryl, optionally substituted aralkyl, optionally substituted heteroaryl, optionally substituted heteroaralkyl, optionally substituted heterocyclyl, optionally substituted heterocycloalkyl, an optionally substituted nucleoside, an optionally substituted amino acid, an optionally substituted di-, tri- or tetra-peptide, $CH_2$—C(O)—C(O)—O—R' or —CH=C(OH)—C(O)—O—R';

W is: =O, =N—$OR^a$, or —N(OH)—$R^d$;

X is: —S—, —S(O)—, —S(O)$_2$—, —S—Y—S—, or a covalent bond to the sulfur atom of Cys or to the nitrogen atom of optionally substituted heterocyclyl;

Y is: optionally substituted aryl, optionally substituted heteroaryl, an optionally substituted nucleoside, an optionally substituted amino acid, or an optionally substituted di-, tri- or tetra-peptide;

R' is: independently selected from hydrogen, optionally substituted alkyl, optionally substituted cycloalkyl or optionally substituted aryl;

$R^a$ is: hydrogen, optionally substituted alkyl, optionally substituted aryl, optionally substituted aralkyl, or alkenyl;

$R^b$ is: hydrogen, optionally substituted alkyl, optionally substituted aryl, optionally substituted aralkyl or optionally substituted cycloalkyl;

$R^c$ is: hydrogen or optionally substituted alkyl; and $R^d$ is: hydrogen, acyl or optionally substituted alkyl; or $R^b$ and $R^c$ together with the nitrogen to which they are attached may form a 5- to 7-membered ring, optionally incorporating one or two additional ring heteroatoms chosen from N, S, or O, and said ring being optionally substituted with one or more substituents independently selected from the group consisting of =O, =S, acyl, optionally substituted alkenyl, optionally substituted alkyl, (optionally substituted alkoxy)carbonyl, and (optionally substituted amino)carbonyl;

including single tautomers, single stereoisomers and mixtures of tautomers and/or stereoisomers, and the pharmaceutically acceptable salts thereof, provided that:
where X is —S—, A is not optionally substituted methyl, optionally substituted ethyl, optionally substituted benzyl, or triphenylmethyl, and
where W is =N—$OR^a$ and X is a covalent bond to the sulfur atom of Cys, A is an optionally substituted di-, tri- or tetra-peptide.

The invention also pertains to methods of treatment, pharmaceutical formulations and the manufacture of medicaments employing the compounds of Formula Ic.

In a preferred embodiment of Formulae I, Ia, Ib and Ic, where A is a natural or substituted amino acid or peptide, A is selected from the group: Ala, Asn, Asp, Cys, Gln, Glu, Gly, Lys, Met, Ser and Thr, especially Ala, Asp, Cys, Glu and Gly. Further preferred are those compounds where A is a natural or substituted di- or tri-peptide, especially natural peptides and most preferably the tri-peptide Glu-Cys-Gly.

In another such preferred embodiment, A is an optionally substituted heteroaryl group, especially a nitrogen-containing optionally substituted heteroaryl, and particularly where A is selected from the group: imidazole, triazole, thiadiazole, oxadiazole, benzoselenazol, benzoimidazole and benzothiazole.

Further preferred in each of the foregoing embodiments are those compounds where X is —S— or a covalent bond.

Another preferred embodiment of the invention concerns the compounds, represented by Formula II:

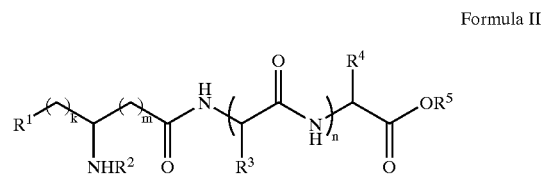

Formula II where:
$R^1$ is: hydrogen, optionally substituted alkyl, optionally substituted aryl, —C(O)—O—R', —$CH_2$—SH, —$CH_2$—S—$CH_2$—C(W)—C(O)-Z, —$CH_2$—S—CH=C(OH)—C(O)-Z, —$CH_2$—S(O)—$CH_2$—C(W)—C(O)-Z, or —$CH_2$—S(O)—CH=C(OH)—C(O)-Z';

$R^2$ is: hydrogen, optionally substituted alkyl, optionally substituted aryl, optionally substituted aralkyl, optionally substituted acyl;

$R^3$ is: independently selected from hydrogen, optionally substituted lower alkyl, optionally substituted aralkyl, —$CH_2$—SH, —$CH_2$—S—$CH_2$—C(W)—C(O)-Z, —$CH_2$—S—CH=C(OH)—C(O)-Z, —$CH_2$—S(O)—$CH_2$—C(W)—C(O)-Z, or —$CH_2$—S(O)—CH=C(OH)—C(O)-Z;

$R^4$ is: hydrogen, optionally substituted lower alkyl, optionally substituted aralkyl, optionally substituted heteroararalkyl, —$CH_2$—SH, —$CH_2$—S—$CH_2$—C(W)—C(O)-Z, —$CH_2$—S—CH=C(OH)—C(O)-Z, —$CH_2$—S(O)—$CH_2$—C(W)—C(O)-Z, or —$CH_2$—S(O)—CH=C(OH)—C(O)-Z;

$R^5$ is: hydrogen, optionally substituted alkyl, or optionally substituted aryl;

R' is: independently selected from hydrogen, optionally substituted alkyl, or optionally substituted aryl;

W is: =O, =N—$OR^a$, =N—$NR^bR^c$; or —N(OH)—$R^d$

Z is: —OR, —SR, or —$NR^bR^c$;

R is: hydrogen, optionally substituted alkyl, optionally substituted cycloalkyl, optionally substituted aryl, optionally substituted aralkyl, optionally substituted heteroaryl, optionally substituted heteroaralkyl, optionally substituted heterocyclyl or optionally substituted heterocycloalkyl;

$R^a$ is: hydrogen, optionally substituted alkyl, optionally substituted aryl, optionally substituted aralkyl, or alkenyl;

$R^b$ is: independently selected from hydrogen, optionally substituted alkyl, optionally substituted aryl, optionally substituted aralkyl or optionally substituted cycloalkyl, $R^c$ is: independently selected from hydrogen or optionally substituted alkyl; and $R^d$ is: hydrogen, acyl or optionally substituted alkyl; or $R^b$ and $R^c$ together with the nitrogen to which they are attached may form an 5- to 7-membered ring, optionally incorporating one or two additional ring heteroatoms chosen from N, S, or O, and said ring being optionally substituted with one or more substituents independently selected from the group consisting of =O, =S, acyl, optionally substituted alkenyl, optionally substituted alkyl, (optionally substituted alkoxy)carbonyl, and (optionally substituted amino)carbonyl;

k is: 0, 1 or 2;

m is: 0, 1 or 2; and n is: 0, 1, 2 or 3;

including single tautomers, single stereoisomers and mixtures of tautomers and/or stereoisomers, and the pharmaceutically acceptable salts thereof, provided that at least one of $R^1$, $R^3$ or $R^4$ is —$CH_2$—S—$CH_2$—C(W)—C(O)-Z, —$CH_2$—S—CH=C(OH)—C(O)-Z, —$CH_2$—S(O)—$CH_2$—C(W)—C(O)-Z, or —$CH_2$—S(O)—CH=C(OH)—C(O)-Z. The invention also pertains to methods of treatment, pharmaceutical formulations and the manufacture of medicaments employing the compounds of Formula II.

Of the compounds according to Formula II, preferred are those compounds the substituents of which are selected from the following groups:

$R^1$ is: —C(O)—O—R' where R' is hydrogen or lower alkyl;

$R^2$ is: hydrogen;

$R^3$ is: —$CH_2$—S—$CH_2$—C(W)—C(O)-Z, —$CH_2$—S—CH=C(OH)—C(O)-Z, —$CH_2$—S(O)—$CH_2$—C(W)—C(O)-Z, or —$CH_2$—S(O)—CH=C(OH)—C(O)-Z $R^4$ is: hydrogen;

$R^5$ is hydrogen or lower alkyl;

W is: =O or =N—$OR^a$;

Z is: —OR or —$NR^bR^c$;

R is: hydrogen, optionally substituted alkyl, optionally substituted cycloalkyl, optionally substituted aryl, or optionally substituted aralkyl;

$R^a$ is: hydrogen or alkyl;

$R^b$ is: $C_1$ to $C_4$ alkyl, phenyl or benzyl;

$R^c$ is: hydrogen or $C_1$ to $C_4$ alkyl, or $R^b$ and $R^c$ together with the nitrogen to which they are attached form a 6-membered ring selected from 4-optionally substituted-piperidin-1-yl and morpholin-4-yl; and k, m and n are respectively: 0,2,1; 1,0,1; or 2,0,1.

Another aspect of the invention entails compounds made from the compounds of Formula Ia, for example, where A is cysteine, by cyclization to give a dihydrothiazine-3,5-dicarboxylic acid or like derivative, as represented by Formula III:

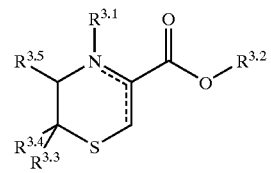

Formula III where:

the dashed line represents a double bond at one or the other of the indicated positions, corresponding to a 3,4-dihydro-2H-[1,4]thiazine or a 3,6-dihydro-2H-[1,4]thiazine (or 5,6-dihydro-2H-[1,4]thiazine in the nomenclature of the compounds where $R^{3.5}$ is H);

$R^{3.1}$ is: H where Formula III is a 3,4-dihydro-2H-[1,4]thiazine, and is absent where Formula III is a 3,6-dihydro-2H-[1,4]thiazine;

$R^{3.2}$ is: H or $C_1$ to $C_4$ alkyl;

$R^{3.3}$ and $R^{3.4}$ are both H or are both $C_1$ to $C_4$ alkyl; and $R^{3.5}$ is: H, COOH, or —C(O)O—$C_1$ to $C_4$ alkyl;

including single tautomers, single stereoisomers and mixtures of tautomers and/or stereoisomers, and the pharmaceutically acceptable salts thereof. The invention also pertains to methods of treatment, pharmaceutical formulations and the manufacture of medicaments employing the compounds of Formula III.

In another aspect, the invention relates to a pharmaceutical composition containing a therapeutically effective amount of a compound of Formulae I, Ia, Ib, Ic, II or III or a pharmaceutically acceptable salt thereof admixed with at least one pharmaceutically acceptable excipient. Particularly preferred are those pharmaceutical compositions wherein the compound of Formulae I, Ia, Ib, Ic, II or III is selected from the herein-described preferred embodiments.

In still another aspect, the invention relates to a method of treatment by administering to a mammal in need of such treatment a therapeutically effective amount of a compound of Formulae I, Ia, Ib, Ic, II or III or a pharmaceutically acceptable salt thereof, where the disease, condition or indication for which treatment is provided is: ischemia including stroke, cerebral ischemia, retinal ischemia, myocardial ischemia, myocardial infarction and post-surgical cognitive dysfunction; neurodegenerative disorders including Alzheimer's, dementia and Parkinson's disease; peripheral neuropathy, including spinal cord injury, head injury and surgical trauma; inflammatory disorders including diabetes, renal disease, pre-menstrual syndrome, asthma, cardiopulmonary inflammatory disorders, heart failure, rheumatoid arthritis, osteoarthritis, muscle fatigue and intermittent claudication; and for the preservation of allograft tissue and organs for transplantation. Particularly preferred are those methods of treatment and uses in the manufacture of pharmaceutical compositions therefore, wherein the compound of Formulae I, Ia, Ib, Ic, II or III is selected from the herein-described preferred embodiments.

DETAILED DESCRIPTION OF THE INVENTION

Definitions

As used in the present specification, the following words and phrases are generally intended to have the meanings as set forth below, except to the extent that the context in which they are used indicates otherwise.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible.

Certain compound, reactant, or reaction parameter abbreviations are defined as follows:

"DCM" refers to dichloromethane or methylene chloride
"DIC" refers to N, N-diisopropylcarbodiimide.
"DIPEA" refers to diisopropyl ethylamine.
"DMAP" refers to 4-N, N-dimethylamino pyridine.
"DMF" refers to N, N-dimethyl formamide.
"DTT" refers to dithiothreitol.
"EDT" refers to ethanedithiol.
"Eq." refers to equivalent.
"Fmoc" refers to 9-fluorenylmethoxycarbonyl.
"GlyOH" refers to glycine.
"HOBt" refers to N-hydroxybenzotriazole.
"MeOH" refers to methanol.
"t-Bu" refers to t-butyl.
"TBTU" refers to 2-(1H-benzotriazole-1-yl)-1,1,3,3-tetramethyluronium tetrafluoroborate.
"TIS" refers to triisopropylsilane.
"TFA" refers to trifluoroacetic acid.

The term "acyl" refers to the groups —C(O)—H, —C(O)-(optionally substituted alkyl), —C(O)-(optionally substituted cycloalkyl), —C(O)-(optionally substituted alkenyl), —C(O)-(optionally substituted cycloalkenyl), —C(O)-(optionally substituted aryl), —C(O)-(optionally substituted aralkyl), —C(O)-(optionally substituted heteroaryl), —C(O)-(optionally substituted heteroaralkyl), —C(O)-(optionally substituted heterocyclyl) and —C(O)-(optionally substituted heterocycloalkyl).

The term "acyloxy" refers to the moiety —O-acyl, including, for example, —O—C(O)-alkyl.

The term "alkenyl" refers to the monoradical branched or unbranched, unsaturated or polyunsaturated hydrocarbon chain, having from about 2 to 20 carbon atoms, more preferably about 2 to 10 carbon atoms. This term is exemplified by groups such as ethenyl, but-2-enyl, and the like.

The term "alkoxy" refers to the groups —O-alkyl, —O-alkenyl, —O-cycloalkyl, —O-cycloalkenyl, and —O-alkynyl. Preferred alkoxy groups are —O-alkyl and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups —O-(substituted alkyl), —O-(substituted alkenyl), —O-(substituted cycloalkyl), —O-(substituted cycloalkenyl), —O-(substituted alkynyl) and —O-(optionally substituted alkylene)-alkoxy.

The term "alkyl" refers to a monoradical branched or unbranched saturated hydrocarbon chain preferably having from about 1 to 20 carbon atoms, more preferably about 1 to 10 carbon atoms, and even more preferably about 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to:an alkyl group in which 1 or more (up to about 5, preferably up to about 3) hydrogen atoms is replaced by a substituent independently selected from the group: =O, =S, acyl, acyloxy, optionally substituted alkoxy, optionally substituted amino, azido, carboxyl, (optionally substituted alkoxy)carbonyl, (optionally substituted amino)carbonyl, cyano, optionally substituted cycloalkyl, optionally substituted cycloalkenyl, halogen, hydroxyl, nitro, sulfanyl, sulfinyl, and sulfonyl. One of the preferred optional substituents for alkyl is hydroxy, exemplified by hydroxyalkyl groups, such as 2-hydroxyethyl, 3-hydroxypropyl, 3-hydroxybutyl, 4-hydroxybutyl, and the like; dihydroxyalkyl groups (glycols), such as 2,3-dihydroxypropyl, 3,4-dihydroxybutyl, 2,4-dihydroxybutyl, and the like; and those compounds known as polyethylene glycols, polypropylene glycols and polybutylene glycols, and the like. Another preferred substitutent for alkyl is optionally substituted alkoxy carbonyl, such as 1-methoxycarbonyl-ethyl.

The term "alkylene" refers to a diradical derived from the above-defined monoradical, alkyl. This term is exemplified by groups such as methylene (—CH$_2$—), ethylene (—CH$_2$CH$_2$—), the propylene isomers [e.g., —CH$_2$CH$_2$CH$_2$— and —CH(CH$_3$)CH$_2$—] and the like.

The term "substituted alkylene" refers to a diradical derived from the above-defined monoradical, substituted alkyl. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers (—CH$_2$CH(CO$_2$H)CH$_2$—), ethoxyethylene (—CH$_2$CH$_2$O—CH$_2$CH$_2$—), ethyl(N-methyl)aminoethylene (—CH$_2$CH$_2$N(CH$_3$)CH$_2$CH$_2$—), 1-ethoxy-2-(2-ethoxy-ethoxy)ethylene (—CH$_2$CH$_2$O—CH$_2$CH$_2$—OCH$_2$CH$_2$—OCH$_2$CH$_2$—), and the like.

The term "amino" refers to the group —NH$_2$.

The term "substituted amino" refers to the group —NHR or —NRR where each R is independently selected from the group: optionally substituted alkyl, optionally substituted cycloalkyl, optionally substituted alkenyl, optionally substituted cycloalkenyl, optionally substituted alkynyl, optionally substituted aryl, optionally substituted heteroaryl, optionally substituted heterocyclyl, acyl, optionally substituted alkoxy, carboxy and alkoxycarbonyl.

The term "amino acid" or "natural amino acid" refers to any of the twenty (20) common amino acids as generally accepted in the peptide art and represent L-amino acids unless otherwise designated (with the exception of achiral amino acids such as glycine).

The term "substituted amino acid" refers to an amino acid containing one or more additional chemical moieties that are not normally a part of the amino acid. Such substitutions can be introduced by a targeted deriviatizing agent that is capable of reacting with selected side chains or terminal residues and via other art-accepted methods. For example, cysteinyl residues most commonly are reacted with .alpha.-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions. Glutaminyl and asparaginyl residues are frequently deamidated to the corresponding glutamyl and aspartyl residues. Alternatively, these residues are deamidated under mildly acidic conditions. Other modifications include hydroxylation of proline and lysine, phosphorylation of hydroxyl groups of seryl or theonyl residues, methylation of the .alpha.-amino groups of lysine, arginine, and histidine side chains (see, e.g., T. E. Creighton, Proteins: Structure and Molecule Properties, W.H. Freeman & Co., San Francisco, pp. 79–86 (1983)), acetylation of the N-terminal amine, and, in some instances, amidation of the C-terminal carboxyl groups.

The term "aromatic" refers to a cyclic or polycyclic moiety having a conjugated unsaturated (4n+2)π electron system (where n is a positive integer), sometimes referred to as a delocalized π electron system.

The term "aryl" refers to an aromatic cyclic hydrocarbon group of from 6 to 20 carbon atoms having a single ring (e.g., phenyl) or multiple condensed (fused) rings (e.g., naphthyl or anthryl). Preferred aryls include phenyl, naphthyl and the like.

The term "substituted aryl" refers to an aryl group as defined above, which unless otherwise constrained by the definition for the aryl substituent, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, and sulfonyl. Preferred aryl substituents include alkyl, alkoxy, halo, cyano, nitro, trihalomethyl, and sulfinyl.

The term "aryloxy" refers to the group —O-aryl.

The term "substituted aryloxy" refers to the group —O-(substituted aryl).

The term "aralkyl" refers to the moiety "-alkylene-aryl" each having the meaning as defined herein. Such aralkyl groups are exemplified by benzyl, phenethyl, 3-naphthylpropyl and the like.

The term "substituted aralkyl" refers to the moiety "-(optionally substituted aklylene)- (optionally substituted aryl)", each having the meaning as defined herein, where at least one of the aryl or alkylene groups is substituted, e.g., 4-(N-methyl-pyrrolyl)pentylene, 4-nitrobenzyl or 1-methoxycarbonyl-2-phenyl-ethyl.

The term "carbonyl" refers to the di-radical "—C(=O)—", which is also illustrated as "—C(O)—".

The term "(optionally substituted alkoxy)carbonyl" refers to the groups: —C(O)O-(optionally substituted alkyl), —C(O)O-(optionally substituted cycloalkyl), —C(O)O-(optionally substituted alkenyl), and —C(O)O-(optionally substituted alkynyl). These moieties are also referred to as esters.

The term "(optionally substituted amino)carbonyl" refers to the group —C(O)-(optionally substituted amino). This moiety is also referred to as a primary, secondary or tertiary carboxamide.

The term "(optionally substituted amino)carbonyloxy" refers to the group —O—C(O)-(optionally substituted amino).

The term "carboxy" or "carboxyl" refers to the moiety "—C(O)OH", which is also illustrated as "—COOH".

The term "compound of Formula I" is intended to encompass the pyruvate derivatives of the invention as disclosed, and/or the pharmaceutically acceptable salts of such compounds. In addition, the compounds of this invention include the keto and enol pyruvate tautomers, individual stereochemical isomers (arising from the selection of substituent groups) and mixtures of tautomers and/or isomers.

The term "cycloalkyl" refers to non-aromatic cyclic hydrocarbon groups of having about 3 to 40 (preferably about 4 to 15) carbon atoms having a single ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, cyclopentaphenanthren and the like.

The term "substituted cycloalkyl" refers to a cycloalkyl group substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, and sulfonyl.

The term "halo" or "halogen" refers to fluoro, chloro, bromo and iodo.

The term "heteroaryl" refers to an aromatic cyclic hydrocarbon group having about 1 to 40 (preferably from about 3 to 15) carbon atoms and about 1 to 10 hetero atoms (preferably about 1 to 4 heteroatoms, selected from nitrogen, sulfur, phosphorus, selenium and/or oxygen) within at least one ring. Such heteroaryl groups can have a single ring (e.g., pyridyl or furyl) or multiple condensed rings (e.g., indolizinyl or benzothienyl). Preferred heteroaryls include pyridyl, pyrrolyl, furyl, benzoimidazole, benzothiazole and benzoselenazol.

The term "substituted heteroaryl" refers to a heteroaryl group as defined above, which unless otherwise constrained by the definition for the heteroaryl substituent, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, and sulfonyl.

The term "heteroaralkyl" refers to the moiety "-alkylene-heteroaryl" each having the meaning as defined herein.

The term "substituted heteroaralkyl" refers to the moiety "-(optionally substituted aklylene)-(optionally substituted heteroaryl)", each having the meaning as defined herein.

The term "heteroaryloxy" refers to the group —O-heteroaryl.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The terms "heterocycle", "heterocyclic" and "heterocyclyl" refer to a monoradical, saturated or unsaturated, non-aromatic cyclic hydrocarbon group having about 1 to 40 (preferably from about 3 to 15) carbon atoms and about 1 to 10 hetero atoms (preferably about 1 to 4 heteroatoms, selected from nitrogen, sulfur, phosphorus, and/or oxygen) within the ring. Such heterocyclic groups can have a single ring or multiple condensed rings. Preferred heterocyclics include morpholino, piperidinyl, and the like.

The terms "substituted heterocycle", "substituted heterocyclic" and "substituted heterocyclyl" refer to a heterocyclyl group as defined above, which unless otherwise constrained by the definition for the heterocycle, is substituted with from 1 to 5 substituents, and preferably 1 to 3 substituents, independently selected from the group consisting of: =O, =S, acyl, acyloxy, optionally substituted alkenyl, optionally substituted alkoxy, optionally substituted alkyl (such as tri-halomethyl), optionally substituted alkynyl, optionally substituted amino, optionally substituted aryl, optionally substituted aryloxy, azido, carboxyl, (optionally substituted alkoxy)carbonyl, (optionally substituted amino)carbonyl, cyano, optionally substituted cycloalkyl, optionally substituted cycloalkenyl, halogen, optionally substituted heteroaryl, optionally substituted heteroaryloxy, optionally substituted heterocyclyl, optionally substituted heterocyclooxy, hydroxyl, nitro, sulfanyl, sulfinyl, and sulfonyl.

The term "heterocycloalkyl" refers to the moiety "-alkylene-heterocycle" each having the meaning as defined herein.

The term "substituted heterocycloalkyl" refers to the moiety "-(optionally substituted aklylene)-(optionally substituted heterocycle)", each having the meaning as defined herein.

The term "heterocyclooxy" refers to the group —O-heterocycle.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts which retain the biological effectiveness and properties of the compounds of this invention and which are not biologically or otherwise undesirable. In many cases, the compounds of this invention are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "sulfanyl" refers to the groups: —S-(optionally substituted alkyl), —S-(optionally substituted aryl), —S-(optionally substituted heteroaryl), —S-(optionally substituted heterocyclyl). Preferred sulfanyl groups include, by way of example, methylsulfanyl (—SCH$_3$), n-(iso-propylsulfanyl) (—SCH(CH$_3$)$_2$) and the like.

The term "sulfinyl" refers to the groups: —S(O)-(optionally substituted alkyl), —S(O)-optionally substituted aryl), —S(O)-(optionally substituted heteroaryl), —S(O)-(optionally substituted heterocyclyl).

The term "sulfonyl" refers to the groups: —S(O$_2$)-(optionally substituted alkyl), —S(O$_2$)-optionally substituted aryl), —S(O$_2$)-(optionally substituted heteroaryl), —S(O$_2$)-(optionally substituted heterocyclyl).

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the particular compound of Formula I chosen, the dosing regimen to be followed, timing of administration, the manner of administration and the like, all of which can readily be determined by one of ordinary skill in the art.

The term "treatment" or "treating" means any treatment of a disease or disorder in a mammal, including:

preventing or protecting against the disease or disorder, that is, causing the clinical symptoms not to develop;

inhibiting the disease or disorder, that is, arresting or suppressing the development of clinical symptoms; and/or relieving the disease or disorder, that is, causing the regression of clinical symptoms.

It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The term "effective amount" means a dosage sufficient to provide treatment for the disorder or disease state being treated. This will vary depending on the patient, the disease and the treatment being effected.

The term "disorder" or "disease state" means any disease, condition, symptom, or indication.

Compounds of the Invention

The compounds employed in the practice of the present invention are those identified above with reference to Formulae I, Ia, Ib, Ic, II and III, and the precursors/intermediates described with reference to the Reaction Schemes. Formula I is addressed to certain known and novel pyruvate derivatives as employed in novel methods of treatment, pharmaeutical formulations and in the manufacture of medicaments for such methods of treatment. Formulae Ia, Ib, Ic, II and III are addressed to novel pyruvate derivatives, methods of treatment, pharmaeutical formulations and the manufacture of medicaments for such methods of treatment.

Nomenclature

The compounds of the present invention are named and numbered as described below, for example, with reference to Formulae Id, Ie, If, Ig, Ih, and IIIa.

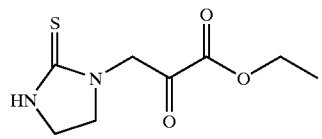

Formula Id

Formula Id represents the compound according to Formula Ia where A is 2-thioxo-imidazolidin-1-yl, R is ethyl, X is a covalent bond, where tautomeric form of the pyruvate (represented by the dashed line in Formula I) is the keto tautomer. In one nomenclature system, the compound of Formula Id is named: 2-oxo-3-(2-thioxo-imidazolidin-1-yl)-propionic acid ethyl ester. The compound of Formula Id can also be named as: (2-thioxo-imidazolidin-1-yl)methyl-ketopyruvate ethyl ester.

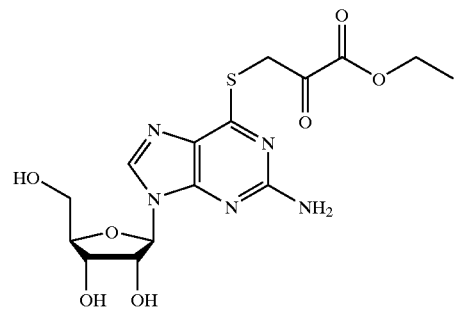

Formula Ie

Formula Ie represents the compound of Formula Ia where A is 3-[2-Amino-9-(3,4-dihydroxy-5-hydroxymethyl-tetrahydrofuran-2-yl)-9H-purin-6-yl, R is Ethyl, and X is S, which is named: 3-[2-amino-9-(3,4-dihydroxy-5-hydroxymethyl-tetrahydro-furan-2-yl)-9H-purin-6-ylsulfanyl]-2-oxo-propionic acid ethyl ester.

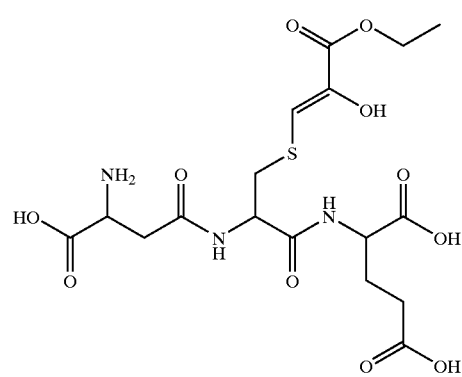

Formula If

Formula If represents the compound of Formula Ia where A is γ-Asp-Cys-Glu, R is ethyl, and X is a Covalent Bond where tautomeric form of the pyruvate (represented by the dashed line in Formula I) is the enol tautomer. This is also the compound of Formula II where $R^1$ is COOH, $R^2$ is H, $R^3$ is $CH_2$—S-Pyruvate ethyl ester, $R^4$ is optionally substituted alkyl where the substituent is COOH, $R^5$ is H, k is 0, m is 1, and n is 1. The compound of Formula If can be named: 2-[2-(3-amino-3-carboxy-propionylamino)-3-(2-ethoxycarbonyl-2-hydroxy-vinylsulfanyl)-propionylamino]-pentanedioic acid.

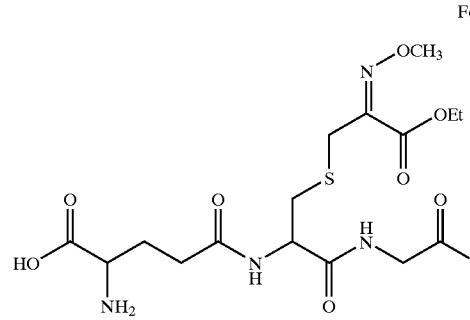

Formula Ig

Formula Ig represents a compound of Formula Ib where A is Glu-Cys-Gly, X is a covalent bond to the sulfur atom of Cys, W is =NOCH$_3$, and Z is O-ethyl. It is also a compound of Formula II where $R^1$ is COOH, $R^2$ is H, $R^3$ is $CH_2$—S—C(NOCH$_3$)C(O)OC$_2$H$_6$ $R^4$ and $R^5$ are H, k is 0, m is 2, and n is 1. The compound of Formula Ig can be named 2-amino-4-[1-(carboxymethyl-carbamoyl)-2-(2-ethoxycarbonyl-2-methoxyimino-ethylsulfanyl)-ethylcarbamoyl]-butyric acid.

Formula Ih

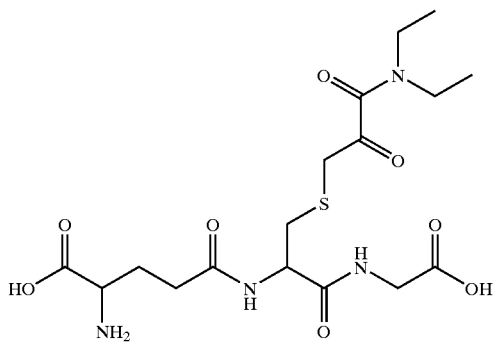

Formula Ih represents a compound of Formula Ic where A is Glu-Cys-Gly, X is a covalent bond to the sulfur atom of Cys, W is =O, and Z is —NR$^b$R$^c$ where R$^b$ and R$^C$ are both ethyl. It is also a compound of Formula II where $R^1$ is COOH, $R^2$ is H, $R^3$ is $CH_2$—S—C(O)C(O)N(C$_2$H$_6$)$_2$, $R^4$ and $R^5$ are H, k is 0, m is 2, and n is 1. The compound of Formula Ih can be named 2-amino-4-[1-(carboxymethyl-carbamoyl)-2-(2-diethylcarbamoyl-2-oxo-ethylsulfanyl)-ethylcarbamoyl]-butyric acid.

Formula IIIa

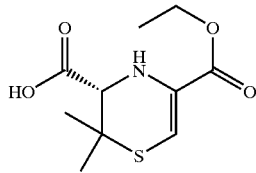

Formula IIIa represents a compound of Formula III where $R^{3.1}$ is hydrogen, $R^{3.2}$ is ethyl, $R^{3.3}$ and $R^{3.4}$ are both methyl, and $R^{3.5}$ is COOH. The compound of Formula IIIa can be named 2,2-dimethyl-3,4-dihydro-2H-[1,4]thiazine-3,5-dicarboxylic acid 5-ethyl ester.

Synthesis of the Compounds of the Invention

The compounds of Formulae I and II can be prepared by solution phase synthesis and, particularly in the case of the compounds of Formula II, by solid phase supported synthesis. These are described in greater detail below with reference to the Reaction Schemes.

Synthetic Reaction Parameters

The terms "solvent", "inert organic solvent" or "inert solvent" mean a solvent inert under the conditions of the reaction being described in conjunction therewith. Solvents employed in synthesis of the compounds of the invention include, for example, methanol, acetone, water, acetonitrile, 1,4-dioxane, dimethylformamide ("DMF"), benzene, toluene, tetrahydrofuran ("THF"), chloroform, methylene chloride (or dichloromethane), diethyl ether, pyridine and the like, as well as mixtures thereof. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from 0° C. to 110° C. (preferably from 0° C. to 25° C.; most preferably at "room" or "ambient" temperature, e.g., 20° C). Further, unless otherwise specified, the reaction times and conditions are intended to be approximate, e.g., taking place at about atmospheric pressure within a temperature range of about 0° C. to about 110° C. (preferably from about 0° C. to about 25° C.; most preferably at about "room" or "ambient" temperature, e.g., approximately 20° C.) over a period of about 1 to about 10 hours (preferably about 5 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Brief Description of Reaction Schemes

Reaction Schemes 1, 1a, 1b and 1c illustrate the solution phase synthesis of the compounds of Formulae I and II.

Reaction Schemes 2–6 illustrate the solid phase supported synthesis of peptide-pyruvate conjugate compounds of Formulae Ia and II.

Reaction Scheme 2 illustrates synthesis of peptide precursors to certain compounds of Formulae I and II, using Fmoc and 'Boc protecting groups. Solid phase supported synthesis of single amino acid-pyruvate conjugates, while not preferred, can be accomplished as illustrated and may be found advantageous with certain combinations of substituents.

Reaction Scheme 3 illustrates the solid phase supported synthesis of peptide-pyruvate conjugates from Fmoc-protected precursors, their de-protection, cleavage from the solid support, and isolation.

Reaction Scheme 4 illustrates the solid phase supported synthesis of peptide-pyruvate conjugates from 'Boc-protected precursors, their de-protection, cleavage from the solid support, and isolation.

Reaction Schemes 5 and 6 illustrates the solid phase supported coupling of different structural moieties onto a precursor's terminal amino group, followed by pyruvate conjugation, de-protection, cleavage and isolation to give peptide-pyruvate conjugates of Formula II where $R^2$ is other than hydrogen.

With regard to Reaction Schemes 3 through 6, it should be noted (for the compounds having more than one amino acid) that the site of pyruvate conjugation need not be on the illustrated amino acid, but can be from any of the amino acid positions. Thus, for example, while Formula 300c illustrates the synthesis of a compound having the pyruvate conjugate at AA2, the Formula 300c is intended to encompass the compounds where the —CH$_2$—S-L group is on AA$_1$, AA$_2$ or AA$_3$, i.e., all of the following:

Formulae 300c

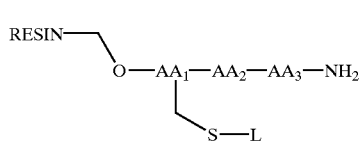

RESIN—
   O—AA₁—AA₂—AA₃—NH₂
                |
                S—L

RESIN—
   O—AA₁—AA₂—AA₃—NH₂
                |
                S—L

Only a single, representative position for pyruvate conjugation is illustrated for each of the compound in these reaction schemes, the others having been omitted for the sake of brevity.

Reaction Scheme 7 illustrates another solid phase supported approach for the synthesis and derivitization of resin-imine-pyruvates, as further described in co-pending applications Ser. No. 60/288,649, filed May 3, 2001, and Ser. No. 60/288,649 entitled "PROCESS FOR SOLID SUPPORTED SYNTHESIS OF PYRUVATE-DERIVED COMPOUNDS" filed on even date herewith.

Starting Materials

The compound ethyl-3-bromopyruvate is commercially available, e.g., from Aldrich Chemical Company, Milwaukee, Wis. N-Fmoc- and N-$^t$Boc-protected amino acids, including S-t-butylthio- and S-trityl-cysteine, are available, e.g., from Advanced ChemTech, Inc. of Louisville, Ky. Other reactants, such as p-toluenesulfonic acid, 3H-imidazole-4-thiol, and solid supports such as Wang resin are likewise commercially available or may be readily prepared by those skilled in the art using commonly employed methodology.

Preparation of Formula I

Reaction Scheme 1

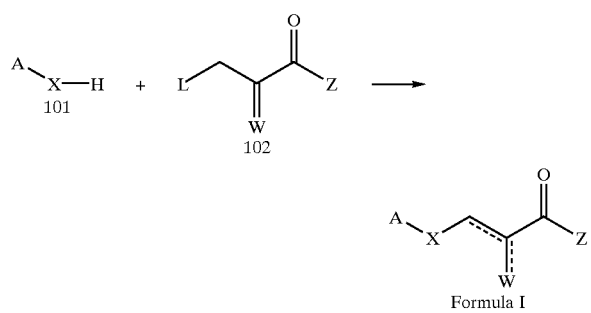

Formula I

Referring to Reaction Scheme 1, approximately equimolar equivalents of a compound of Formula 101 where A and X have the meanings previously described, such as:
 an aryl, aralkyl, heteroaryl or heteroaralkyl compound,
 a nucleoside, amino acid, di-, tri- or tetra-peptide,
  an aryl-amide, -thiol, -sulfane, -sulfone, -mercaptopyruvate-thiol,
  an aralkyl-amide, -thiol, -sulfane, -sulfone, -mercaptopyruvate-thiol,
  a heteroaryl-amide, -thiol, -sulfane, -sulfone, -mercaptopyruvate-thiol, or
  a heteroaralkyl-amide, -thiol, -sulfane, -sulfone, -mercaptopyruvate-thiol,
(any of which compounds of Formula 101 may optionally be substituted) and a compound of Formula 102 where Z has the meaning previously described and L is a leaving group such as a halide (preferably a bromide) together with an appropriate solvent (such as methanol, acetone, water, acetonitrile, 1,4-dioxane or DMF) are contacted in a suitable reaction vessel, optionally in the presence of an organic base (such as a tertiary amine or imidazole). The reaction takes place at a temperature from 0° C. to 110° C. (preferably 0° C. to 25° C.) for 30 minutes to 15 hours (preferably 3–5 hours), followed by removal of the solvent(s), isolation and purification to give the corresponding product of Formula I. Additional isolation and purification steps well known to those skilled in the art may be performed, e.g., to provide single isomers and/or tautomers.

Preparation of Formula Ia

Reaction Scheme 1a

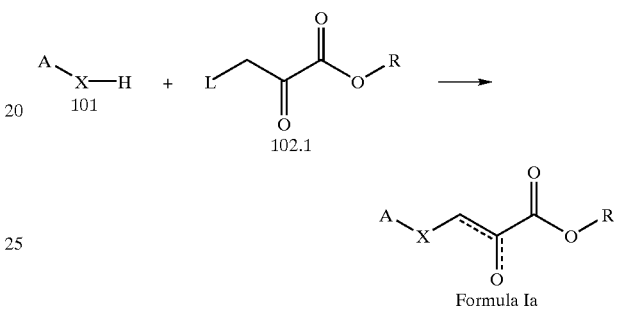

Formula Ia

Referring to Reaction Scheme 1a, the compounds of Formula Ia are prepared as described above with reference to Reaction Scheme 1, employing a compound of Formula 102.1 (e.g., an optionally alkyl- or aryl-substituted halopyruvate).

Preparation of Formula Ib

Reaction Scheme 1b

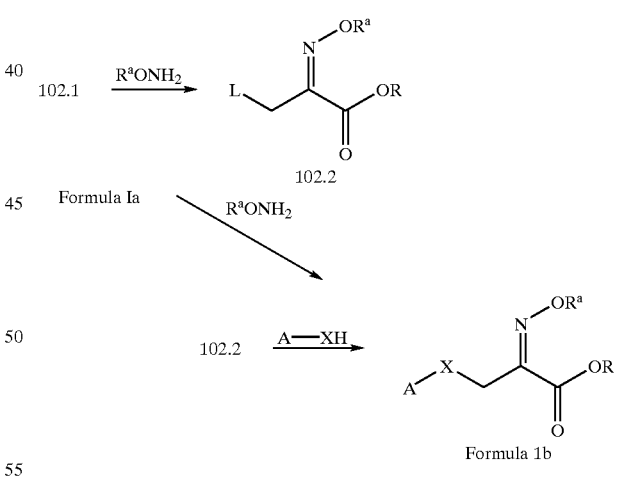

Formula Ib

Referring to Reaction Scheme 1b, a compound of Formula 102.1 is contacted with a compound of the formula R$^a$ONH₂ and converted to the corresponding oxime of Formula 102.2, which is then contacted with a compound of Formula 101 as described above with reference to Reaction Scheme 1. Alternatively, the compound of the formula R$^a$OH₂ can be employed with a compound of Formula 1a to give the corresponding oxime of Formula 1 b. Reductive alkylation or acylation of a compound of Formula 1b can be employed to obtain the corresponding compounds of Formula I where W is —N(OH)—R$^d$.

In like fashion, reaction of a compound of Formula Ia with a compound of the formula $R^bR^cNNH_2$ will give the corresponding compounds of Formula I where W is $=N-NR^bR^c$.

Preparation of Formula Ic

Reaction Scheme 1c

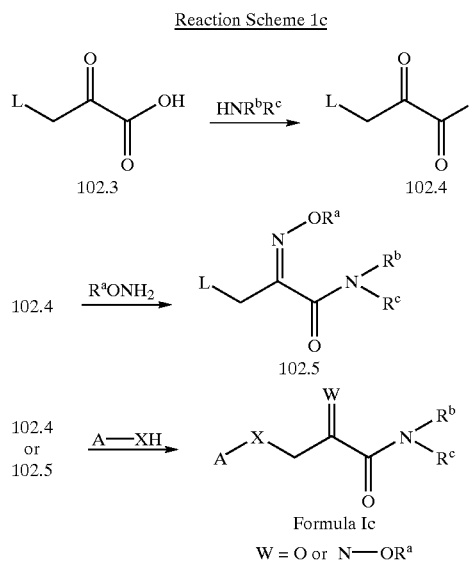

Formula Ic
W = O or N—OR$^a$

Referring to Reaction Scheme 1c, a pyruvic acid of Formula 102.3 is contacted with a secondary amine of the formula $HNR^bR^c$ to give the corresponding compound of Formula 102.4, which can be converted to the corresponding oxime of Formula 102.5 via reaction with a compound of Formula $R^aOH_2$. The compounds of Formulae 102.4 and 102.5 can be converted to the corresponding compounds of Formula Ic by raction with a compound of Formula 101 (A-XH) as described above.

Similarly, starting with a compound of Formula Ic where W is O, reaction with $R^aONH_2$ or $R^bR^cNNH_2$ will give the corresponding compounds of Formula Ic where W is $=N-O-R^a$ or $=N-NR^bR^c$. Reductive alkylation or acylation of a compound of Formula 1c can be employed to obtain the corresponding compounds of Formula I where W is $-N(OH)-R^d$.

Preparation of Formula II

The compounds of Formula II, particularly polypeptides can be prepared, with few exceptions, using solid phase support synthesis methods. These are illustrated with reference to Reaction Schemes 2 through 6.

Reaction Scheme 2

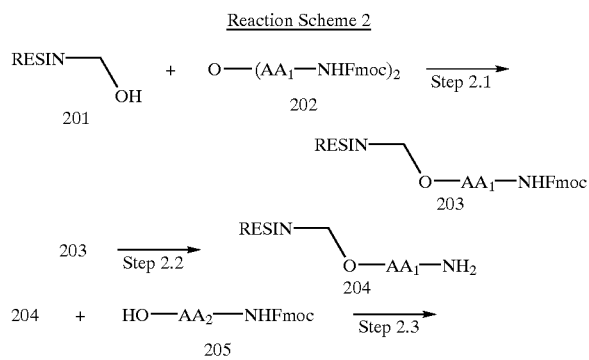

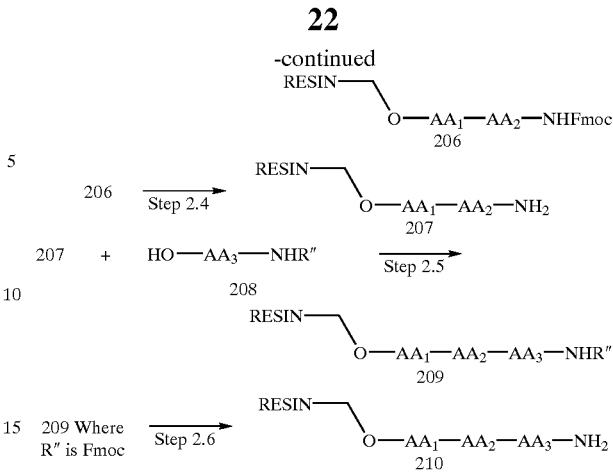

As illustrated in Reaction Scheme 2, Step 2.1, a solid support 201 (such as Wang resin) and a symmetrical Fmoc-protected amino acid anhydride 202 are linked employing Fmoc coupling/de-protecting protocols known in the art, to give the corresponding resin-bound, Fmoc-protected amino acid of Formula 203. For example, to approximately 10 molar equivalents of GlyOH dissolved in DCM is added DIC (5 eq) in small portion with stirring. Stirring is continued for 1 hour, after which the solution is added to the Wang resin (1 eq, pre-swelled in DMF) in the presence of 0.1 molar equivalent of DMAP. The resin suspension is shaken for 1 hour, followed by a thorough wash with DMF. The resulting prepared resin 201 is coupled with 2 molar equivalents of amino acid anhydride 202 using TBTU (2 eq), DIPEA (4 eq), followed by DMF wash (3 times). Formula 203 is de-protected (as shown in Step 2.2), e.g., using 20% piperidine in DMF followed by a DMF wash (5 times), to give the resin-bound amino acid of Formula 204, which may be linked to additional amino acids (as shown in Step 2.3) or conjugated to pyruvate (as shown in Reaction Scheme 3).

A resin-bound amino acid of Formula 204 is coupled with a protected amino acid, such as 205, to give resin-bound, Fmoc-protected di-peptide of Formula 206, which is de-protected to give the corresponding resin-bound di-peptide of Formula 207, which may be linked to additional amino acids (as shown in Step 2.5) or conjugated to pyruvate (as shown in Reaction Scheme 3). The reactions take place under conditions similar to those discussed above with respect to Steps 2.1 and 2.2. (Formula 205 is illustrated as Fmoc protected, but as will be apparent to those skilled in the art, may optionally be N-$^t$Boc-protected).

As illustrated in Step 2.5, the N-terminal amino acid unit (e.g., $AA_3$) can be either N-Fmoc- or N-$^t$Boc-protected. A resin-bound di-peptide of Formula 207 is coupled with a protected amino acid, such as 208, to give resin-bound, protected tri-peptide of Formula 209. The reaction takes place under conditions similar to those discussed above with respect to Step 2.3. As illustrated in Step 2.6, N-Fmoc-protected tripeptides of Formula 209 are de-protected under conditions similar to those discussed above with respect to Step 2.4, and then conjugated to pyruvate (e.g., as shown in Reaction Scheme 3). N-$^t$Boc-protected, resin-linked peptides (such as those of Formulae 206 or 209) are carried forward as illustrated in Reaction Scheme 4.

Reaction Scheme 3

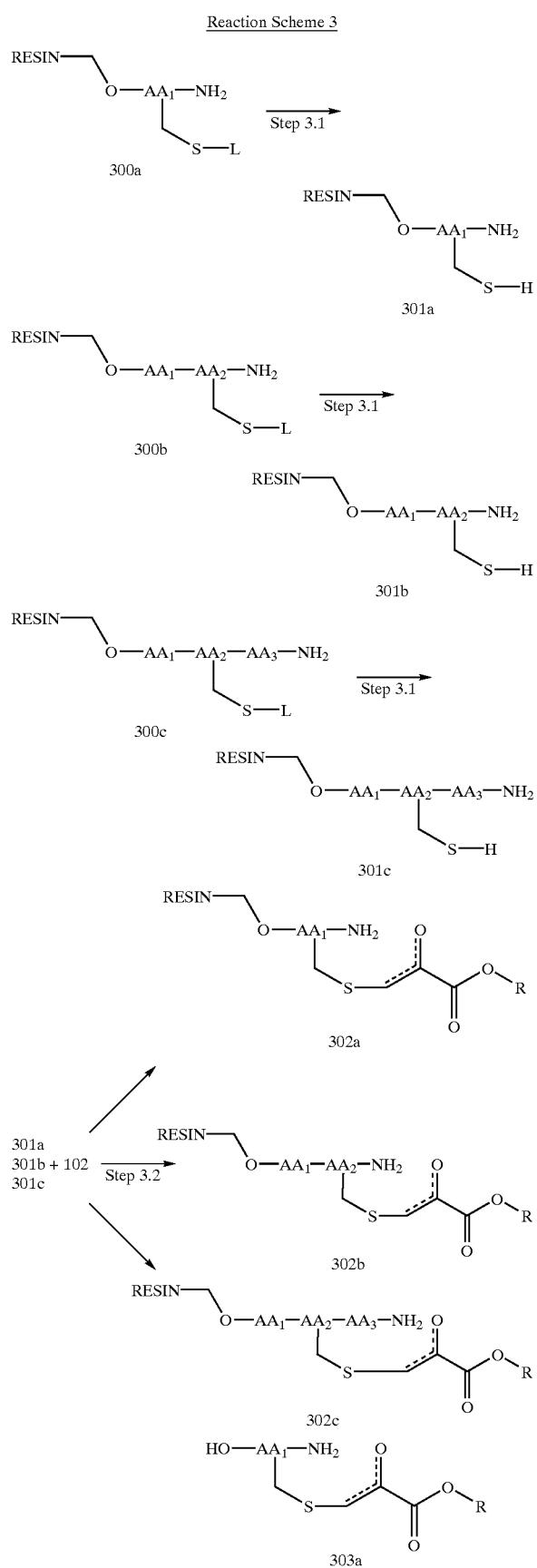

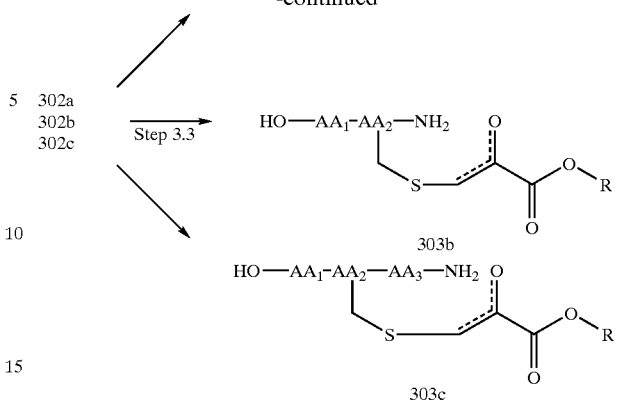

Reaction Scheme 3 describes a synthetic route to the peptide-pyruvate conjugates starting from previously N-Fmoc-protected resin-linked peptide precursors, such as those of Formulae 204, 207 and 210 (corresponding to starting compounds 300a, 300b and 300c), which are respectively illustrated as having a protected Cysteine at $AA_1$, $AA_2$ and $AA_2$, respectively (the protecting group, e.g., t-Butyl or trityl being designated as "L"). The protecting groups are introduced with the corresponding amino acid in Steps 2.1, 2.3 and/or 2.5. It will be appreciated that any of amino acids $AA_1$, $AA_2$ and $AA_3$ (or a fourth amino acid, not shown) can be Cysteine as employed in Reaction Schemes 3, 4, 5 and 6, to give the corresponding peptide-pyruvate conjugates at $AA_1$, $AA_2$ and/or $AA_3$.

The cysteine of a resin-linked peptide, such as 300a, 300b and 300c, as illustrated in Step 3.1, is de-protected by treating with dithiothreitol to give the corresponding compound of Formula 301a, 301b or 301c. This is followed by conjugation of the de-protected thio group with two molar equivalents of a halopyruvate of Formula 102 by nucleophilic substitution, as illustrated in Step 3.2. The resulting resin-bound peptide-pyruvate conjugate of Formula 302a, 302b or 302c is then cleaved from the resin under acidic conditions, e.g., with 95% TFA (aq.), isolated and then purified by typical methods (e.g., cold ether wash, filtration and lyophilization) to give the corresponding free peptide-pyruvate conjugate of Formula 303a, 303b or 303c.

Reaction Scheme 4

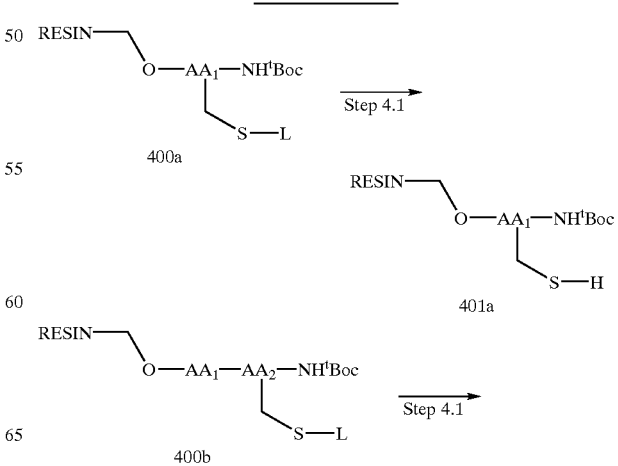

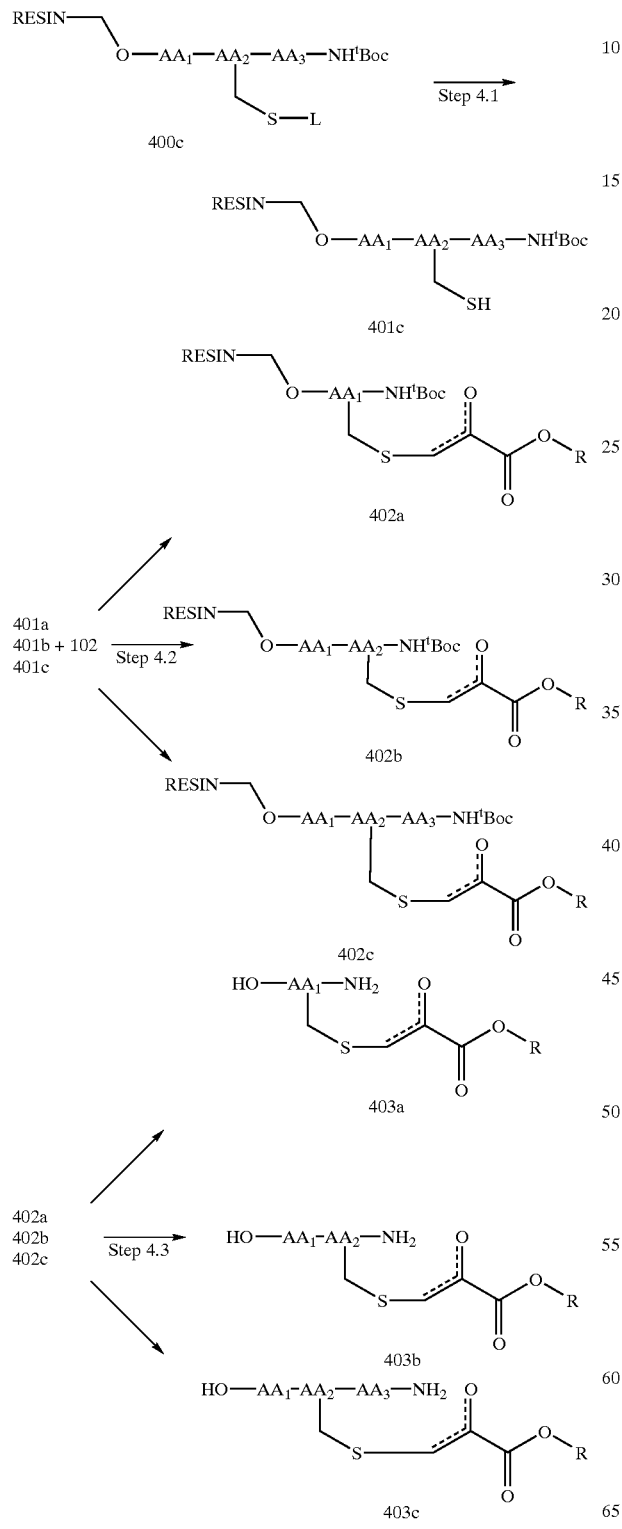

Reaction Scheme 4 describes a synthetic route to the peptide-pyruvate conjugates starting from N-'Boc-protected resin-linked peptide precursors, such as those of Formulae 206 and 209 (corresponding to starting compounds 400b and 400c). Synthesis starting from an N-'Boc-protected amino acid is illustrated with reference to compound 400a.

As in Reaction Scheme 2, the cysteine of a resin-linked peptide, such as 400a, 400b and 400c, as illustrated in Step 4.1, is de-protected by treating with dithiothreitol to give the corresponding compound of Formula 401a, 401b or 401c, followed by conjugation of the de-protected thio group with two molar equivalents of a halopyruvate of Formula 102 (Step 4.2). The resulting N-'Boc-protected resin-bound peptide-pyruvate conjugate of Formula 402a, 402b or 402c is then deprotected and cleaved from the resin under acidic conditions, e.g., with 95% TFA (aq.), isolated and then purified by typical methods (as above) to give the corresponding free peptide-pyruvate conjugate of Formula 403a, 403b or 403c.

Reaction Scheme 5

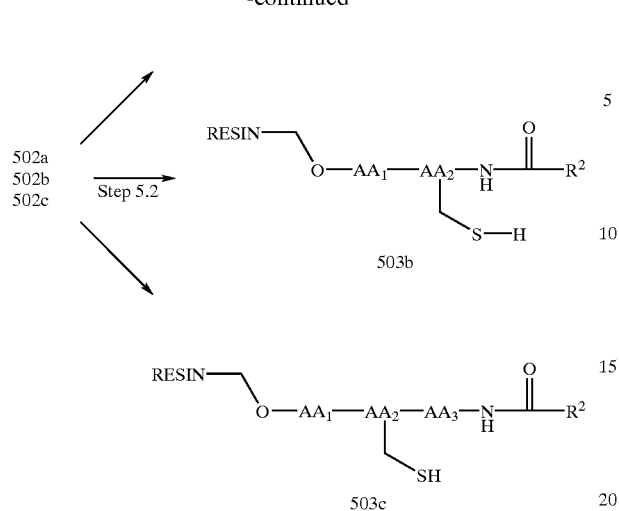

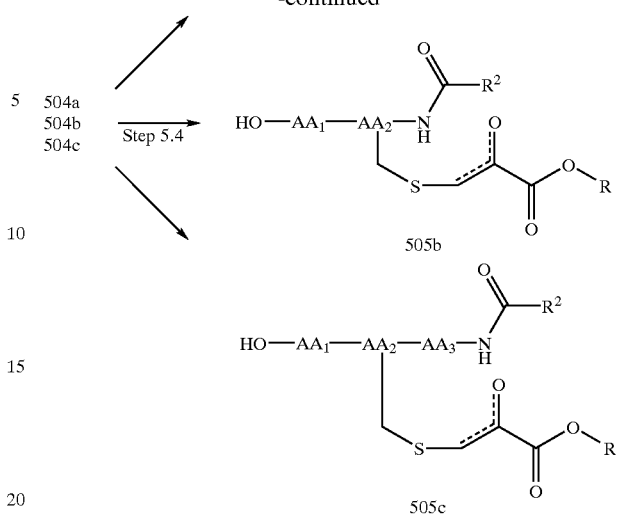

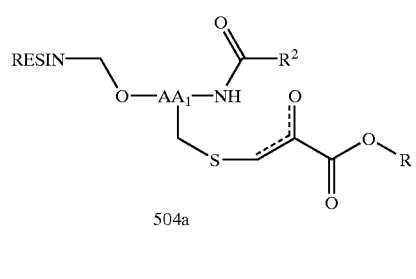

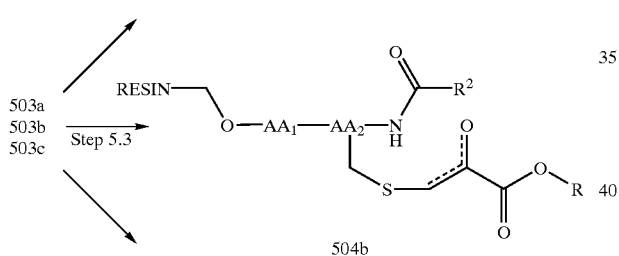

Reaction Scheme 5 illustrates the coupling of various structural moieties onto the amino group of the peptide-pyruvate conjugates of the invention, utilizing solid phase support synthesis. These compounds are further described with reference to Examples 23–27.

As illustrated in Step 5.1, starting from previously N-Fmoc-protected resin-linked peptide precursors, such as those of Formulae 204, 207 and 210 (corresponding to starting compounds 500a, 500b and 500c), coupling of a diphenol acid 501 to the amino group of the pyruvate-peptide is effected by using pre-activated HOBt ester (using DIC as a dehydrating agent) to give the corresponding compounds of Formulae 502a, 502b, and 502c. The thio protecting group is then removed (Step 5.2), followed by pyruvate conjugation (Step 5.3), cleavage, isolation and purification (Step 5.4) as described above with regard to Reaction Scheme 3 to give the corresponding compounds of the invention identified as Formulae 505a, 505b and 505c.

Reaction Scheme 6

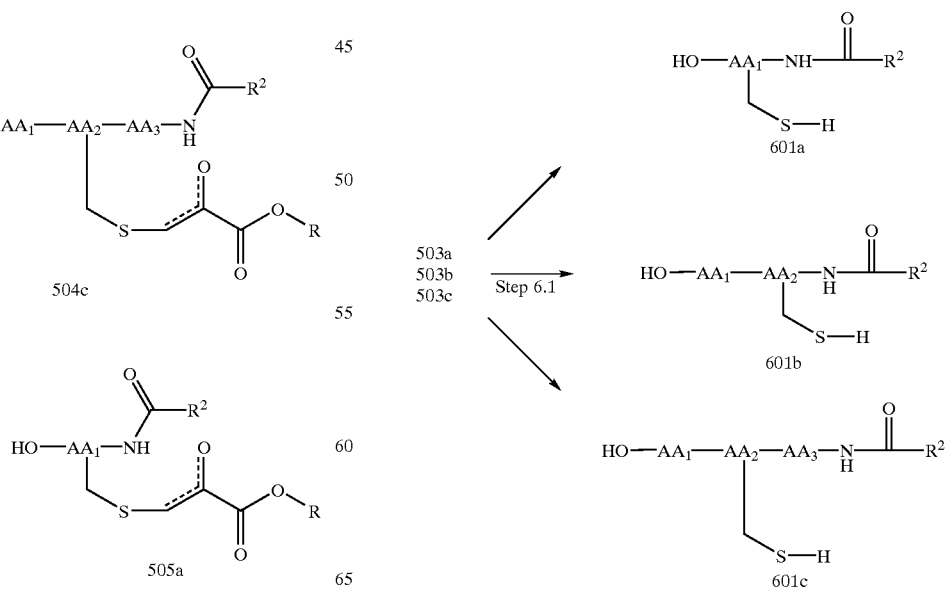

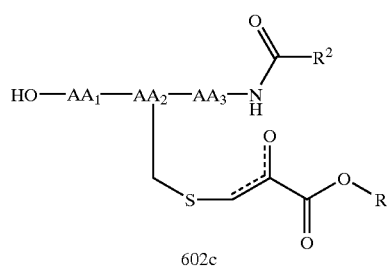
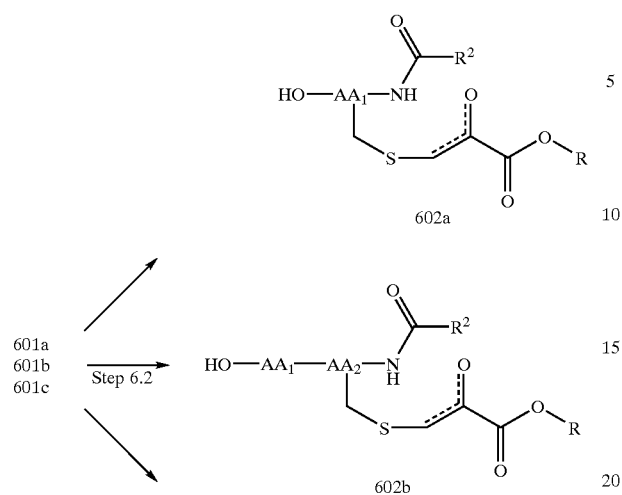

Reaction Scheme 6 illustrates an alternative sequence for coupling structural moieties onto the amino group of the peptide-pyruvate conjugates of the invention, beginning with cleavage of a precursor (here a diphenol acid coupled compound of Formula 503a, 503b or 503c) from the resin (Step 6.1), followed by pyruvate coupling, isolation and purification (Step 6.2). These reactions are carried out under conditions similar to the respective steps in Reaction Scheme 5.

Reaction Scheme 7

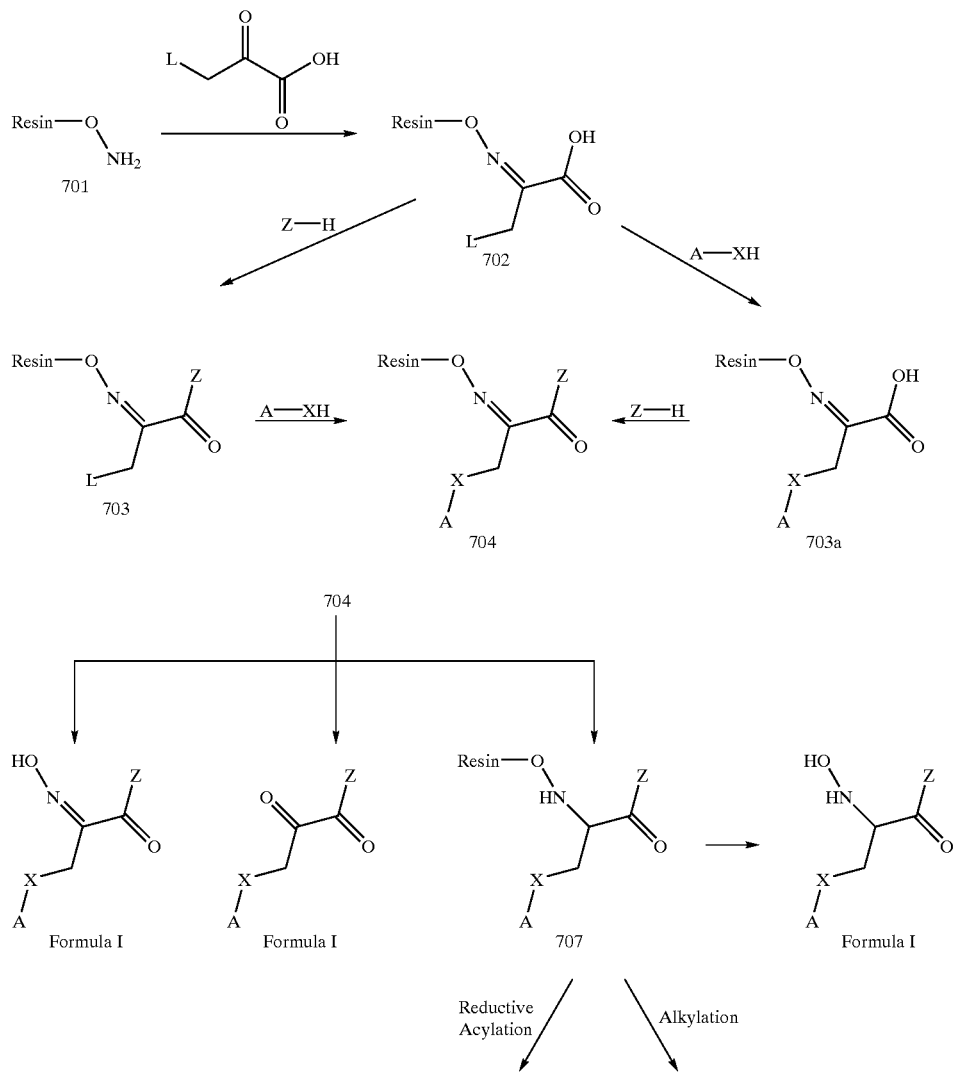

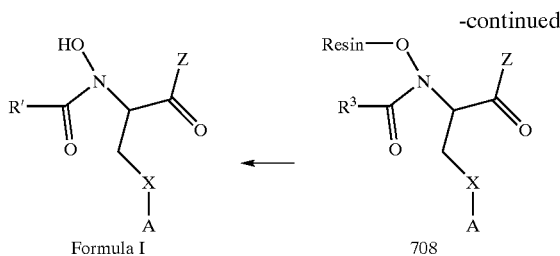
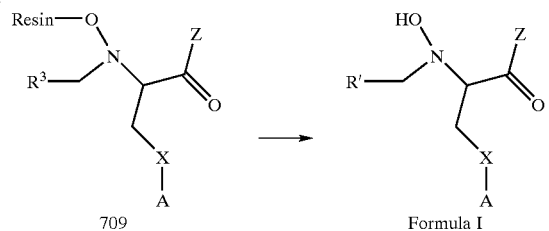

-continued

Formula I      708      709      Formula I

An alternative solid supported approach for the synthesis of compounds of Formula I is illustrated with respect to Reaction Scheme 7.

Preferred Processes and Last Steps

The preferred process for generating compounds of Formula Ia, Ib, Ic and III is solution phase reaction, e.g., as exemplified for the synthesis of Example 1–16. This process represents a simple and direct synthetic route in which the A-X in Scheme 1 is readily available. A preferred process for the preparation of compounds, particularly of Formula II, is the solid phase supported synthesis approach, e.g., as exemplified in the synthesis of Examples 16, and 19 to 27. It allows for the synthesis of structure-defined and more complex conjugates. This particularly allows for preparation of a large number of structurally diverse molecules using a parallel approach, but would not be preferred for the synthesis of large amounts of a particular compound.

Thus, in one preferred aspect, a bromopyruvate and a thio-containing nucleophile are contacted and subjected to conditions for nucleophilic substitution.

In another preferred aspect, a solid phase supported pyruvate conjugate is cleaved from the support.

In still another preferred aspect, a solid support-free cystein-containing peptide is conjugated with a bromopyruvate.

A compound of Formula I is contacted with a pharmaceutically acceptable acid to form the corresponding acid addition salt.

A pharmaceutically acceptable acid addition salt of Formula I is contacted with a base to form the corresponding free base of Formula I.

Preferred Compounds

In a preferred embodiment where A is a natural or substituted amino acid or peptide, A is selected from the group: Ala, Asn, Asp, Cys, Gln, Glu, Gly, Lys, Met, Ser and Thr, especially Ala, Asp, Cys, Glu and Gly. Further preferred are those compounds where A is a natural or substituted di- or tri-peptide, especially natural peptides. Most preferred is the tri-peptide Glu-Cys-Gly.

In another preferred embodiment, A is an optionally substituted heteroaryl group, especially a nitrogen-containing optionally substituted heteroaryl, and particularly where A is selected from the group: imidazole, triazole, thiadiazole, oxadiazole, benzoselenazole, benzoimidazole and benzothiazole.

Further preferred in each of the foregoing embodiments are those compounds where X is —S— or a covalent bond.

With overall regard to Formulae I, Ia, Ib and Ic, preferred are those compounds, pharmaceutical formulations, methods of treatment and the manufacture of medicaments having the following combinations and permutations of substituent groups (sub-grouped, respectively, in increasing order of preference, each sub-grouping being intended as combinable with other sub-groupings):

A is optionally substituted alkyl, optionally substituted aryl, optionally substituted aralkyl, optionally substituted heteroaryl, optionally substituted heterocyclyl, optionally substituted heterocycloalkyl, an optionally substituted amino acid, or an optionally substituted di-, tri- or tetra-peptide.

Particularly where A is: an optionally substituted amino acid selected from Ala, Asp, Cys, Glu and Gly, or an optionally substituted di- or tri-peptide the amino acids of which are selected from Ala, Asp, Cys, Glu and Gly. Preferably where A is the tri-peptide Glu-Cys-Gly.

More preferably where X is a covalent bond to the sulfur atom of Cys.

Preferably where A is substituted alkyl selected from: —CH$_2$—CH(OH)—CH$_2$—OH, and —CH(CH$_3$)—C(O)—N(H)—CH$_2$—COOH); optionally substituted heteroaryl selected from: benzoselenazol-2-yl, 5-(chloro or methoxy)-substituted-1H-benzoimidazol-2-yl, and 5-(chloro, methoxy or nitro)-substituted-benzothiazol-2-yl; heterocyclyl selected from: 4,5-dihydro-thiazol-2-yl, 2-thioxo-imidazolidin-1-yl and morpholino; or an optionally substituted di-, tri- or tetra-peptide.

Particularly where X is —S— or or a covalent bond to the sulfur atom of Cys or to the nitrogen atom of optionally substituted heterocyclyl.

Particularly where W is =O or =N—OR$^a$.

Particularly where Z is —OR or —N$^b$R$^c$.

W is =O or =N—OR$^a$.

Particularly where Z is —OR or —N$^b$R$^c$.

Particularly where W is =O and Z is —OR

Preferably where R is hydrogen or C$_1$ to C$_8$ alkyl.

More preferably where R is hydrogen, ethyl or n-butyl.

Preferably where A is substituted alkyl selected from: —CH$_2$—CH(OH)—CH$_2$—OH, and —CH(CH$_3$)—C(O)—N(H)—CH$_2$—COOH); optionally substituted heteroaryl selected from: benzoselenazol-2-yl, 5-(chloro or methoxy)-substituted-1H-benzoimidazol-2-yl, and 5-(chloro, methoxy or nitro)-substituted-benzothiazol-2-yl; heterocyclyl selected from: 4,5-dihydro-thiazol-2-yl, 2-thioxo-imidazolidin-1-yl and morpholino; or an optionally substituted di-, tri- or tetra-peptide.

More preferably where X is —S— or or a covalent bond to the sulfur atom of Cys or to the nitrogen atom of optionally substituted heterocyclyl.

Most preferably where R is hydrogen or C$_1$ to C$_8$ alkyl.

Preferably where X is —S— or or a covalent bond to the sulfur atom of Cys or to the nitrogen atom of optionally substituted heterocyclyl.

Particularly where W is =O and Z is —NR$^b$R$^c$.
  Preferably where R$^b$ and R$^c$ are C$_1$ to C$_4$ alkyl.
  Preferably where R$^b$ is C$_1$ to C$_8$ optionally acyl-substituted alkyl, optionally substituted aryl, optionally substituted aralkyl or cycloalkyl, and R$^c$ is hydrogen.
  Preferably where R$^b$ and R$^c$ together with the nitrogen to which they are attached form a 2-optionally substituted-pyrrolidine ring or a 6-membered ring selected from 4-optionally substituted-piperidin-1-yl and morpholin-4-yl.
Particularly where W is =N—OR$^a$.
  Preferably where R$^a$ is hydrogen, C$_1$ to C$_4$alkyl or alkenyl, phenyl or optionally substituted benzyl.
  Preferably where Z is —OR or —NR$^b$R$^c$.
    More preferably where R is hydrogen or C$_1$ to C$_8$ alkyl.
      Most preferably where R is hydrogen, ethyl or n-butyl.
  Preferably where Z is —NR$^b$R$^c$.
    More preferably where R$^b$ and R$^c$ are C$_1$ to C$_4$ alkyl.
    More preferably where R$^b$ is C$_1$ to C$_8$ optionally acyl-substituted alkyl, optionally substituted aryl, optionally substituted aralkyl or cycloalkyl, and R$^c$ is hydrogen.
    More preferably where R$^b$ and R$^c$ together with the nitrogen to which they are attached form a 2-optionally substituted-pyrrolidine ring or a 6-membered ring selected from 4-optionally substituted-piperidin-1-yl and morpholin-4-yl.
  Preferably where A is substituted alkyl selected from: —CH$_2$—CH(OH)—CH$_2$—OH, and —CH(CH$_3$)—C(O)—N(H)—CH$_2$—COOH); optionally substituted heteroaryl selected from: 5-(chloro or methoxy)-substituted-1H-benzoimidazol-2-yl, and 5-(chloro, methoxy or nitro)-substituted-benzothiazol-2-yl; heterocyclyl selected from: 4,5-dihydro-thiazol-2-yl, 2-thioxo-imidazolidin-1-yl and morpholino; or an optionally substituted di-, tri- or tetra-peptide.
    More preferably where X is —S— or or a covalent bond to the sulfur atom of Cys or to the nitrogen atom of optionally substituted heterocyclyl.
Z is —OR or —NR$^b$R$^c$.
  Especially where R is hydrogen or C$_1$ to C$_8$ alkyl.
    Particularly where R is hydrogen, ethyl or n-butyl.
  Especially where R$^b$ and R$^c$ are C$_1$ to C$_4$ alkyl.
  Especially where R$^b$ is C$_1$ to C$_8$ optionally acyl-substituted alkyl, optionally substituted aryl, optionally substituted aralkyl or cycloalkyl, and R$^c$ is hydrogen.
  Especially where R$^b$ and R$^c$ together with the nitrogen to which they are attached form a 2-optionally substituted-pyrrolidine ring or a 6-membered ring selected from 4-optionally substituted-piperidin-1-yl and morpholin-4-yl.
Especially where W is =N—OR$^a$.
Especially where Z is —NR$^b$R$^c$.
  Particularly where W is =N—OR$^a$.
    Preferably where R$^b$ is: C$_1$ to C$_4$ alkyl, optionally substituted aryl, optionally substituted aralkyl or cycloalkyl; and
    Preferably where R$^c$ is: hydrogen or C$_1$ to C$_4$ alkyl; or
    Preferably where R$^b$ and R$^c$ together with the nitrogen to which they are attached form an optionally substituted-pyrrolidine ring a 6-membered ring, optionally incorporating O or N as an additional ring heteroatom, and said ring being optionally substituted with one substituent selected from the group consisting of acyl and optionally substituted alkyl.

With regard to Formula II, preferred are those compounds, pharmaceutical formulations, methods of treatment and the manufacture of medicaments having the following combinations and permutations of substituent groups (sub-grouped, respectively, in increasing order of preference, each sub-grouping being intended as combinable with other sub-groupings):
R$^1$ is: —C(O)—O—R'
  Especially where R' is hydrogen or lower alkyl.
  Especially where R$^2$ is hydrogen.
  Especially where R$^3$ is —CH$_2$—S—CH$_2$—C(W)—C(O)-Z, —CH$_2$—S—CH=C(OH)—C(O)-Z, —CH$_2$—S(O)—CH$_2$—C(W)—C(O)-Z, or —CH$_2$—S(O)—CH=C(OH)—C(O)-Z.
    Particularly where W is =O or =N—OR$^a$.
      Preferably where R$^a$ is hydrogen or alkyl;
    Particularly where Z is —OR or —NR$^b$R$^a$.
      Preferably where R is hydrogen, optionally substituted alkyl, optionally substituted cycloalkyl, optionally substituted aryl, or optionally substituted aralkyl.
      Preferably where R$^b$ is C$_1$ to C$_4$ alkyl, phenyl or benzyl;.
      Preferably where R$^c$ is hydrogen or C$_1$ to C$_4$ alkyl.
      Preferably where R$^b$ and R$^c$ together with the nitrogen to which they are attachwed form a 6-membered ring selected from 4-optionally substituted-piperidin-1-yl and morpholin-4-yl.
  Especially where R$^4$ is hydrogen.
  Especially where R$^5$ is hydrogen or lower alky.
  Especially where k, m and n are respectively: 0,2,1; 1,0,1; or 2,0,1.

With regard to Formula II, preferred are those compounds, pharmaceutical formulations, methods of treatment and the manufacture of medicaments having the following combinations and permutations of substituent groups (sub-grouped, respectively, in increasing order of preference, each sub-grouping being intended as combinable with other sub-groupings):
R$^{3.1}$ is hydrogen
  Especially where R$^{3.2}$ is hydrogen or ethyl.
    Particularly where R$^{3.3}$ and R$^{3.4}$ are both H or are both methyl.
      Preferably where R$^{3.5}$ is: COOH.
  Especially where R$^{3.3}$ and R$^{3.4}$ are both H or are both methyl.
  Especially where R$^{3.5}$ is: COOH.
R$^{3.2}$ is hydrogen or ethyl.
  Especially where R$^{3.3}$ and R$^{3.4}$ are both H or are both methyl.
  Especially where R$^{3.5}$ is: COOH.
R$^{3.3}$ and R$^{3.4}$ are both H or are both methyl
  Especially where R$^{3.5}$ is: COOH.
R$^{3.5}$ is: COOH.

In the methods of treatment and the manufacture of medicaments employing compounds according to Formula I, preferred are those compounds the substituents of which are selected from the following groups:
A is: optionally substituted alkyl, optionally substituted aryl, optionally substituted aralkyl, optionally substituted heteroaryl, optionally substituted heterocyclyl, optionally substituted heterocycloalkyl, an optionally substituted amino acid, or an optionally substituted di-, tri- or tetra-peptide;

X is: —N(H)—, —S—, or a covalent bond to the sulfur atom of Cys or to the nitrogen atom of optionally substituted heterocyclyl;

W is: =O or =N—OR$^a$;

Z is: —OR, or —NE$^b$R$^a$;

R is: hydrogen, optionally substituted alkyl, substituted cycloalkyl, or optionally substituted aralkyl;

R$^a$ is: hydrogen, optionally substituted alkyl, optionally substituted aryl, or optionally substituted aralkyl;

R$^b$ is: hydrogen, optionally substituted alkyl, optionally substituted aryl, optionally substituted aralkyl or optionally substituted cycloalkyl;

R$^c$ is: hydrogen or optionally substituted alkyl; and

R$^b$ and R$^c$ together with the nitrogen to which they are attached may form a 5- or 6-membered ring, optionally incorporating N or O as an additional ring heteroatom, and said ring being optionally substituted with one substituent selected from the group consisting of acyl and optionally substituted alkyl.

More preferably, the above substituents of Formula I are further selected from the following groups:

A is: the tri-peptide Glu-Cys-Gly; and

X is: a covalent bond to the sulfur atom of Cys.

R is: hydrogen or $C_1$ to $C_8$ alkyl;

R$^a$ is: hydrogen, $C_1$ to $C_8$ alkyl or alkenyl, phenyl or aralkyl;

R$^b$ is: $C_1$ to $C_8$ optionally acyl-substituted alkyl, optionally substituted aralkyl or cycloalkyl; and R$^c$ is: hydrogen or $C_1$ to $C_4$ alkyl; or R$^b$ and R$^c$ together with the nitrogen to which they are attached form a 5-membered ring, or a 6-membered ring optionally incorporating O as an additional ring heteroatom, and said ring being optionally substituted with one substituent selected from the group consisting of acyl and optionally substituted alkyl.

With regard to Formula Ia, preferred are those compounds the substituents of which are selected from the following groups:

A is: substituted alkyl selected from: —CH$_2$—CH(OH)—CH$_2$—OH, —CH(CH$_3$)—CH(OH)—CH$_2$—OH, —CH(CH$_3$)—C(O)—N(H)—CH$_2$—COOH, —CH$_2$—C(O)—N(H)—CH$_2$—COOH, —CH$_2$—CH$_2$—C(O)—N(H)—CH$_2$—COOH, —CH(CH$_3$)—CH$_2$—C(O)—N(H)—CH$_2$—COOH, and —CH$_2$—CH(CH$_3$)—C(O)—N(H)—CH$_2$—COOH, substituted heteroaryl selected from: 5-chloro-1H-benzoimidazol-2-yl, 5-methoxy-1H-benzoimidazol-2-yl, 4-oxo-3,4-dihydro-quinazolin-2-yl, benzoselenazol-2-yl, and 5-substituted-benzothiazol-2-yl, heterocyclyl selected from: thiazol, 2-thioxo-imidazolidin-1-yl and morpholino, or an optionally substituted di-, tri- or tetra-peptide;

R is: hydrogen, optionally substituted alkyl, or optionally substituted cycloalkyl;

X is: —S—, —S(O)—, —S(O)$_2$—, or a covalent bond to the sulfur atom of Cys or to the nitrogen atom of optionally substituted heterocyclyl; and Z is: —OR.

More preferably, the above substituents of Formula Ia are further selected from the following groups:

A is: an optionally substituted di- or tri-peptide the amino acids of which are selected from Ala, Asp, Cys, Glu and Gly; most preferably the tri-peptide Glu-Cys-Gly;

X is: —S—, or a covalent bond to the sulfur atom of Cys or to the nitrogen atom of optionally substituted heterocyclyl; and R is: hydrogen or $C_1$ to $C_8$ alkyl.

With regard to Formula Ib, preferred are those compounds the substituents of which are selected from the following groups:

A is: optionally substituted aryl, optionally substituted heteroaryl, optionally substituted heterocyclyl, an optionally substituted amino acid, or an optionally substituted di-, tri- or tetra-peptide;

R is: hydrogen, optionally substituted alkyl, substituted cycloalkyl, or optionally substituted aralkyl;

R$^a$ is: hydrogen, optionally substituted alkyl, optionally substituted aryl, or optionally substituted aralkyl;

X is: —S—, or a covalent bond to the sulfur atom of Cys or to the nitrogen atom of optionally substituted heterocyclyl; and Z is: —OR.

More preferably, the above substituents of Formula Ib are further selected from the following groups:

A is: phenyl or optionally substituted heteroaryl selected from: 5-optionally substituted-benzothiazol-2-yl and 5-optionally substituted benzoimidazol-2-yl, or an optionally substituted di- or tri-peptide the amino acids of which are selected from Ala, Asp, Cys, Glu and Gly; most preferably the tri-peptide Glu-Cys-Gly;

R$^a$ is: hydrogen, $C_1$ to $C_4$alkyl or alkenyl, phenyl or optionally substituted benzyl; and R is: hydrogen or $C_1$ to $C_6$ alkyl.

With regard to Formula Ic, preferred are those compounds the substituents of which are selected from the following groups:

A is: optionally substituted alkyl, optionally substituted aryl, optionally substituted aralkyl, optionally substituted heteroaryl, optionally substituted heterocyclyl, optionally substituted heterocycloalkyl, an optionally substituted amino acid, or an optionally substituted di-, tri- or tetra-peptide;

X is: —S—, or a covalent bond to the sulfur atom of Cys;

W is: =O or =N—OR$^a$;

R$^a$ is: hydrogen, optionally substituted alkyl, optionally substituted aryl, or optionally substituted aralkyl;

R$^b$ is: hydrogen, optionally substituted alkyl, optionally substituted aryl, optionally substituted aralkyl or optionally substituted cycloalkyl;

R$^c$ is: hydrogen or optionally substituted alkyl; and

R$^b$ and R$^c$ together with the nitrogen to which they are attached may form a 5- or 6-membered ring, optionally incorporating N or O as an additional ring heteroatom, and said ring being optionally substituted with one substituent selected from the group consisting of acyl and optionally substituted alkyl.

More preferably, the above substituents of Formula Ic are further selected from the following groups:

A is: optionally substituted aryl selected from: phenyl and p-tolyl; or optionally substituted heteroaryl selected from: 5-optionally substituted-benzothiazol-2-yl and 5-optionally substituted benzoimidazol-2-yl, or an optionally substituted di- or tri-peptide the amino acids of which are selected from Ala, Asp, Cys, Glu and Gly; most preferably the tri-peptide Glu-Cys-Gly;

W is =O, =N—OH, or =N—O—CH$_3$; and

R$^b$ and R$^c$ are C$_1$ to C$_4$ alkyl;

R$^b$ is C$_1$ to C$_8$ optionally acyl-substituted alkyl, optionally substituted aryl, optionally substituted aralkyl or cycloalkyl, and R$^c$ is hydrogen; or R$^b$ and R$^c$ together with the nitrogen to which they are attached form a 2-optionally substituted-pyrrolidine ring or a 6-membered ring selected from 4-optionally substituted-piperidin-1-yl and morpholin-4-yl.

With regard to Formula II, preferred are those compounds the substituents of which are selected from the following groups:

R$^1$ is: —C(O)—O—R' where R' is hydrogen or lower alkyl;

R$^2$ is: hydrogen;

R$^3$ is: —CH$_2$—S—CH$_2$—C(W)—C(O)-Z, —CH$_2$—S—CH=C(OH)—C(O)-Z, —CH$_2$—S(O)—CH$_2$—C(W)—C(O)-Z, or —CH$_2$—S(O)—CH=C(OH)—C(O)-Z

R$^4$ is: hydrogen;

R$^5$ is hydrogen or lower alkyl;

W is: =O or =N—OR$^a$;

Z is: —OR or —NR$^b$R$^c$;

R is: hydrogen, optionally substituted alkyl, optionally substituted cycloalkyl, optionally substituted aryl, or optionally substituted aralkyl;

R$^a$ is: hydrogen or alkyl;

R$^b$ is C$_1$ to C$_4$ alkyl, phenyl or benzyl;

R$^c$ is: hydrogen or C$_1$ to C$_4$ alkyl, or

R$^b$ and R$^c$ together with the nitrogen to which they are attachwed form a 6-membered ring selected from 4-optionally substituted-piperidin-1-yl and morpholin-4-yl; and k, m and n are respectively: 0,2,1; 1,0,1; or 2,0,1.

More preferably, the above substituents of Formula II are further selected from the following groups:

R$^1$ is: —COOH;

R$^5$ is: hydrogen; and k, m and n are respectively: 0,2,1; or 2,0,1.

With regard to Formula II, preferred are those compounds the substituents of which are selected from the following groups:

R$^{3.1}$ is hydrogen;

R$^{3.2}$ is hydrogen or ethyl;

R$^{3.3}$ and R$^{3.4}$ are both H or are both methyl; and

R$^{3.5}$ is: COOH.

More preferably, the above substituents of Formula III are further selected where R$^{3.2}$ is ethyl.

One series of preferred compounds includes the following, as well as their stereoisomers, tautomers, salts, and mixtures thereof:

3-(1H-Benzoimidazol-2-ylsulfanyl)-2-oxo-propionic acid ethyl ester 3-(5-Methyl-1H-benzoimidazol-2-ylsulfanyl)-2-oxo-propionic acid ethyl ester 3-(5-Methoxy-1H-benzoimidazol-2-ylsulfanyl)-2-oxo-propionic acid ethyl ester 3,4-Dihydro-2H-[1,4]thiazine-3,5-dicarboxylic acid 5-ethyl ester 1-(2-Carboxy-2-oxo-ethyl)-4-[2-(3,4-dihydroxy-phenyl)-vinyl]-pyridinium; bromide 3-(4,5-Dihydro-1H-imidazol-2-ylsulfanyl)-2-oxo-propionic acid ethyl ester 2-Hydroxy-3-(1H-imidazol-2-ylsulfanyl)-5-oxo-hex-2-enedioic acid diethyl ester 3-[2-Amino-9-(3,4-dihydroxy-5-hydroxymethyl-tetrahydro-furan-2-yl)-9H-purin-6-ylsulfanyl-2-oxo-propionic acid ethyl ester 2-Oxo-3-(5-sulfo-1H-benzoimidazol-2-ylsulfanyl)-propionic acid ethyl ester 3-(5-Amino-2H-[1,2,4]triazol-3-ylsulfanyl)-2-oxo-propionic acid ethyl ester 3-(5-Amino-[1,3,4]thiadiazol-2-ylsulfanyl)-2-oxo-propionic acid ethyl ester 3-(5-Nitro-1H-benzoimidazol-2-ylsulfanyl)-2-oxo-propionic acid ethyl ester 2-Oxo-3-(5-phenyl-[1,3,4]oxadiazol-2-ylsulfanyl)-propionic acid ethyl ester 3,4-Dihydro-2H-[1,4]thiazine-3,5-dicarboxylic acid 2-Amino-4-[1-(carboxymethyl-carbamoyl)-2-(2-carboxy-2-oxo-ethylsulfanyl)-ethylcarbamoyl]-butyric acid 2-Amino-N-[1-(carboxymethyl-carbamoyl)-2-(2-ethoxycarbonyl-2-oxo-ethylsulfanyl)-ethyl]-succinamic acid 3-[2-(4-Amino-4-carboxy-butyrylamino)-2-(carboxymethyl-carbamoyl)-ethylsulfanyl]-2-hydroxy-acrylic acid 3-[2-(4-Amino4-carboxy-butyrylamino)-2-(carboxymethyl-carbamoyl)-ethylsulfanyl]-2-hydroxy-acrylic acid ethyl ester 2-Amino-4-[2-(2-ethoxycarbonyl-2-oxo-ethylsulfanyl)-1-(methoxycarbonylmethyl-carbamoyl)-ethylcarbamoyl]-butyric acid methyl ester 2-Amino-4-[1-(carboxymethyl-carbamoyl)-2-(2-decyloxycarbonyl-2-oxo-ethylsulfanyl)-ethylcarbamoyl]-butyric acid 3-[2-(3-Amino-3-carboxy-propionylamino)-2-(carboxymethyl-carbamoyl)-ethylsulfanyl]-2-hydroxy-acrylic acid ethyl ester 3-{2-Amino-2-[1-(carboxymethyl-carbamoyl)-2-(2-ethoxycarbonyl-2-hydroxy-vinylsulfanyl)-ethylcarbamoyl]-ethylsulfanyl}-2-hydroxy-acrylic acid ethyl ester 3-[2-(2-Amino-3-mercapto-propionylamino)-2-(carboxymethyl-carbamoyl)-ethylsulfanyl]-2-hydroxy-acrylic acid ethyl ester 4-Amino-4-[1-(carboxymethyl-carbamoyl)-2-(2-ethoxycarbonyl-2-oxo-ethylsulfanyl)-ethylcarbamoyl]-butyric acid 1-(Carboxymethyl-carbamoyl)-2-(2-ethoxycarbonyl-2-oxo-ethylsulfanyl)-ethylcarbamoyl]-2-{4-[2-(3,4-dihydroxy-phenyl)-vinyl]-benzoylamino}-butyric acid 4-[1-(Carboxymethyl-carbamoyl)-2-mercapto-ethylcarbamoyl]-2-{4-[2-(3,4-dihydroxy-phenyl)-vinyl]-benzoylamino}-butyric acid 4-[1-(Carboxymethyl-carbamoyl)-2-(2-ethoxycarbonyl-2-oxo-ethylsulfanyl)-ethylcarbamoyl]-2-[3-(6-hydroxy-2,7,8-trimethyl-chroman-2-yl)-propionylamino]-butyric acid 4-[1-(Carboxymethyl-carbamoyl)-2-mercapto-ethylcarbamoyl]-2-[3-(6-hydroxy-2,7,8-trimethyl-chroman-2-yl)-propionylamino]-butyric acid 3-(5-Methyl-[1,3,4]thiadiazol-2-ylsulfanyl)-2-oxo-propionic acid ethyl ester 3-(5-Chloro-benzothiazol-2-ylsulfanyl)-2-oxo-propionic acid ethyl ester 3-(4,5-Dihydro-thiazol-2-ylsulfanyl)-2-oxo-propionic acid ethyl ester 2-Hydroxy-4-(1-methyl-1H-imidazol-2-ylsulfanyl)-2,3-dihydro-furan-2,5-dicarboxylic acid diethyl ester 2,2-Dimethyl-3,4-dihydro-2H-[1,4]thiazine-3,5-dicarboxylic acid 4-[2-[2-(Adamantan-1-ylmethoxycarbonyl)-2-oxo-ethylsulfanyl]-1-(carboxymethyl-carbamoyl)-ethylcarbamoyl]-2-amino-butyric acid 1-[3-(2-Ethoxycarbonyl-2-oxo-ethylsulfanyl)-2-methyl-propionyl]-pyrrolidine-2-carboxylic acid 2-Amino-3-[1-(2-ethoxycarbonyl-2-oxo-ethyl)-1H-imidazol-4-yl]-propionic acid 3-[5-(2-Ethoxycarbonyl-2-oxo-ethylsulfanyl)-[1,3,4]thiadiazol-2-ylsulfanyl]-2-oxo-propionic acid ethyl ester 2-Oxo-3-(3-phenyl-[1,2,4]oxadiazol-5-ylsulfanyl)-propionic acid ethyl ester 3-(6-Ethoxy-benzothiazol-2-ylsulfanyl)-2-oxo-propionic acid ethyl ester 2-Oxo-3-(9H-purin-6-ylsulfanyl)-propionic acid ethyl ester 3-[9-(3,4-Dihydroxy-5-hydroxymethyl-tetrahydro-furan-2-yl)-9H-purin-6-ylsulfanyl]-2-oxo-propionic acid ethyl ester 2-Acetylamino-3-(2-ethoxycarbonyl-2-oxo-ethylsulfanyl)-propionic acid 3-Amino-N-[1-(carboxymethyl-carbamoyl)-2-(2-ethoxycarbonyl-2-oxo-ethylsulfanyl)-ethyl]-succinamic acid 2-[2-Amino-3-(2-ethoxycarbonyl-2-oxo-ethylsulfanyl)-propionylamino]-3-(2-ethoxycarbonyl-2-oxo-ethylsulfanyl)-propionic acid 2-[2-(4-Amino-4-carboxy-butyrylamino)-3-(2-ethoxycarbonyl-2-oxo-ethylsulfanyl)-propionylamino]-4-methylsulfanyl-butyric acid 2-Amino-4-[1-[1-carboxy-2-(1H-imidazol-4-yl)-ethylcarbamoyl]-2-(2-ethoxycarbonyl-2-oxo-ethylsulfanyl)-ethylcarbamoyl]-butyric acid 2-Amino-4-[1-(carboxymethyl-carbamoyl)-2-(2-octadecyloxycarbonyl-2-oxo-ethylsulfanyl)-ethylcarbamoyl]-butyric acid 2-Amino-4-[1-[1-carboxy-2-(1H-indol-2-yl)-ethylcarbamoyl]-2-(2-ethoxycarbonyl-2-oxo-ethylsulfanyl)-ethylcarbamoyl]-butyric acid 2-Amino-4-[1-[1-carboxy-2-(4-hydroxy-phenyl)-ethylcarbamoyl]-2-(2-ethoxycarbonyl-2-oxo-ethylsulfanyl)-ethylcarbamoyl]-butyric acid 2-[2-(4-Amino-4-carboxy-butyrylamino)-3-(2-ethoxycarbonyl-2-oxo-ethylsulfanyl)-propionylamino]-3-methyl-butyric acid 2-Amino-4-[1-(1-carboxy-ethylcarbamoyl)-2-(2-ethoxycarbonyl-2-oxo-ethylsulfanyl)-ethylcarbamoyl]-butyric acid 2-[2-(4-Amino-4-carboxy-butyrylamino)-3-(2-ethoxycarbonyl-2-oxo-ethylsulfanyl)-propionylamino]-pentanedioic acid 2-Amino-4-[1-(1-carboxy-2-hydroxy-ethylcarbamoyl)-2-(2-ethoxycarbonyl-2-oxo-ethylsulfanyl)-ethylcarbamoyl]-butyric acid 2-Amino-4-[1-[1-(carboxymethyl-carbamoyl)-2-(2-ethoxycarbonyl-2-oxo-ethylsulfanyl)-ethylcarbamoyl]-2-(2-ethoxycarbonyl-2-oxo-ethylsulfanyl)-ethylcarbamoyl]-butyric acid 2-Amino-4-[1-[1-carboxy-2-(2-ethoxycarbonyl-2-oxo-ethylsulfanyl)-ethylcarbamoyl]-2-(2-ethoxycarbonyl-2-oxo-ethylsulfanyl)-ethylcarbamoyl]-butyric acid 2-Amino-4-[1-carboxy-2-(2-ethoxycarbonyl-2-oxo-ethylsulfanyl)-ethylcarbamoyl]-butyric acid 2-Amino-4-[1-(ethoxycarbonylmethyl-carbamoyl)-2-(2-ethoxycarbonyl-2-oxo-ethylsulfanyl)-ethylcarbamoyl]-butyric acid 3-[2-Amino-2-(carboxymethyl-carbamoyl)-ethylsulfanyl]-2-oxo-propionic acid ethyl ester 2-oxo-3-(2-thioxo-imidazolidin-1-yl)-propionic acid ethyl ester 2-Amino-4-[1-(carboxymethyl-carbamoyl)-2-(2,3-dioxo-3-piperidin-1-yl-propylsulfanyl)-ethylcarbamoyl]-butyric acid 2-Amino-4-[1-(carboxymethyl-carbamoyl)-2-(3-morpholin-4-yl-2,3-dioxo-propylsulfanyl)-ethylcarbamoyl]-butyric acid 2-Amino-4-[1-(carboxymethyl-carbamoyl)-2-(2-ethylcarbamoyl-2-oxo-ethylsulfanyl)-ethylcarbamoyl]-butyric acid 2-Amino-4-[1-(carboxymethyl-carbamoyl)-2-(2,3-dioxo-3-pyrrolidin-1-yl-propylsulfanyl)-ethylcarbamoyl]-butyric acid 2-Amino-4-[1-(carboxymethyl-carbamoyl)-2-(2-octylcarbamoyl-2-oxo-ethylsulfanyl)-ethylcarbamoyl]-butyric acid 1-{3-[2-(4-Amino-4-carboxy-butyrylamino)-2-(carboxymethyl-carbamoyl)-ethylsulfanyl]-2-oxo-propionyl}-pyrrolidine-2-carboxylic acid methyl ester 2-Amino-4-[1-(carboxymethyl-carbamoyl)-2-(2-cyclohexylcarbamoyl-2-oxo-ethylsulfanyl)-ethylcarbamoyl]-butyric acid 2-Amino-4-{1-(carboxymethyl-carbamoyl)-2-[2-(1-methoxycarbonyl-2-phenyl-ethylcarbamoyl)-2-oxo-ethylsulfanyl]-ethylcarbamoyl}-butyric acid 2-Amino-4-[2-(2-benzylcarbamoyl-2-oxo-ethylsulfanyl)-1-(carboxymethyl-carbamoyl)-ethylcarbamoyl]-butyric acid 2-Amino-4-[1-(carboxymethyl-carbamoyl)-2-(2-hexylcarbamoyl-2-oxo-ethylsulfanyl)-ethylcarbamoyl]-butyric acid 2-{3-[2-(4-Amino-4-carboxy-butyrylamino)-2-(carboxymethyl-carbamoyl)-ethylsulfanyl]-2-oxo-propionylamino}-3-methyl-pentanoic acid methyl ester 2-Amino-4-[1-(carboxymethyl-carbamoyl)-2-(2-dimethylcarbamoyl-2-oxo-ethylsulfanyl)-ethylcarbamoyl]-butyric acid 2-Amino-4-(1-(carboxymethyl-carbamoyl)-2-{2-[2-(4-hydroxy-phenyl)-1-methoxycarbonyl-ethylcarbamoyl]-2-oxo-ethylsulfanyl}-ethylcarbamoyl)-butyric acid 2-Amino-4-[1-(carboxymethyl-carbamoyl)-2-(2-diethylcarbamoyl-2-oxo-ethylsulfanyl)-ethylcarbamoyl]-butyric acid 2-Amino-4-{1-(carboxymethyl-carbamoyl)-2-[2-(4-methyl-cyclohexylcarbamoyl)-2-oxo-ethylsulfanyl]-ethylcarbamoyl}-butyric acid 2-Amino-4-[1-(carboxymethyl-carbamoyl)-2-(2-ethoxycarbonyl-2-methoxyimino-ethylsulfanyl)-ethylcarbamoyl]-butyric acid 2-Amino-4-[1-(carboxymethyl-carbamoyl)-2-(2-ethoxycarbonyl-2-hydroxyimino-ethylsulfanyl)-ethylcarbamoyl]-butyric acid 2-Amino4-[1-(carboxymethyl-carbamoyl)-2-(2-ethoxycarbonyl-2-ethoxyimino-ethylsulfanyl)-ethylcarbamoyl]-butyric acid 2-Amino-4-[2-(2-tert-butoxyimino-2-ethoxycarbonyl-ethylsulfanyl)-1-(carboxymethyl-carbamoyl)-ethylcarbamoyl]-butyric acid 4-[2-(2-Allyloxyimino-2-ethoxycarbonyl-ethylsulfanyl)-1-(carboxymethyl-carbamoyl)-ethylcarbamoyl]-2-amino-butyric acid 2-Amino-4-{1-(carboxymethyl-carbamoyl)-2-[2-ethoxycarbonyl-2-(4-nitro-benzyloxyimino)-ethylsulfanyl]-ethylcarbamoyl}-butyric acid 2-Amino-4-[2-(2-benzyloxyimino-2-ethoxycarbonyl-ethylsulfanyl)-1-(carboxymethyl-carbamoyl)-ethylcarbamoyl]-butyric acid 2-Amino-4-[1-(carboxymethyl-carbamoyl)-2-(2-ethoxycarbonyl-2-phenoxyimino-ethylsulfanyl)-ethylcarbamoyl]-butyric acid Another, more preferred series of compounds includes the following as well as their stereoisomers, tautomers, salts, and mixtures thereof:

3-(1H-Benzoimidazol-2-ylsulfanyl)-2-oxo-propionic acid ethyl ester
3,4-Dihydro-2H-[1,4]thiazine-3,5-dicarboxylic acid 5-ethyl ester
3-(5-Chloro-benzothiazol-2-ylsulfanyl)-2-oxo-propionic acid ethyl ester
3-(5-Nitro-1H-benzoimidazol-2-ylsulfanyl)-2-oxo-propionic acid ethyl ester
2-oxo-3-(2-thioxo-imidazolidin-1-yl)-propionic acid ethyl ester
3-(5-Methoxy-1H-benzoimidazol-2-ylsulfanyl)-2-oxo-propionic acid ethyl ester
3-(4,5-Dihydro-thiazol-2-ylsulfanyl)-2-oxo-propionic acid ethyl ester
2-Amino-4-[1-(carboxymethyl-carbamoyl)-2-(2-carboxy-2-oxo-ethylsulfanyl)-ethylcarbamoyl]-butyric acid
2-Amino-N-[1-(carboxymethyl-carbamoyl)-2-(2-ethoxycarbonyl-2-oxo-ethylsulfanyl)-ethyl]-succinamic acid
2-Amino-4-[1-(carboxymethyl-carbamoyl)-2-(2,3-dioxo-3-piperidin-1-yl-propylsulfanyl)-ethylcarbamoyl]-butyric acid
2-Amino-4-{1-(carboxymethyl-carbamoyl)-2-[2-(1-methoxycarbonyl-2-phenyl-ethylcarbamoyl)-2-oxo-ethylsulfanyl]-ethylcarbamoyl}-butyric acid
2-Amino-4-[1-(carboxymethyl-carbamoyl)-2-(3-morpholin-4-yl-2,3-dioxo-propylsulfanyl)-ethylcarbamoyl]-butyric acid
2-Amino-4-[1-(carboxymethyl-carbamoyl)-2-(2-ethoxycarbonyl-2-methoxyimino-ethylsulfanyl)-ethylcarbamoyl]-butyric acid
2-Amino-4-[1-(carboxymethyl-carbamoyl)-2-(2-ethoxycarbonyl-2-hydroxyimino-ethylsulfanyl)-ethylcarbamoyl]-butyric acid
2-Amino-4-[2-(2-butoxycarbonyl-2-methoxyimino-ethylsulfanyl)-1-(carboxymethyl-carbamoyl)-ethylcarbamoyl]-butyric acid
2-Amino-4-[2-(2-benzyloxyimino-2-butoxycarbonyl-ethylsulfanyl)-1-(carboxymethyl-carbamoyl)-ethylcarbamoyl]-butyric acid.

Presently most preferred (particularly in the practice of the methods of the invention) is the following series of compounds including their stereoisomers, tautomers, salts, and mixtures thereof:

2-amino-4-[1-(carboxymethyl-carbamoyl)-2-(2-oxo-2-pentyloxycarbonyl-ethylsulfanyl)-ethylcarbamoyl]-butyric acid,
2-amino-4-[1-(carboxymethyl-carbamoyl)-2-(2-hexyloxycarbonyl-2-oxo-ethylsulfanyl)-ethylcarbamoyl]-butyric acid,
2-amino-4-[1-(carboxymethyl-carbamoyl)-2-(2-ethoxycarbonyl-2-oxo-ethylsulfanyl)-ethylcarbamoyl]-butyric acid,
2-amino-4-[1-(carboxymethyl-carbamoyl)-2-(2-carboxy-2-oxo-ethylsulfanyl)-ethylcarbamoyl]butyric acid,
2-amino-4-[1-(carboxymethyl-carbamoyl)-2-(2-ethoxycarbonyl-2-oxo-ethylsulfanyl)-ethylcarbamoyl] butyric acid,
2-amino-4-[2-(2-butoxycarbonyl-2-methoxyimino-ethylsulfanyl)-1-(carboxymethyl-carbamoyl)-ethylcarbamoyl]-butyric acid or the HCl salt thereof,
2-amino-4-[2-(2-benzyloxyimino-2-butoxycarbonyl-ethylsulfanyl)-1-(carboxymethyl-carbamoyl)-ethylcarbamoyl]-butyric acid or the HCl salt thereof,
2-amino-4-[1-(carboxymethyl-carbamoyl)-2-(2-ethoxycarbonyl-2-hydroxyimino-ethylsulfanyl)-ethylcarbamoyl]-butyric acid,
2-amino-4-[2-(2-butoxycarbonyl-2-hydroxyimino-ethylsulfanyl)-1-(carboxymethyl-carbamoyl)-ethylcarbamoyl]-butyric acid or the HCl salt thereof,
2-amino-4-[1-(carboxymethyl-carbamoyl)-2-(2-ethoxycarbonyl-2-methoxyimino-ethylsulfanyl)-ethylcarbamoyl]-butyric acid
2-amino-4-[2-(2-benzyloxyimino-2-ethoxycarbonyl-ethylsulfanyl)-1-(carboxymethyl-carbamoyl)-ethylcarbamoyl]-butyric acid or the HCl slat thereof,
2-amino-4-{1-(carboxymethyl-carbamoyl)-2-[2-ethoxycarbonyl-2-(4-nitro-benzyloxyimino)-ethylsulfanyl]-ethylcarbamoyl}-butyric acid,
2-amino-4-[1-(carboxymethyl-carbamoyl)-2-(2-ethoxycarbonyl-2-phenoxyimino-ethylsulfanyl)-ethylcarbamoyl]-butyric acid or the HCl salt thereof,
2-amino-4-[1-(carboxymethyl-carbamoyl)-2-(2-ethoxycarbonyl-2-ethoxyimino-ethylsulfanyl)-ethylcarbamoyl]-butyric acid or the di-HCl salt thereof,
2-amino-4-[2-(2-tert-butoxyimino-2-ethoxycarbonyl-ethylsulfanyl)-1-(carboxymethyl-carbamoyl)-ethylcarbamoyl]-butyric acid or the di-HCl salt thereof,
4-[2-(2-allyloxyimino-2-ethoxycarbonyl-ethylsulfanyl)-1-(carboxymethyl-carbamoyl)-ethylcarbamoyl]-2-amino-butyric acid or the di-HCl salt thereof,
2-Amino-4-{1-(carboxymethyl-carbamoyl)-2-[3-(4-methyl-piperidin-1-yl)-2,3-dioxo-propylsulfanyl]-ethylcarbamoyl}-butyric acid,
2-Amino-4-[1-(carboxymethyl-carbamoyl)-2-(2-hydroxyimino-3-oxo-3-piperidin-1-yl-propylsulfanyl)-ethylcarbamoyl]-butyric acid,
2-Amino-4-[1-(carboxymethyl-carbamoyl)-2-(2-diethylcarbamoyl-2-oxo-ethylsulfanyl)-ethylcarbamoyl]-butyric acid
2-Amino-4-[1-(carboxymethyl-carbamoyl)-2-(2,3-dioxo-3-piperidin-1-yl-propylsulfanyl)-ethylcarbamoyl]-butyric acid,
2-Amino-4-{1-(carboxymethyl-carbamoyl)-2-[2-(1-methoxycarbonyl-2-phenyl-ethylcarbamoyl)-2-oxo-ethylsulfanyl]-ethylcarbamoyl}-butyric acid,
2-Amino-4-[1-(carboxymethyl-carbamoyl)-2-(2-cyclohexylcarbamoyl-2-oxo-ethylsulfanyl)-ethylcarbamoyl]-butyric acid,
2-Amino-4-[2-(2-benzylcarbamoyl-2-oxo-ethylsulfanyl)-1-(carboxymethyl-carbamoyl)-ethylcarbamoyl]-butyric acid,
2-Amino-4-[1-(carboxymethyl-carbamoyl)-2-(3-morpholin-4-yl-2,3-dioxo-propylsulfanyl)-ethylcarbamoyl]-butyric acid,
2-amino-4-[1-(carboxymethyl-carbamoyl)-2-(2-ethylcarbamoyl-2-oxo-ethylsulfanyl)-ethylcarbamoyl]-butyric acid,
2-amino-4-[1-(carboxymethyl-carbamoyl)-2-(2-ethoxycarbonyl-2-methoxyimino-ethylsulfanyl)-ethylcarbamoyl]-butyric acid
2-amino-4-[1-(carboxymethyl-carbamoyl)-2-(2,3-dioxo-3-pyrrolidin-1-yl-propylsulfanyl)-ethylcarbamoyl]-butyric acid,
2-amino-4-[1-(carboxymethyl-carbamoyl)-2-(2-octylcarbamoyl-2-oxo-ethylsulfanyl)-ethylcarbamoyl]-butyric acid,
1-{3-[2-(4-amino-4-carboxy-butyrylamino)-2-(carboxymethyl-carbamoyl)-ethylsulfanyl]-2-oxo-propionyl}-pyrrolidine-2-carboxylic acid methyl ester,
2-amino-4-[1-(carboxymethyl-carbamoyl)-2-(2-hexylcarbamoyl-2-oxo-ethylsulfanyl)-ethylcarbamoyl]-butyric acid, 2-{3-[2-(4-amino-4-carboxy-butyrylamino)-2-(carboxymethyl-carbamoyl)-ethylsulfanyl]-2-oxo-propionylamino}-3-methyl-pentanoic acid methyl ester,
2-amino-4-[1-(carboxymethyl-carbamoyl)-2-(2-dimethylcarbamoyl-2-oxo-ethylsulfanyl)-ethylcarbamoyl]-butyric acid,
2-amino-4-(1-(carboxymethyl-carbamoyl)-2-{2-[2-(4-hydroxy-phenyl)-1-methoxycarbonyl-ethylcarbamoyl]-2-oxo-ethylsulfanyl}-ethylcarbamoyl)-butyric acid,
3-(1H-benzoimidazol-2-ylsulfanyl)-2-oxo-propionic acid,
2-oxo-3-(4-oxo-3,4-dihydro-quinazolin-2-ylsulfanyl)-propionic acid ethyl ester,
3-[1-(carboxymethyl-carbamoyl)-ethylsulfanyl]-2-hydroxy-acrylic acid ethyl ester,
3-(benzoselenazol-2-ylsulfanyl)-2-oxo-propionic acid ethyl ester,
3-(1H-benzoimidazol-2-ylsulfanyl)-2-oxo-propionic acid ethyl ester,
3-(5-chloro-benzothiazol-2-ylsulfanyl)-2-oxo-propionic acid ethyl ester,
3-(5-nitro-benzoimidazol-2-ylsulfanyl)-2-oxo-propionic acid ethyl ester,
3-(5-methoxy-benzoimidazol-2-ylsulfanyl)-2-oxo-propionic acid ethyl ester,
3-(4,5-dihydro-thiazol-2-ylsulfanyl)-2-oxo-propionic acid ethyl ester,
2-hydroxyimino-3-p-tolylsulfanyl-propionic acid methyl ester,
2-hydroxyimino-3-p-tolylsulfanyl-propionic acid,
2-hydroxyimino-3-p-tolylsulfanyl-propionic acid ethyl ester,
3-(5-chloro-benzothiazol-2-ylsulfanyl)-2-hydroxyimino-propionic acid ethyl ester,
2-hydroxyimino-3-(5-methoxy-1H-benzoimidazol-2-ylsulfanyl)-propionic acid ethyl ester,
3-(1H-benzoimidazol-2-ylsulfanyl)-2-hydroxyimino-propionic acid ethyl ester,
2-hydroxyimino-N-phenyl-3-p-tolylsulfanyl-propionamide, and
1-piperidin-1-yl-3-p-tolylsulfanyl-propane-1,2-dione 2-oxime.

Utility, Testing and Administration
General Utility

Compounds of the present invention are useful in treating a number of disorders, particularly those characterized by oxidative stress and/or inflammation. In particular, compounds of the present invention can be used in the treatment of ischemia including stroke, cerebral ischemia, myocardial ischemia, retinal ischemia, myocardial infarction and post-surgical cognitive dysfunction; neurodegenerative disorders including Alzheimer's, dementia and Parkinson's disease; peripheral neuropathy, including spinal cord injury, head injury and surgical trauma; inflammatory disorders including diabetes, renal disease, pre-menstrual syndrome, asthma, cardiopulmonary inflammatory disorders, heart failure (including chronic and congestive heart failure), rheumatoid arthritis, osteoarthritis, muscle fatigue and intermittent claudication; and for the preservation of allograft tissue and organs for transplantation.

Certain of the conditions characterized by oxidative stress fall within the group: myocardial ischemia, myocardial infarction, cardiopulmonary inflammatory disorders; and heart failure (including chronic and congestive heart failure); these are treated particularly with compounds of Formula I where W is =O and where Z is —OR. Another group of conditions characterized by oxidative stress includes: stroke, cerebral ischemia, retinal ischemia, post-surgical cognitive dysfunctions (e.g., following bypass surgery), peripheral neuropathy spinal chord injury, head injury and surgical trauma, and neurodegenerative disorders including Alzheimer's, dementia and Parkinson's disease; these are treated particularly with compounds of Formula I where W is =O or =N—OR$^a$ and where Z is —OR or —N$^b$R$^c$. Another grouping of diseases characterized by oxidative stress and involving inflammatory and/or autoimmune components includes: diabetes; renal disease; pre-menstrual syndrome; asthma, rheumatoid arthritis; osteoarthritis, muscle fatigue; and intermittent claudication.

Testing

This section describes how compositions incorporating compositions of the present invention are selected, using in vitro and/or in vivo animal models, for example, and used as therapeutic interventions in three exemplary indications, i.e., stroke, chronic heart failure and myocardial infarction.

Insults to the brain that disrupt its blood supply, as in ischemia, or its oxygen supply, as in hypoxia (low oxygen) or anoxia (no oxygen), rapidly cause neuronal imbalance leading to cell death (Flynn, C. J., et al., 1989, in G. Siegel et al., (Eds), *Basic Neurochemistry*, Raven Press, NY). Investigations into the cellular and molecular mechanisms that lead to neuronal damage and inflammation associated with various types of brain ischemia can be carried out using in vitro model systems, such as primary cell cultures, that retain the metabolic characteristics of neurons in vivo. The use of such cell-based models has led to advances in identification of biochemical mechanisms leading to neuronal death in conditions such as anoxia, hypoglycemia, excitotoxicity, and exposure to reactive oxygen species. Neuronal cell lines such as the pheochromocytoma cell line, PC12, are also useful models for studying the effects of oxidative stress on the structure and function of neuron-specific proteins that are expressed in the cell lines. As many neuronal cell lines do not express all the properties of genuine neurons, primary neuronal cultures are now widely used as in vitro models in which to discern the processes that occur in intact brain.

In vitro models of ischemia approximate oxygen and glucose deprivation that mimic in vivo conditions, for example, by placing neuronal cultures into large anaerobic or hypoxic chambers and exchanging culture medium with de-oxygenated and defined ionic composition media. The toxic overstimulation of neuronal glutamate receptors, especially N-methyl-D-aspartate (NMDA) receptors, contributes to hypoxic-ischemic neuronal injury (Choi, D. M., 1988, *Neuron* 1: 623–634), ischemic induction of reactive oxygen species (ROS) (Watson, B. D., et al., 1988, Ann NY Acad Sci., 59: 269–281), excessive calcium influx (Grotta, J. C., 1988, *Stroke* 19: 447–454), arachidonic acid increase (Siesjo, B. K., 1981, *J. Cereb. Blood Flow Metab.* 1: 155–186) and DNA damage (MacManus, J. P., et al, 1993, *Neurosci. Lett.*, 164: 89–92), each causing a cascade of neurodegeneration.

Primary embryonic hippocampal neuronal cells are widely recognized as useful in models of neuronal function. The hippocampus is a source of a relatively homogenous population of neurons with well-characterized properties typical of central nervous system (CNS) neurons in general. Pyramidal neurons, the principal cell type in the hippocampus, have been estimated to account for 85% to 90% of the total neuronal population (Banker and Goslin, 1998, *Culturing Nerve Cells*, 2$^{nd}$ edition. The MIT Press, Cambridge, Mass.). The hippocampus also exhibits a remarkable capacity for activity-dependent changes in synaptic function, such as long-term potentiation (Hawkins R D, Kandel E R, Siegelbaum S A. (1993) Learning to modulate transmitter release: themes and variations in synaptic plasticity [review], *Ann. Rev Neurosci.* 16:625–665.).

In experiments carried out in support of the present invention according to methods detailed in the Examples, anoxia/ischemia was induced in primary cultures of hippocampal neuronal cells, and compounds were tested for their ability to prevent cell death. Compounds found to have activity in such in vitro assays are then further tested in one or more animal models of cerebral ischemia ("stroke"), such as the middle cerebral artery occlusion (MCAO) model in rats.

Briefly, primary cultures of hippocampal neurons are used to test compounds for activity in neuronal protection. Hippocampal cultures are typically prepared from 18- to 19-day fetal rats. At this age, the generation of pyramidal neurons, which begins in the rat at about E15, is essentially complete. The brain tissue at this stage is relatively easy to dissociate, the meninges are removed readily, and the number of glial cells still is relatively modest (Park L C, Calingasan N.Y., Uchida K, Zhang H, Gibson G E. (2000) Metabolic impairment elicits brain cell type-selective changes in oxidative stress and cell death in culture. *J Neurochem* 74(1):114–124).

In order to evaluate the activity of compounds of the present invention, a test compound is assessed for its ability to protect cells against one or more standard stressors, including hypoxia, as detailed in the Examples. In general, desirable therapeutic compound candidates are effective in this model at concentrations less than about 10 mM, more preferably at concentrations, less than about 1 mM and even more preferably, less than about 100 $\mu$M. By effective, it is meant that such compounds protect at least 20%, preferably 30%, more preferably 40% and even more preferably 50% or more of the cells tested from stressor-induced death. By way of example, compounds that are effective in providing protection over a concentration a range of about 1 to 1000 $\mu$M would be expected to provide neuroprotection in vivo. Since precise values may vary depending upon the specific conditions under which the neuroprotective cell assay is carried out, it is the intent of the present disclosure to provide the foregoing criteria as guidance in the form of a benchmark against which to compare subsequently tested compounds, rather than to provide absolute concentrations at which the compounds of the present invention are considered to be effective. Typically, compounds that are found to be neuroprotective in such in vitro cell systems are then further tested in an in vivo animal model of neuroprotection, such as the rat middle cerebral artery occlusion model described below, or other appropriate models such as are well known in the art.

Cerebral ischemic insults are modeled in animals by occluding vessels to, or within, the cranium (Molinari, G. F., 1986, in H. J. M. Barnett, et al., (Eds) *Stroke: Pathophysiology, Diagnosis and Management*, Vol. 1, Churchill Livingstone, N.Y.). The rat middle cerebral artery occlusion (MCAO) model is one of the most widely used techniques to induce transient focal cerebral ischemia approximating cerebral ischemic damage in humans, e.g., those who suffer from a stroke. The middle cerebral artery used as the ischemic trigger in this model is the most affected vessel in human stroke. The model also entails a period of reperfusion, which typically occurs in human stroke victims. MCAO involving a two-hour occlusion has been found to produce the maximum size of cortical infarction obtainable without increased mortality at twenty-four hours.

Briefly, a nylon filament is implanted into the right carotid artery of the rat. To effect occlusion, the rat is anesthetized, and the filament is advanced into the internal carotid artery 18–20 mm from the point of bifurcation of internal and external arteries and a suture is tightly ligated around the filament for a period of two hours. Two hours post occlusion, animals are re-anesthetized, and the filament is removed, to allow reperfusion for the remainder of the experiment. Test drugs can be administered any time during this process—before, during or after occlusion, and can be administered by one or more of a variety of means, including but not limited to intracerebroventricular (ICV) infusion, intravenous (IV) infusion, intraperitoneal (IP) administration, as well as enteral administration (e.g., gavage). Animals are maintained normothermic during the experiment, as described in the Examples. At a pre-determined time following occlusion and reperfusion, animals are sacrificed and their brains are removed and processed for assessment of damage as measured by infarct volume. In general, compounds are considered to have activity in this model, if they provide a significant reduction in total infarct volume at a dose that is less than about 10 mg/kg, preferably less than 1 $\mu$mg/kg, more preferably less than 100 $\mu$g/kg and even more preferably less than about 1 $\mu$g/kg, when administered ICV or IV. By significant reduction of total infarct volume is meant a reduction of at least 20%, preferably at least 30%, more preferably at least 40%, and even more preferably about 50%, compared to control values.

Further validation of efficacy in neuroprotection can be assessed in functional tests, such as the grip strength test or the rotorod test. Animals treated with compounds that show neuroprotection maintain their pre-MCAO grip strength values after MCAO, as compared to untreated animals, who showed a significant reduction in grip strength, indicating loss of sensorimotor function. Likewise, animals treated with compounds that show neuroprotection also maintained their pre-MCAO rotorod activity scores after MCAO, as compared to untreated animals, who showed a significant reduction in rotorod scores, indicating loss of sensorimotor function at higher brain levels.

Similarly, primary cultures of myocytes can be used to test compounds in vitro for ability to provide protection against heart damage, resulting for example from myocardial ischemia or congestive heart failure. Preparation of myocardiocytes from neonatal rats is described in the Examples. Such cells are typically used to study molecular models of myocardial ischemia (Webster, K A, Discher, D J & Bishopric, N H. 1995. *J. Mol. Cell Cardiol.* 27:453–458; Camilleri, L, Moins, N, Papon, J, Maublant, J, Bailly, P, de Riberolles, C & Veyre, A. 1997. *Cell Biol. & Toxicol.* 13:435–444; Bielawska, A E, Shapiro, J P, Jiang, L, Melkonyan, H S, Piot, C, Wolfe, C L, Tomei, L D, Hannun, Y A & Umansky, S R. 1997. *Am. J. Pathol.* 151:1257–1263) and are therefore accepted as indicative of myoprotective activity. Exemplary stressor assays for this purpose are provided in the Examples. For example, cardiomyocytes in culture exhibit contractile ("beating") activity; each cardiomyocyte contraction is associated with a rise in intracellular calcium termed a "calcium transient". These calcium transients can be measured using Fluo-4, a fluorescent dye which exhibits large fluorescence intensity increases upon the binding of calcium. This assay is cell-based and tests the ability of potential cytoprotectant molecules to guard against ischemic damage and allow the cells to maintain their contractile function.

Further validation of compounds can be carried out in a whole organ assay, such as the isolated heart model of cardiac function. Similarly, compounds can be further validated in additional animal models of disease (e.g., diabetes, renal failure, asthma, muscle fatigue, inflammation), such as are well known in the art.

Administration

The compounds of Formula I are administered at a therapeutically effective dosage, e.g., a dosage sufficient to provide treatment for the disease states previously described. Administration of the compounds of the invention or the pharmaceutically acceptable salts thereof can be via any of the accepted modes of administration for agents that serve similar utilities.

While human dosage levels have yet to be optimized for the compounds of the invention, generally, a daily dose is from about 0.01 to 2.0 mg/kg of body weight, preferably about 0.1 to 1.5 mg/kg of body weight, and most preferably about 0.3 to 1.0 mg/kg of body weight. Thus, for administration to a 70 kg person, the dosage range would be about 0.7 to 140 mg per day, preferably about 7.0 to 105 mg per day, and most preferably about 21 to 70 mg per day. Administration can be as a single dose (e.g., as a bolus) or as an initial bolus followed by continuous infusion of the remaining portion of a complete dose over time, e.g., 1 to 7 days. The amount of active compound administered will, of course, be dependent on the subject and disease state being treated, the severity of the affliction, the manner and schedule of administration and the judgment of the prescribing physician.

In employing the compounds of this invention for treatment of the above conditions, any pharmaceutically acceptable mode of administration can be used. The compounds of Formula I can be administered either alone or in combination with other pharmaceutically acceptable excipients, including solid, semi-solid, liquid or aerosol dosage forms, such as, for example, tablets, capsules, powders, liquids, suspensions, suppositories, aerosols or the like. The compounds of Formula I can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of Formula I or a pharmaceutically acceptable salt thereof. In addition, these compositions may include other medicinal agents, pharmaceutical agents, carriers, adjuvants, and the like, including, but not limited to anticoagulants, blood clot dissolvers, permeability enhancers and slow release formulations.

Generally, depending on the intended mode of administration, the pharmaceutically acceptable composition will contain about 0.1% to 90%, preferably about 0.5% to 50%, by weight of a compound or salt of Formula I, the remainder being suitable pharmaceutical excipients, carriers, etc.

One preferred manner of administration for the conditions detailed above is oral, using a convenient daily dosage regimen, which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like. Such compositions may contain 0.01%-95% active ingredient, preferably 0.1–50%.

For a solid dosage form, the solution or suspension, in for example propylene carbonate, vegetable oils or triglycerides, is preferably encapsulated in a gelatin capsule. Such diester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

The formulation can be administered in a single unit dosage form for continuous treatment or in a single unit dosage form ad libitum when relief of symptoms is specifically required. For example, the formulation may be administered as a bolus or as a continuous intravenous infusion after onset of symptoms of stroke, myocardial infarction or chronic heart failure.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795. The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid, which will be subsequently diluted to the above percentages. Preferably the composition will comprise 0.2–2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

EXAMPLES

The following preparations and examples are given to enable those skilled in the art to more clearly understand and to practice the present invention. They should not be considered as limiting the scope of the invention, but merely as being illustrative and representative thereof.

General Characterization Methods

As reported in most cases of the following examples, Nuclear Magnetic Resonance (NMR) spectra were recorded on a Bruker Avance 300 spectrometer using tetramethyl silane (TMS) as the internal reference; mass spectra were obtained on an Agilent 110 LC/MSD instrument using either electrospray ionization (positive or negative mode) (ESI) or atmospheric pressure chemical ionization (positive or negative mode) (APCI).

Example 1

Formula Ia where A is 1H-Benzimidazole-2-yl, R is Ethyl, and X is S

A solution of 2-mercaptobenzimidazole (200 mg, 1.33 mmol) and ethyl 3-bromopyruvate (0.20 mL, 1.43 mmol) in methanol (2.5 mL) and acetone (2 mL) was shaken at 20° C. for 4 hours. The solvents were removed under the reduced pressure on a rotary evaporator. The residue was triturated with ethyl acetate. Solvent was decanted and the residue was dissolved in methylene chloride. The solution was washed with diluted aqueous sodium bicarbonate solution and water, and then dried over magnesium sulfate. Removal of the solvent gave the expected product, 3-(1H-Benzoimidazol-2-ylsulfanyl)-2-oxo-propionic acid ethyl ester (326 mg, 93%). $^1$H-NMR (CDCl$_3$, 300 MHz) δ (ppm): 7.31 (br. s, 1H), 7.24 (br s, 1H), 7.15–7.05 (m, 2H), 4.32 (q, J=7.1 Hz, 2H), 4.29 (br. s, 1H), 3.90 (br. s, 1H), 1.24 (t, J=7.1 Hz, 3H). MS (ESI): m/z 265 (M+1, 100).

Example 2

Formula Ia where A is 5-Methoxy-1H-benzimidazole-2-yl, R is Ethyl, and X is S

A solution of 2-mercapto-5-methylbenzimidazole (200 mg, 1.22 mmol) and ethyl 3-bromopyruvate (0.20 mL, 1.43 mmol) in methanol (2 mL) and acetone (3 mL) was shaken at room temperature for 4 hours. The solvents were removed under the reduced pressure on a rotary evaporator. The residue was triturated with ethyl acetate. Solvent was decanted and the residue was dissolved in methylene chloride. The solution was washed with diluted aqueous sodium bicarbonate solution and water, and then dried over magnesium sulfate. Removal of the solvent gave the expected product, 3-(5-methoxy-1H-benzoimidazol-2-ylsulfanyl)-2-oxo-propionic acid ethyl ester (300 mg, 88%). $^1$H-NMR (D$_3$COD, 300 MHz) δ (ppm): 7.19 (br. s, 1H), 7.10 and 7.04 (br. 2 s, 1H), 6.94 (d, J=8.2 Hz, 1H), 4.34 (q, J=7.1 Hz, 2H), 4.31 (br. s, 1H), 3.91 (br. s, 1H), 2.37 (br. s, 3H), 1.26 (t, J=7.1 Hz, 3H). MS (ESI): m/z 279 (M+1, 100).

Example 3

Formula Ia where A is 5-Methyl-1H-benzimidazole-2-yl, R is Ethyl, and X is S

A solution of 5-methoxy-2-benzimidazolethiol (200 mg, 1.11 mmol) and ethyl 3-bromopyruvate (0.20 mL, 1.43 mmol) in methanol (5 mL) and acetone (2 mL) was shaken at room temperature for 4 hours. The solvents were removed under the reduced pressure on a rotary evaporator. The residue was triturated with ethyl acetate. Solvent was decanted and the residue was dissolved in methylene chloride. The solution was washed with diluted aqueous sodium bicarbonate solution and water, and then dried over magnesium sulfate. Removal of the solvent gave the expected product, 3-(5-Methyl-1H-benzoimidazol-2-ylsulfanyl)-2-oxo-propionic acid ethyl ester (300 mg, 92%). $^1$H-NMR (D$_3$COD, 300 MHz) δ (ppm): 7.19 (br. s, 1H), 6.75 (br. s, 1H), 6.69 (dd, J=2.3 Hz, J=8.8 Hz, 1H), 4.30 (q, J=7.1 Hz, 2H), 4.29 (br. s, 1H), 3.93 (br. s, 1H), 3.69 (s, 3H), 1.24 (t, J=7.1 Hz, 3H). MS (ESI): m/z 295 (M+1, 100).

Example 4

Preparation of 3,4-dihydro-2H-[1,4]thiazine-3,5-dicarboxylic acid

To a solution of 1-cysteine (1.00 g, 8.25 mmol) in water (20 mL) was added ethyl 3-bromopyruvate (1.61 g, 8.25 mmol). The pH of solution was adjusted to about 4 with aqueous sodium bicarbonate solution. After stirred at room temperature for 30 minutes, the mixture was washed with methylene chloride. The aqueous phase was separated and then evaporated to dryness under lyophilization conditions. The methanol solution of the obtained residue was passed through a silica gel pack, resulting in 470 mg of pure product (32%). $^1$H-NMR (D$_3$COD, 300 MHz) δ (ppm): 6.16 (d, J=1.2 Hz, 1H), 4.23 (d, J=7.1 Hz, 2H), 3.86 (dd, J=2.7 Hz, J=8.2 Hz, 2H), 3.25–3.15 (m, 1H), 2.78 (dd, J=8.2 Hz, J=12.2 Hz, 1H), 1.30 (t, J=7.1 Hz, 3H). $^{13}$CNMR (75 Hz, D$_3$COD): δ (ppm): 177.4, 164.6, 129.9, 103.0, 62.3, 56.7, 28.8, 14.7.

Example 5

Formula Ia where A is 4-[2-(3,4-Dihydroxy-phenyl)-vinyl]-pyridinium bromide, R is H, and X is a Covalent Bond 4-Bromomethyl-1,2-bis-methoxymethoxy-benzene A suspension of triphenyl phosphine (262 mg) in acetonitrile (20 mL) was cooled on an ice-water bath. Bromine (100 mg) was added to this suspension through a syringe with stirring. The color of bromine soon disappeared. The solution was stirred at 0° C. for 10 more minutes and then N, N-diisopropyl ethylamine (2.2 eq. ca 360 µL) and (3,4-bis-methoxymethoxy-phenyl)-methanol (228 mg, 1 eq. either neat or in $CH_3CN$ solution) were introduced at 0° C. The resulted solution was slightly basic. It was stirred at 0° C. for 30 min before diluted with ethyl ether. After washed with saturated $NaH_2PO_4$ solution, dried over $MgSO_4$, and evaporated to dryness, it gave rise to a solid residue. Purification by silica gel column chromatography (eluting with ethyl acetate: hexane 3:7) rendered 180 mg of thick oil (yield 62%).

(3,4-Bis-methoxymethoxy-benzyl)-triphenyl-phosphonium bromide A solution of 4-bromomethyl-1, 2-bis-methoxymethoxy-benzene (1 eq) and $PPh_3$ (1.02 eq) in toluene was refluxed (oil bath 100–130° C.) overnight. White precipitates were collected and washed with cool toluene. The solid was dried under vacuum and the yield was about 90%.

4-[2-(3,4-Bis-methoxymethoxy-phenyl)-vinyl]-pyridine To a mixture of (3,4-Bis-methoxymethoxy-benzyl)-triphenyl-phosphonium bromide (800 mg) and 4-formylpyridine (130 mg) in ethanol was added lithium ethoxide solution (1.5 mL, 1.0 M in ethanol) over a period of 130 minutes. After additional 30 minutes of stirring, the solvent was stripped off by rotary evaporation under diminished pressure. The residue was dissolved in water and extracted with ethyl acetate. Back washed with water, the organic solution was dried over magnesium sulfate and concentrated on a rotary evaporator. Purification was carried out on a silica gel column using gradient ethyl acetate in dichloromethane (5–20%). It led to a semi-solid mixture of E- and Z-isomers in ca 80% yield.

4-[2-(3,4-Dihydroxy-phenyl)-vinyl]-1-(2-ethoxycarbonyl-2-oxo-ethyl)-pyridinium; bromide A solution of 4-[2-(3,4-bis-methoxymethoxy-phenyl)-vinyl]-pyridine (70 mg) and ethyl 3-bromopyruvate (200 µL) in 1, 4-dioxane (10 mL) was stirred at 90–110° C. overnight. The initial colorless solution turned into brown and some orange precipitate appeared. The dioxane solvent was stripped off on a rotary evaporator and the resulted solid was washed extensively with ethyl ether. Without further purification, it was dissolved in methanol (20 mL) and concentrate HBr (48% aqueous solution, 10 drops) was introduced. After stirred at room temperature overnight, followed by removal of solvent by rotary evaporation, the residue was successively washed with ethyl ether, ethyl acetate, dichloromethane, and then dried under vacuum. This gave the expected product, 4-[2-(3,4-dihydroxy-phenyl)-vinyl]-1-(2-ethoxycarbonyl-2-oxo-ethyl)-pyridinium; bromide, as an orange solid (83 mg, 87%). $^1$H-NMR (300 MHz, DMSO-$d_6$) δ (ppm): 8.83 (dd, J=1.8, 7.1 Hz), 8.76–8.55 (m), 8.22 (dd, J=1.5, 7.0 Hz), 8.10–8.00 (m), 7.80 (dd, J=6.2, 16.1 Hz), 7.75–7.5 (m), 7.31–7.10 (m), 6.87 (d, J=8.2 Hz), 4.72 (q, J=13.5 Hz), 4.34–4.26 (m), 3.86–3.53 (m), 1.52–1.15 (m). $^{13}$C-NMR (75 MHz, DMSO-$d_6$) δ (ppm): 167.3, 155.7, 154.8, 148.4, 148.2, 145.3, 145.2, 144.9, 142.5, 141.8, 139.9, 131.3, 131.2, 128.3, 128.1, 126.8, 126.7, 122.1, 122.0, 121.7, 121.6, 119.0, 118.6, 115.0, 114.9, 114.0, 113.7, 113.6, 94.4, 63.5, 62.0, 61.7, 12.6, and 12.4.

Example 6

3-(4,5-Dihydro-1H-imidazol-2-ylsulfanyl)-2-oxo-propionic acid ethyl ester

6A. Formula Ia where A is 4,5-Dihydro-1H-imidazol-2-yl, R is Ethyl, and X is S

A mixture of 2-imidazolidinethione (1.02 g, 10 mmol), ethyl 3-bromopyruvate (1.95 g, 10 mmol), potassium carbonate (1.38 g, 10 mmol), sodium iodide (10 mg), Adogen (200 mg) in N, N-dimethyl formamide (15 mL) was stirred at 20° C. for 15 hours under nitrogen. The reaction mixture was diluted with water and then extracted ethyl acetate. Organic phase was dried over sodium sulfate, evaporated, and chromatographed (silica gel, dichloromethane-methanol 9:1), giving the expected product, 3-(4,5-dihydro-1H-imidazol-2-ylsulfanyl)-2-oxo-propionic acid ethyl ester, as a brown solid (1.8 g, 83%). $^1$H-NMR (CDCl$_3$, 300 MHz) δ (ppm): 4.36 (d, J=7.1 Hz, 2H), 4.25–4.00 (m, 3H), 3.57 (d, J=11.2 Hz, 1H), 3.50–3.35 (m, 1H), 3.25–3.10 (m, 1H), 1.37 (t, J=7.1 Hz, 3H).

6B. Other Compounds of Formula Ia

Similarly, by following the procedures of Example 6A and substituting 2-imidazolidinethione with 2-amino-3-(1H-imidazol-4-yl)propionic acid, there is obtained 2-amino-3-[1-(2-ethoxycarbonyl-2-oxo-ethyl)-1H-imidazol-4-yl]-propionic acid.

Example 7

2-Hydroxy-3-(1H-imidazol-2-ylsulfanyl)-5-oxo-hex-2-enedioic acid diethyl ester

A solution of 3H-Imidazole-4-thiol (0.1 g, 1.0 mmol), ethyl 3-bromopyruvate (0.31 g, 1.6 mmol), and triethylamine (0.2 mL) in MeOH/CH$_2$Cl$_2$ (1.5 mL/1.5 mL) in a capped vial was shaken at room temperature overnight. After removal of the volatiles, the residues were dissolved in methylene chloride and loaded onto the top of a silica gel column. Elution with ethyl acetate in methylene chloride (10%) gave the product (a di-pyruvate conjugate) as a semi solid (87 mg, 35%). $^1$H-NMR (CDCl$_3$, 300 MHz) δ (ppm): 1.19 (t, 3H), 1.37 (t, 3H), 4.12 (q, 2H), 4.37 (q, 2H), 4.59 (d, 1H), 4.68 (d, 1H), 7.06 (ss, 2H).

Example 8

3-[2-Amino-9-(3,4-dihydroxy-5-hydroxymethyl-tetrahydro-furan-2-yl)-9H-purin-6-ylsulfanyl]-2-oxo-propionic acid ethyl ester 8A. Formula Ia where A is 3-[2-Amino-9-(3,4-dihydroxy-5-hydroxymethyl-tetrahydrofuran-2-yl)-9H-purin-6-yl, R is Ethyl, and X is S To a solution of (−)-2-amino-6-mercaptopurine riboside (100 mg, 0.33 mmol) in N, N-dimethyl formamide (2 mL) was added ethyl 3-bromopyruvate (0.050 mL, 0.37 mmol) under nitrogen. After stirred at 20° C. for 1 hour, the reaction mixture was diluted with water and then concentrated on a rotary evaporator under vacuum. The residue was triturated with ethyl acetate. The ethyl acetate phase was concentrated and chromatographed (silica gel, methylene chloride-methanol 100:5 to 100:10), affording 21 mg of the expected product, 3-[2-amino-9-(3,4-dihydroxy-5-hydroxymethyl-tetrahydro-furan-2-yl)-9H-purin-6-ylsulfanyl]-2-oxo-propionic acid ethyl ester. $^1$H-NMR (D$_3$COD, 300 MHz) δ (ppm): 8.13 (s, 1H), 5.87 (d, J=6.1 Hz, 1H), 4.70–4.60 (m, 1H), 4.35–4.30 (m, 2H), 4.20–4.05 (m, 4H), 3.90–3.70 (m, 2H), 1.20 (t, J=7.1 Hz, 3H). MS (ESI) m/z: 414 (M+1, 100), 432 (M+H$_2$O+1, 84), 446 (m+Na, 45).

8B. Other Compounds of Formula Ia

Similarly, by following the procedures of Example 8A and substituting (−)-2-amino-6-mercaptopurine riboside with the following:
(−)-6-mercaptopurine, and
(−)-6-mercaptopurine riboside
there are obtained the following:
2-oxo-3-(9H-purin-6-ylsulfanyl)-propionic acid ethyl ester, and
3-[9-(3,4-Dihydroxy-5-hydroxymethyl-tetrahydro-furan-2-y)-9H-purin-6-ylsulfanyl-]-2-oxo-propionic acid ethyl ester.

Example 9

2-Oxo-3-(5-sulfo-1H-benzoimidazol-2-ylsulfanyl)-propionic acid ethyl ester sodium salt 9A. Formula Ia where A is 5-sulfo-1H-benzoimidazol-2-yl sodium salt, R is Ethyl, and X is S To a solution of 2-mercapto-5-benzimidazole-sulfonic acid sodium salt (252 mg, 1.0 mmol) in water (3 mL) was added ethyl 3-bromopyruvate (0.150 mL, 1.19 mmol) under nitrogen. The resulted solution was stirred at 20° C. for 1 hour. Water was removed under vacuum and the residue washed with ethyl acetate. Dried over sodium sulfate, the organic solution was evaporated to dryness under vacuum. This gave 300 mg (82%) of product, 2-oxo-3-(5-sulfo-1H-benzoimidazol-2-ylsulfanyl)-propionic acid ethyl ester sodium salt, which was sufficiently pure to be used without further purification. $^1$H-NMR (D$_3$COD, 300 MHz) δ (ppm): 8.70 (dd, J=0.6 Hz, J=1.5 Hz, 1H), 7.95 (dd, J=1.5 Hz, J=8.6 Hz, 1H), 7.74 (dd, J=0.6 Hz, J=1.5 Hz, 1H), 4.27 (q, J=7.1 Hz, 2H), 3.93 (d, J=14.2 Hz, 1H), 3.81 (d, J=14.2 Hz, 1H), 1.30 (t, J=7.1 Hz, 3H). MS (ESI), 367 (M+1, 28), 345 (M−Na+1, 100).

9B. Other Compounds of Formula Ia

Similarly, by following the procedures of Example 9A and substituting 2-mercapto-5-benzimidazole-sulfonic acid sodium salt with 6-ethoxy-2-mercaptobenzimidazole, there is obtained 3-(6-ethoxy-benzothiazol-2-ylsulfanyl)-2-oxo-propionic acid ethyl ester.

Example 10

Formula Ia where A is 5-Amino-2H-[1,2,4]triazol-3-yl, R is Ethyl, and X is S

To a suspension of 3-amino-5-mercapto-1,2,4-triazole (116 mg, 1.0 mmol) in methanol (3 mL) was added ethyl 3-bromopyruvate (0.150 mL, 1.19 mmol) under nitrogen. The resulting solution was stirred at 20° C. for 1 hour. A clear solution was formed after about 30 min. Methanol was removed under vacuum, leading to 227 mg of solid (99% of yield). Proton NMR indicated that 3-(5-amino-2H-[1,2,4]triazol-3-ylsulfanyl)-2-oxo-propioic acid ethyl ester was one of the major products. $^1$H-NMR (D$_3$COD, 300 MHz) δ (ppm): 4.30–4.20 (m, 2H), 3.51 (br. s, 2H), 1.30 (t, J=7.1 Hz, 3H).

Example 11

11A. Formula Ia where A is 5-Amino-[1,3,4]thiadiazol-2-yl, R is Ethyl, and X is S To a suspension of 5-amino-1,3,4-thiadiazole-2-thiol (133 mg, 1.0 mmol) in methanol (3 mL) was added ethyl 3-bromopyruvate (0.150 mL, 1.19 mmol) under nitrogen. The resulting solution was stirred at 20° C. for 1 hour. A clear solution was formed after about 45 min. Methanol was removed under vacuum, giving 200 mg of solid (in 81% yield). Proton NMR indicated that 3-(5-amino-[1,3,4]thiadiazol-2-ylsulfanyl)-2-oxo-propionic acid ethyl ester was one of major products. $^1$H-NMR (D$_3$COD, 300 MHz) δ (ppm): 4.35–4.20 (m, 2H), 3.58 (dd, AB system, 2H), 1.31 (t, J=7.1 Hz, 3H).

11B. Other Compounds of Formula Ia

Similarly, by following the procedures of Example 11A and substituting 5-amino-1,3,4-thiadiazole-2-thiol with 5-(2-ethoxycarbonyl-2-oxo-ethylsulfanyl)-[1,3,4]thiadiazol-2-thiol there is obtained 3-[5-(2-ethoxycarbonyl-2-oxo-ethylsulfanyl)-[1,3,4]thiadiazol-2-ylsulfanyl]-2-oxo-propionic acid ethyl ester.

Example 12

12A. Formula Ia where A is 5-Nitro-1H-benzoimidazol-2-yl, R is Ethyl, and X is S To a solution of 2-mercapto-5-nitrobenzimidazole (195 mg, 1.0 mmol) and ethyl 3-bromopyruvate (0.150 mL, 1.19 mmol) in methanol (2.5 mL) and acetone (2 mL) was added imidazole (68 mg, 1.0 mmol). The resulted solution was shaken at 20° C. for 4 hour. After the removal of solvents under vacuum, the residue was triturated with ethyl ether. The ether phase was discarded. The residue was treated with sodium bicarbonate aqueous solution and ethyl ether. The ether phase was washed successively with sodium bicarbonate aqueous solution, water, and dried over magnesium sulfate. Evaporation to dryness under vacuum gave 200 mg (65% of yield) of the expected product, 3-(5-nitro-1H-benzoimidazol-2-ylsulfanyl)-2-oxo-propionic acid ethyl ester. Proton NMR showed the product was sufficiently pure to be used without further purification. $^1$H-NMR (D$_3$COD, 300 MHz) δ (ppm): 8.35 and 8.08 (2 br. s, 1H), 8.12 (d, J=8.7 Hz, 1H), 7.50 and 7.28 (2 br. s, 1H), 4.42 (q, J=7.1 Hz, 2H), 4.41 (br. s, 1H), 4.06 (br. s, 1H), 1.30 (t, J=7.1 Hz, 3H). MS (ESI) m/z: 310 (M+1, 100).

12B. Other Compounds of Formula Ia

Similarly, by following the procedures of Example 12A and substituting 2-mercapto-5-nitrobenzimidazole with the following:
2-amino-3-mercapto propionic acid
2-amino-3-sulfinyl propionic acid,
2-amino-3-sulfonyl propionic acid, and
2-acetylamino-3-mercapto propionic acid
there are obtained the following:
2-amino-3-(2-ethoxycarbonyl-2-oxo-ethylsulfanyl)-propionic acid and 3-(2-amino-2-carboxy-ethylsulfanyl)-2-hydroxy-acrylic acid ethyl ester,
2-amino-3-(2-ethoxycarbonyl-2-oxo-ethanesulfinyl)-propionic acid
2-amino-3-(2-ethoxycarbonyl-2-oxo-ethanesulfonyl)-propionic acid, and
2-acetylamino-3-(2-ethoxycarbonyl-2-oxo-ethylsulfanyl)-propionic acid.

Example 13

13A. Formula Ia where A is 5-Phenyl-[1.3,4]oxadiazol-2-yl, R is Ethyl, and X is S To a solution of 5-phenyl-1,3,4-oxadiazole-2-thiol (178 mg, 1.0 mmol) and ethyl 3-bromopyruvate (0.150 mL, 1.19 mmol) in methanol (2 mL) and acetone (2 mL) was added imidazole (68 mg, 1.0 mmol). The resulted solution was shaken at 20° C. for 4 hour. After the removal of solvents under vacuum, the residue was triturated with ethyl ether. The ether phase was discarded. The residue was treated with sodium bicarbonate aqueous solution and ethyl ether. The ether phase was washed successively with sodium bicarbonate aqueous solution, water, and dried over magnesium sulfate. Evaporation to dryness under vacuum gave 209 mg (72% of yield) of the expected product, 2-oxo-3-(5-phenyl-[1,3,4]oxadiazol-2-ylsulfanyl)-propionic acid ethyl ester. Proton NMR showed the product was sufficiently pure to be used without further purification. $^1$H-NMR (CDCl$_3$, 300 MHz) δ (ppm): 7.90–7.80 (m, 2H), 7.60–7.35 (m, 3H), 4.41 (q, J=7.1 Hz, 2H), 3.44 (br. s, 2H), 1.26 (t, J=7.1 Hz, 3H).

13B. Other Compounds of Formula Ia

Similarly, by following the procedures of Example 13A and substituting 5-phenyl-1,3,4-oxadiazole-2-thiol with 3-phenyl-1,2,4-oxadiazole-2-thiol, there is obtained 2-oxo-3-(3-phenyl-[1,2,4]oxadiazol-5-ylsulfanyl)-propionic acid ethyl ester.

Example 14

Formula III where $R^{3.1}$ to $R^{3.4}$ are H, and $R^{3.5}$ is COOH

To a solution of L-cysteine (2.42 g, 20 mmol) in water (70 mL) was added 3-bromopyruvic acid (3.34 g, 20 mmol) at room temperature with stirring. The clear solution turned cloudy gradually. After stirring for 2 hours at room temperature, the white precipitates were filtered, washed with water, and dried under vacuum. This gave a compound of Formula Ia where A is cysteine, which cyclizes with the enol of pyruvate to afford the title compound of Formula III, 3,4-dihydro-2H-[1,4] thiazine-3,5-dicarboxylic acid, as a grey powder product (2.42 g, 58%). $^1$H-NMR (DMSO-d$_6$, 300 MHz) δ (ppm): 6.00 (s, 1H), 5.17 (br., s, 1H), 4.25 (t, 1H), 2.94–3.05 (m, 2H). $^{13}$C-NMR (DMSO-d$_6$, 75 MHz) δ (ppm): 25.8, 52.3, 98.0, 128.8, 163.6, and 172.0. MS (ESI) m/z: 190 (M+H, 100).

Example 15

Formula Ia where A is γ-Glu-Cys-Gly, R is H, and X is a Covalent Bond and

Formula II where $R^1$ is COOH, $R^2$ is H, $R^3$ is CH$_2$—S-Pyruvate, $R^4$ is H, $R^5$ is H, k is 0, m is 2, and n is 1

15A. To a solution of glutathione (2-amino-4-[1-(carboxymethyl-carbamoyl)-2-mercapto-ethylcarbamoyl]-butyric acid) (3.0 g, 9.76 mmol) in water (34 mL) and methanol (4 mL) (degassed and purged with nitrogen) was added 3-bromopyruvic acid (1.63 g, 9.76 mmol) at room temperature. After stirring for 3 hours at room temperature, the mixture was concentrated on a rotary evaporator under the reduced pressure. The solution was then washed with methylene chloride thoroughly. The organic layer was discarded. The aqueous layer was evaporated to dryness under reduced pressure. After drying under high vacuum for 48 hours, the expected product was afforded as a yellowish solid in quantitative yield. NMR data indicate that there exist two tautomeric isomers in the product, namely the keto form, 2-amino-4-[1-(carboxymethyl-carbamoyl)-2-(2-carboxy-2-oxo-ethylsulfanyl)-ethylcarbamoyl]-butyric acid, and the enol form, 3-[2-(4-amino-4-carboxy-butyrylamino)-2-(carboxymethyl-carbamoyl)-ethylsulfanyl]-2-hydroxy-acrylic acid. $^1$H-NMR (D$_3$COD, 300 MHz) δ (ppm): 6.45 (s, 0.4H), 6.43–6.48 (m, 1H), 4.06–4.10 (m, 1H), 3.95 (s, 2H), 2.80–2.93 (m, 2.6H), 2.60–2.65 (m, 2H), and 2.14–2.27 (m, 2H).

15B. Other Compounds of Formula Ia

Similarly, by following the procedures of Example 15A and substituting glutathione with cysteine, there are obtained 3-(2-amino-2-carboxy-ethylsulfanyl)-2-oxo-propionic acid and 3-(2-amino-2-carboxy-ethylsulfanyl)-2-hydroxy-acrylic acid.

Example 16

Formula Ia where A is γ-Glu-Cys-Gly, R is Ethyl, and X is a Covalent Bond and

Formula II where $R^1$ is COOH, $R^2$ is H, $R^3$ is CH$_2$—S-Pyruvate Ethyl Ester, $R^4$ is H, $R^5$ is H, k is 0, m is 2, and n is 1

To a solution of glutathione (2-amino-4-[1-(carboxymethyl-carbamoyl)-2-mercapto-ethylcarbamoyl]-butyric acid) (8.14 g, 26.5 mmol) in water (50 mL) and methanol (10 mL) (degassed and purged with nitrogen) was added bromo-3-ethylpyruvate (5.17 g, 26.5 mmol) at room temperature. Upon the addition of bromo-3-ethylpyruvate, the cloudy suspension turned to yellowish translucent almost instantly. After stirring for 2 hours at room temperature, the mixture was concentrated on a rotary evaporator under the reduced pressure. The solution was then washed with methylene chloride thoroughly. The organic layer was discarded. The aqueous layer was evaporated to dryness under reduced pressure. After drying under high vacuum for 48 hours, a white solid was obtained as the product (g, %). NMR data indicate that there exist two tautomeric forms of the product, namely the keto form, 2-amino-4-[1-(carboxymethyl-carbamoyl)-2-(2-carboxy-2-oxo-ethylsulfanyl)-ethylcarbamoyl]-butyric acid ethyl ester, and the enol form, 3-[2-(4-amino-4-carboxy-butyrylamino)-2-(carboxymethyl-carbamoyl)-ethylsulfanyl]-2-hydroxy-acrylic acid ethyl ester. $^1$H-NMR (D$_3$COD, 300 MHz) δ (ppm): 1.17 (t, 3H), 1.93 (m, 2H), 2.11 (m, 2H), 2.75–3.28 (m, 2H), 2.29 (ss, 1.6H), 3.93 (s, 2H), 4.09 (m, 1H), 4.25 (q, 2H), 4.83 (m, 1H), 6.43 (s, 0.4H. $^{13}$C-NMR (D$_3$COD, 75 MHz) δ (ppm): 14.1, 26.6, 32.1, 35.6, 40.0, 41.4, 53.2, 54.6, 62.1, 62.7, 100.0, 113.4, 139.7,163.4, 170.8, 172.3, 174.1. MS (ESI) m/z: 422 (M+H, 100), 440 (M+H+H$_2$O, 42).

Example 17

Formula II where $R^1$ is COOCH$_3$, $R^2$ is H, $R^3$ is CH$_2$—S-keto-Pyruvate Ethyl Ester, $R^4$ is H, $R^5$ is CH$_3$, k is 0, m is 2, and n is 1

A mixture of 2-Amino-4-[1-(carboxymethyl-carbamoyl)-2-(2-ethoxycarbonyl-2-oxo-ethylsulfanyl)-ethylcarbamoyl]-butyric acid (200 mg) and p-toluenesulfonic acid (30 mg) in methanol (100 mL) was heated to reflux for 72 h. The solvent was then evaporated and the residue was dried under high vacuum to afford the desired product, 2-amino-4-[2-(2-ethoxycarbonyl-2-oxo-ethylsulfanyl)-1-(methoxycarbonylmethyl-carbamoyl)-ethylcarbamoyl]-butyric acid methyl ester, as a yellowish sticky solid. $^1$H-NMR (D$_3$COD, 300 MHz) δ (ppm): 6.24 (d, J=10.5 Hz, 0.22 H), 4.49–4.4.33 (m, 1H), 4.15–3.91 (m, 3H), 3.76 (s, 3H), 3.65–3.57 (m, 2H), 3.51 (s, 3H), 3.21–2.73 (m, 2.8 H), 2.45–2.43 (m, 2H), 2.10–1.92 (m, 2H), 1.13–1.03 (m, 3H).

Example 18

18A. Formula II where $R^1$ is COOH, $R^2$ is H, $R^3$ is CH$_2$—S-keto-Pyruvate Decyl Ester, $R^4$ is H, $R^5$ is H, k is 0, m is 2, and n is 1

A mixture of 3-bromopyruvic acid (200 mg), decyl alcohol (300 mg), and p-toluenesulfonic acid (20 mg) in benzene (80 mL) was heated to reflux for 8 h in the dark. After solvent removal, the residue was chromatographed to afford 320 mg of clear oil. NMR indicated the product contained the desired compound and small amount of excess alcohol. To this obtained intermediate (320 mg) in methanol (degassed, 50 mL) was added an aqueous glutathione solution (250 mg in 5 mL of water). The resulting cloudy solution was stirred at room temperature for 5 h. The solvent was then evaporated and the residue was chromatographed on silica gel with methylene chloride/methanol (7:1 and then 1:1) to afford 198 mg of the expected product, 2-amino-4-[1-(carboxymethyl-carbamoyl)-2-(2-decyloxycarbonyl-2-oxo-ethylsulfanyl)-ethylcarbamoyl]-butyric acid, as a white sticky solid. $^1$H-NMR (300 MHz, DMSO-$d_6$) δ (ppm): 6.50 (s, 0.50 H), 4.53–4.47 (m, 1H), 4.12 (t, 2H), 3.77 (s, 2H), 3.75–3.65 (m, 2H), 3.19–2.83 (m, 2.5 H), 2.53 (s, 2H), 2.40–2.33 (m, 2H), 2.02–1.97 (m, 2H), 1.65–1.59 (m, 2H), 1.26 (s, 14 H), 0.87 (t, J=6 Hz, 3H). MS (ESI) m/z: (M+H$^+$) 534.

18B. Other Compounds of Formula Ia

Similarly, by following the procedures of Example 18A and substituting decyl alcohol with:
octadecyl alcohol,
2-isopropyl-5-methyl-cyclohexanol
cyclopentanol,
pentanol,
butanol
isopropanol
hexanol
sec-butanol
1-ethylpropanol, and
10-(1,5-dimethyl-hexyl)-10a,11a-dimethyl-2,3,4,6,6a,7,7a,8,9,10,10a,11,11a,11b-tetradecahydro-1H-cyclopenta[b]phenanthren-3-ol
there are obtained the following compounds, respectively:
2-amino-4-[1-(carboxymethyl-carbamoyl)-2-(2-octadecyloxycarbonyl-2-oxo-ethylsulfanyl)-ethylcarbamoyl]-butyric acid,
2-amino-4-{1-(carboxymethyl-carbamoyl)-2-[2-(2-isopropyl-5-methyl-cyclohexyloxycarbonyl)-2-oxo-ethylsulfanyl]-ethylcarbamoyl}-butyric acid, MS (ESI) m/z: 532 (M$^+$+H, 100)
2-amino-4-[1-(carboxymethyl-carbamoyl)-2-(2-cyclopentyloxycarbonyl-2-oxo-ethylsulfanyl)-ethylcarbamoyl]-butyric acid, MS (ESI) m/z: 662 (M$^+$+H, 100)
2-amino-4-[1-(carboxymethyl-carbamoyl)-2-(2-oxo-2-pentyloxycarbonyl-ethylsulfanyl)-ethylcarbamoyl]-butyric acid, MS (ESI) m/z: 464 (M$^+$+H, 100),
2-amino-4-[2-(2-butoxycarbonyl-2-oxo-ethylsulfanyl)-1-(carboxymethyl-carbamoyl)-ethylcarbamoyl]-butyric acid, $^1$H NMR (D$_2$O): 0.83–0.91 (m, 3H), 1.29–1.39 (m, 2H), 1.60–1.67 (m, 2H), 2.12–2.18 (m, 2H), 4.47–2.60 (m, 2H), 2.80–3.0 (m, 1.5H), 3.04–3.20 (m, 1H), 3.21–3.33 (m, 0.5H), 3.82–3.98 (m, 3H)4.14–4.28 (m, 2H), 4.46–4.70 (m, 1H),
2-amino-4-[1-(carboxymethyl-carbamoyl)-2-(2-isopropoxycarbonyl-2-oxo-ethylsulfanyl)-ethylcarbamoyl]-butyric acid, MS (ESI) m/z: 436 (M$^+$+H, 100),
2-amino-4-[1-(carboxymethyl-carbamoyl)-2-(2-hexyloxycarbonyl-2-oxo-ethylsulfanyl)-ethylcarbamoyl]-butyric acid, MS (ESI) m/z: 478 (M$^+$+H, 100),
2-amino-4-[2-(2-sec-butoxycarbonyl-2-oxo-ethylsulfanyl)-1-(carboxymethyl-carbamoyl)-ethylcarbamoyl]-butyric acid, MS (ESI) m/z: 450 (M$^+$+H, 100),
2-amino-4-{1-(carboxymethyl-carbamoyl)-2-[2-(1-ethyl-propoxycarbonyl)-2-oxo-ethylsulfanyl]-ethylcarbamoyl}-butyric acid, and
2-amino-4-(1-(carboxymethyl-carbamoyl)-2-{2-[10-(1,5-dimethyl-hexyl)-10a,11a-dimethyl-2,3,4,6,6a,7,7a,8,9,10,10a,11,11a,11b-tetradecahydro-1H-cyclopenta[b]phenanthren-3-yloxycarbonyl]-2-oxo-ethylsulfanyl}-ethylcarbamoyl)-butyric acid.

Example 19

19A. Formula Ia where A is γ-Glu-CysX-Gly, R is H, and X is a Covalent Bond; and Formula II where R$^1$ is COOH, R$^2$ is H, R$^3$ is CH$_2$—S-Keto-pyruvate Ethyl Ester, R$^4$ is H, R$^5$ is H, k is 0, m is 2, and n is 1

Formula 203 where AA$_1$ is Gly Following art-recognized procedures, NH-Fmoc-protected GlyOH (1 eq) is dissolved in DCM and contacted with DCC (0.6 eq) in the presence of a catalytic amount of DMAP to give the F-moc protected anhydride corresponding to Formula 202 where AA$_1$ is glycine, i.e., O-(Gly-NHFmoc)$_2$. The anhydride so-prepared (10 eq) is dissolved in DCM, to which is added DIC (5 eq) in small portions, with stirring. The resulting mixture is stirred for 1 h to give a clear solution that is then added to Wang resin (1 eq, pre-swelled in DMF) in the presence of DMAP (0.1 eq). The resulting resin suspension is shaken for 1 h, and then thoroughly washed with DMF to afford the resin-bound, NH-Fmoc-protected glycine corresponding to Formula 203, which is carried forward without further purification.

Formula 204 where AA$_1$ is Gly The Fmoc protected, resin bound glycine of Formula 203 is de-protected using 20% piperidine in DMF followed by DMF wash (5 times) to give the corresponding resin-bound glycine of Formula 204, which is carried forward without further purification.

Formula 206 where AA$_1$ is Gly, and AA$_2$ is Cys The resin-bound glycine of Formula 204 (1 eq) is contacted with TBTU (2 eq), DIPEA (4 eq) and NH-Fmoc-protected, S-t-butylthio-cysteine (2 eq) (Formula 205), followed by DMF wash (3 times) to afford the corresponding NH-Fmoc protected, resin bound di-peptide of Formula 206, which is carried forward without further purification.

Formula 207 where AA$_1$ is Gly, and AA$_2$ is CyS The Fmoc protected, resin bound di-peptide of Formula 206 is de-protected using 20% piperidine in DMF followed by DMF wash (5 times) to give the corresponding resin-bound di-peptide of Formula 207, which is carried forward without further purification.

Formula 209 where AA$_1$ is Gly, AA$_2$ is Cys, and AA$_3$ is γ-Glu The resin-bound di-peptide of Formula 207 (1 eq) is contacted with TBTU (2 eq), DIPEA (4 eq) and NH-Fmoc-protected glutamine (2 eq) (Formula 208), followed by DMF wash (3 times) to afford the corresponding NH-Fmoc protected, resin bound tri-peptide of Formula 209, which is carried forward without further purification.

Formula 210 where AA$_1$ is Gly, AA$_2$ is Cys, and AA$_3$ γ-Glu The Fmoc protected, resin bound tri-peptide of Formula 209 is de-protected using 20% piperidine in DMF followed by DMF wash (5 times) to give the corresponding resin-bound tri-peptide of Formula 210, which is carried forward without further purification.

Formula 301c where AA$_1$ is Gly, AA$_2$ is Cys, L is t-Butylthio, and AA$_3$ is γ-Glu The resin-bound tri-peptide of Formula 210 (corresponding to Formula 300c where AA$_2$ is t-butylthio protected cysteine) is treated with 50% mercaptoethanol (in DMF) for 5 hours, followed by 10% DTT for 1 hour to remove the t-butylthio protecting group, affording the corresponding resin-bound tripeptide of Formula 301c, after filtration and washed with DMF (3 times) and DCM (5 times).

Formula 302c where AA$_1$ is Gly, AA$_2$ is Cys, AA$_3$ is γ-Glu, and R is Ethyl To the resin-bound tripeptide of Formula 301c, dissolved in DMF, is slowly added ethyl 3-bromopyruvate (Formula 102 where Halo is Bromo and R is Ethyl) (2 eq). The nucleophilic substitution is stopped by filtration after 1 hour to afford the resin-bound tri-peptide conjugate of Formula 302c, which is washed with DMF (3 times), DCM (10 times), and MeOH (2 times), and dried under high vacuum for 10 hours.

Formula 303c where $AA_1$ is Gly, $AA_2$ is Cys, $AA_3$ is γ-Glu, and R is Ethyl The resin-bound tri-peptide conjugate of Formula 302c is cleaved from the resin by treatment for 3 hours using a cocktail containing 95% TFA (5% water). The solvent is partially removed and 50 fold of cold ether is added to the mixture. The clear supernatant is removed and the precipitate washed with cold ether (2 times). The resulting solid is dissolved in water, filtered through a pre-packed C18 short column, and lyophilized to afford the title compound of Formulae I and II, i.e., 2-amino-N-[1-(carboxymethyl-carbamoyl)-2-(2-ethoxycarbonyl-2-oxo-ethylsulfanyl)-ethyl]-succinamic acid, as a fluffy white solid. $^1$H-NMR (300 MHz, $D_2O$) δ (ppm): 4.63–4.47 (m, 1H), 4.27–4.17 (m, 2H), 3.96 (s, 2H), 3.26–2.91 (m, 6H), 1.30–1.23 (m, 3H). MS (ESI) m/z: 408 (M+H$^+$).

19B. Other Compounds of Formulae Ia and II

By following the procedures of Example 19A and substituting Formulae 202, 205, 208, and/or 102 to introduce the desired, corresponding moieties at $AA_1$, $AA_2$, $AA_3$ and R, there are obtained the following:

3-[2-[2-Amino-3-(2-ethoxycarbonyl-2-oxo-ethylsulfanyl)-propionylamino]-2-(carboxymethyl-carbamoyl)-ethylsulfanyl]-2-oxo-propionic acid ethyl ester. $^1$HNMR (300 MHz, $D_2O$) δ (ppm): 4.70–4.15 (m, 6H), 3.96–3.92 (m, 4H), 3.19–2.86 (m 6H), 1.36–1.26 (m, 6H). MS (ESI) m/z: 510 (M+H$^+$).

3-[2-(2-Amino-3-mercapto-propionylamino)-2-(carboxymethyl-carbamoyl)-ethylsulfanyl]-2-oxo-propionic acid ethyl ester. $^1$H-NMR (300 MHz, $CD_3OD$) δ (ppm): 4.69–4.55 (m, 1H), 4.42–4.22 (m, 3H), 3.94 (s, 2H), 3.45–2.83 (m, 5H), 1.35–1.1.20 (m, 3H). MS (ESI) m/z: 396 (M+H$^+$).

4-Amino-4-[1-(carboxymethyl-carbamoyl)-2-(2-ethoxycarbonyl-2-oxo-ethylsulfanyl)-ethylcarbamoyl]-butyric acid. $^1$H-NMR (300 MHz, $CD_3OD$) δ (ppm): 4.68–4.38 (m, 1H), 4.23–4.19(m, 2H), 4.07–4.01 (m, 1H), 3.97–3.94 (m, 2H), 3.20–3.12 (m, 1H), 3.00–2.87 (m, 2H), 2.53–2.59 (m, 2H), 2.21–2.10 (m, 2H), 1.28 (t, J=7.2 Hz, 3H). MS (ESI) m/z: 422 (M+H$^+$).

2-Amino-4-[1-(carboxymethyl-carbamoyl)-2-(2-carboxy-2-oxo-ethylsulfanyl)-ethylcarbamoyl]-butyric acid ethyl ester. $^1$H-NMR (300 MHz, D2O) δ (ppm): 6.80 (s, 0.13 H), 4.73–4.51(m, 1H), 4.26–4.18 (m, 2H), 4.09–4.02 (m, 1H), 3.96 (s, 2H), 3.29–83 (m, 2.5 H), 2.56–2.49 (m, 2H), 2.21–2.12 (m, 2H), 1.24 (t, J=7.5Hz, 3H). MS (ESI) m/z: 422 (M+H$^+$, 100).

4-[1-(Carboxymethyl-carbamoyl)-2-mercapto-ethylcarbamoyl]-4-(2-oxo-propionylamino)-buyric acid.

3-[2-(2-Amino-3-carboxy-propionylamino)-2-(carboxymethyl-carbamoyl)-ethylsulfanyl]-2-hydroxy-acrylicacid ethyl ester.

3-{2-Amino-2-[1-carboxy-2-(2-ethoxycarbonyl-2-hydroxy-vinylsulfanyl)-ethylcarbamoyl]-ethylsulfanyl}-2-hydroxy-acrylic acid ethyl ester.

2-Acetylamino-4-[1-(carboxymethyl-carbamoyl)-2-(2-ethoxycarbonyl-2-oxo-ethylsulfanyl)-ethylcarbamoyl]-butyric acid. $^1$H-NMR (D2O, 300 MHz) δ (ppm): 6.41 (s, 0.3 H), 4.56–4.38 (m, 1H), 4.20–4.05 (m, 3H), 3.83 (s, 2H), 3.19–2.72 (m, 3H), 2.27 (m, 2H), 2.12–1.77 (m, 2H), 1.85 (s, 3H), 1.13 (m, 3H). MS(ESI) m/z: 465 (M+H$^+$, 100).

Example 20

20A. Formula II where $R^1$ is COOH, $R^2$ is 3-(6-Hydroxy-2,7,8-trimethyl-chroman-2-yl)-propionyl, $R^3$ is $CH_2$—S—Keto-pyruvate Ethyl Ester, $R^4$ is H, $R^5$ is H, k is 0, m is 2, and n is 1.

Formula 502c where $AA_1$ is Gly, $AA_2$ is Cys, and $AA_3$ is γ-Glu, and $R^2$ is 3-(6-Hydroxy-2,7,8-trimethyl-chroman-2-yl)-propionyl A resin-bound tri-peptide of Formula 500c (made, e.g., as described above with respect to Formula 210 in Example 19) is coupled, using pre-activated HOBt ester (DIC as dehydrating agent), with 3-(6-hydroxy-2,7,8-trimethyl-chroman-2-yl)-propionic acid (a diphenol acid of Formula 501) to give the corresponding amino-substituted resin-bound tri-peptide of Formula 502c.

Formula 503c where $AA_1$ is Gly, $AA_2$ is Cys, $AA_3$ is γ-Glu, and $R^2$ is 3-(6-Hydroxy-2,7,8-trimethyl-chroman-2-yl)-propionyl The resin-bound tri-peptide of Formula 502c is treated with 50% mercaptoethanol (in DMF) for 5 hours, followed by 10% DTT for 1 hour to remove the t-butylthio protecting group, affording the corresponding resin-bound tripeptide of Formula 503c, after filtration and washed with DMF (3 times) and DCM (5 times).

Formula 504c where $AA_1$ is Gly, $AA_2$ is CyS, $AA_3$ is γ-Glu, $R^2$ is 3-(6-Hydroxy-2,7,8-trimethyl-chroman-2-yl)-propionyl, and R is Ethyl To the resin-bound tripeptide of Formula 503c, dissolved in DMF, is slowly added ethyl 3-bromopyruvate (Formula 102 where Halo is Bromo and R is Ethyl) (2 eq). The nucleophilic substitution is stopped by filtration after 1 hour to afford the resin-bound tri-peptide conjugate of Formula 504c, which is washed with DMF (3 times), DCM (10 times), and MeOH (2 times), and dried under high vacuum for 10 hours.

Formula 505c where $AA_1$ is Gly, $AA_2$ is Cys, $AA_3$ is γ-Glu, $R^2$ is 3-(6-Hydroxy-2,7,8-trimethyl-chroman-2-yl)-propionyl and R is Ethyl The resin-bound tri-peptide conjugate of Formula 504c is cleaved from the resin by treatment for 3 hours using a cocktail containing 95% TFA (5% water). The solvent is partially removed and 50 fold of cold ether is added to the mixture. The clear supernatant is removed and the precipitate washed with cold ether (2 times). The resulting solid is dissolved in water, filtered through a pre-packed C18 short column, and lyophilized to afford the expected compound of Formulae I and II, i.e., 4-[1-(Carboxymethyl-carbamoyl)-2-(2-ethoxycarbonyl-2-oxo-ethylsulfanyl)-ethylcarbamoyl]-2-[3-(6-hydroxy-2,7,8-trimethyl-chroman-2-yl)-propionylamino]-butyric acid. $^1$H-NMR (300 MHz, $CD_3OD$) δ (ppm): 6.33 (s, 1H), 4.43–4.35 (m, 2H), 4.20–4.14(m, 2H), 3.93 (s, 2H), 3.35–3.05 (m, 2H), 2.98–2.83 (m, 2H), 2.71–2.65 (m, 2H), 2.45–2.37 (m, 5H), 2.25–1.7 (m, 11H), 1.30–1.19 (m, 6H). MS (ESI) m/z: 668 (M+H$^+$).

20B. Other Compounds of Formulae Ia and II

By following the procedures of Example 20A and substituting Formulae 500, 501 and/or 102 to introduce the desired, corresponding moieties at $AA_1$, $AA_2$, $AA_3$, $R^2$ and R, there is obtained the following:

4-[1-(Carboxymethyl-carbamoyl)-2-(2-ethoxycarbonyl-2-oxo-ethylsulfanyl)-ethylcarbamoyl]-2-{4-[2-(3,4-dihydroxy-phenyl)-vinyl]-benzoylamino}-butyric acid. $^1$H-NMR (300 MHz, $CD_3OD$) δ (ppm): 7.71–7.69 (m, 2H), 7.20–7.09 (m, 2H), 6.62–6.49 (m, 5H), 4.61–4.53(m, 2H), 4.25–4.18 (m, 2H), 3.88 (d, J=4.2 Hz, 2H), 3.17–2.84 (m, 4H), 2.51–2.43 (m, 2H), 2.38–2.10 (m, 2H), 1.33–1.16 (m, 3H). MS (ESI) m/z: 660 (M+H$^+$).

Example 21

21A. Formula II where $R^1$ is COOH, $R^2$ is 4-[2-(3,4-dihydroxy-phenyl)-ethyl]-benzoyl, $R^3$ is $CH_2$-S-Keto-pyruvate Ethyl Ester, $R^4$ is H, $R^5$ is H, k is 0, m is 2, and n is 1.

Formula 601c where $AA_1$ is Gly, $AA_2$ is Cys, and $AA_3$ is γ-Glu, and $R^2$ is 4-[2-(3,4-dihydroxy-phenyl)-ethyl]-benzoyl A resin-bound tripeptide of Formula 503c (prepared, for example, as described in Example 25A) is cleaved from the resin by treatment for 3 hours using a TFA cocktail (TFA 93.5%, Tis 1.5%, EDT 2.5%, water 2.5%). The solvent is partially removed and 50 fold of cold ether is added to the mixture. The clear supernatant is removed and the precipitate washed with cold ether (2 times). The resulting solid is dissolved in water, filtered through a pre-packed C18 short column, and lyophilized to afford the title compound of Formula 601c, i.e., 4-[1-(carboxymethyl-carbamoyl)-2-mercapto-ethylcarbamoyl]-2-{4-[2-(3,4-dihydroxy-phenyl)-ethyl]-benzoylamino}-butyric acid. $^1$H-NMR (300 MHz, CD$_3$OD) δ (ppm): 7.77–7.68 (m, 2H), 7.24–7.15 (m, 2H), 6.85–6.43 (m, 3H), 4.62–4.56 (m, 2H), 3.95 (d, J=4 Hz, 2H), 2.90–2.86 (m, 2H), 2.78–2.73 (m, 2H), 2.53–2.45 (m, 2H). MS (ESI) m/z: 548 (M +H$^+$).

Formula 602c where AA$_1$ is Gly, AA$_2$ is Cys, and AA$_3$ is γ-Glu, R$^2$ is 4-[2-(3,4-dihydroxy-phenyl)-ethyl]-benzoyl, and R is Ethyl To the tripeptide of Formula 601 c, dissolved in DMF, is slowly added ethyl 3-bromopyruvate (Formula 102 where Halo is Bromo and R is Ethyl) (2 eq). The nucleophilic substitution is stopped by filtration after 1 hour to afford the resin-bound tri-peptide conjugate of Formula 302c, which is washed with DMF (3 times), DCM (10 times), and MeOH (2 times), and dried under high vacuum for 10 hours, to afford the title compound, 4-[1-(carboxymethyl-carbamoyl)-2-(2-ethoxycarbonyl-2-oxo-ethylsulfanyl)-ethylcarbamoyl]-2-{4-[2-(3,4-dihydroxy-phenyl)-ethyl]-benzoylamino}-butyric acid.

21B. Other Compounds of Formula 601c and Formulae Ia and II

By following the procedures of Example 21A and substituting Formulae 500, 501 and/or 102 to introduce the desired, corresponding moieties at AA$_1$, AA$_2$, AA$_3$, R$^2$ and R, there are obtained the following:

4-[1-(Carboxymethyl-carbamoyl)-2-mercapto-ethylcarbamoyl]-2-[3-(6-hydroxy-2,7,8-trimethyl-chroman-2-yl)-propionylamino]-butyric acid. $^1$H-NMR (300 MHz, CD$_3$OD) δ (ppm): 6.34 (s, 1H), 4.54–4.3 (m, 2H), 3.92(d, J=3.9 Hz, 2H), 2.91–2.80 (m, 2H), 2.71–2.75 (m, 2H), 2.45–2.35 (m, 4H), 2.25–1.68 (m, 9H), 1.23–1.16 (m, 6H). MS (ESI) m/z 554 (M +H$^+$).

4-[1-(Carboxymethyl-carbamoyl)-2-(2-ethoxycarbonyl-2-oxo-ethylsulfanyl)-ethylcarbamoyl]-2-[3-(6-hydroxy-2,7,8-trimethyl-chroman-2-yl)-propionylamino]-butyric acid.

4-[1-(Carboxymethyl-carbamoyl)-2-mercapto-ethylcarbamoyl]-2-{4-[2-(3,4-dihydroxy-phenyl)-vinyl]-benzoylamino}-butyric acid. $^1$H-NMR (300 MHz, CD$_3$OD) δ (ppm): 7.40–7.08 (m, 4H), 6.79–6.46 (m, 3H), 4.64–4.55 (m, 2H), 3.97 (s, 2H), 3.22–2.86 (m, 2H), 2.52–2.42 (m, 2H), 2.40–2.02 (m, 2H). MS (ESI) m/z: 546 (M+H$^+$).

4-[1-(Carboxymethyl-carbamoyl)-2-(2-ethoxycarbonyl-2-oxo-ethylsulfanyl)-ethylcarbamoyl]-2-{4-[2-(3,4-dihydroxy-phenyl)-vinyl]-benzoylamino}-butyric acid.

Example 22

Formula Ia where A is 5-Methyl-[1,3,4]thiadiazol-2-yl, R is Ethyl, and X is S

A solution of 5-methyl-1,3,4-thiadiazole-2-thiol (264 mg, 2 mmol) and ethyl bromopyruvate (0.264 mL, 2.1 mmol) in methylene chloride (10 mL) and acetonitrile (10 mL) was stirred at 20° C. for 3 hours under nitrogen. The precipitates were filtered, washed with methylene chloride, and dried under vacuum. This gave the expected product, 3-(5-methyl-[1,3,4]thiadiazol-2-ylsulfanyl)-2-oxo-propionic acid ethyl ester (450 mg, yield 69%) as a solid. $^1$H-NMR (300 Hz, D$_3$COD and d$_6$-DMSO) δ (ppm): 4.22 (q, J=7.1 Hz, 2H), 3.78 (d, J=14.1 Hz, 1H), 3.71 (d, J=14.1 Hz, 1H), 2.74 (s, 3H), 1.27 (t, J=7.1 Hz, 3H).

Example 23

Formula Ia where A is 5-Chloro-benzothiazol-2-yl, R is Ethyl, and X is S

A solution of 5-chloro-2-mercaptobenzothiozole (403 mg, 2 mmol) and ethyl bromopyruvate (0.264 mL, 2.1 mmol) in methylene chloride (10 mL) and acetonitrile (30 mL) was shaken at 20° C. for 3 hours under nitrogen. The obtained solid was filtered, washed with methylene chloride, dried under vacuum. This gave the expected product, 3-(5-chloro-benzothiazol-2-ylsulfanyl)-2-oxo-propionic acid ethyl ester (425 mg, yield 54%) as a solid. $^1$H-NMR (300 Hz, D$_3$COD and d$_6$-DMSO) δ (ppm): 7.92 (d, J=8.6 Hz, 1H), 7.90 (d, J=2.1 Hz, 1H), 7.40 (dd, J=2.1 Hz, J=8.6 Hz, 1H), 4.20 (q, J=2.1 Hz, J=7.1 Hz, 2H), 3.96 (d, J=13.1 Hz, 1H), 3.86 (d, J=13.1 Hz, 1H), 1.23 (t, J=7.1 Hz, 3H).

Example 24

Formula Ia where A is 4,5-Dihydro-thiazol-2-yl, R is Ethyl, and X is S

A solution of 2-mercaptothiazole (238 mg, 2 mmol) and ethyl bromopyruvate (0.264 mL, 2.1 mmol) in methylene chloride (7 mL) was shaken at 20° C. for 3 hours under nitrogen. The obtained solid was filtered, washed with methylene chloride, and dried under vacuum. This gave the expected product, 3-(4,5-dihydro-thiazol-2-ylsulfanyl)-2-oxo-propionic acid ethyl ester (440 mg, yield 71%) as a solid. $^1$H-NMR (300 Hz, D$_3$COD) δ (ppm): 4.63 (d, J=13.1 Hz, 1H), 4.30–4.15 (m, 6H), 4.10 (d, J=13.1 Hz, 1H), 1.34 (t, J=7.1 Hz, 3H). MS (ESI) m/z: 234 (M+H, 100).

Example 25

Preparation of 2-hydroxy-4-(1-methyl-1H-imidazol-2-ylsulfanyl)-2,3-dihydro-furan-2,5-dicarboxylic acid diethyl ester A solution of 2-mercapto-1-methylimidazole (228 mg, 2 mmol), ethyl bromopyruvate (0.266 mL, 2.1 mmol), and imidazole (150 mg, 2.2 mmol) in methylene chloride (6 mL) and acetone (2 mL) was shaken at 20° C. under nitrogen for 4 hour. The solvents were evaporated under vacuum. The residue was treated with ethyl acetate and the liquid layer was discarded. The residue was then dissolved in methylene chloride. The solution was washed with aqueous sodium bicarbonate solution and water before dried over magnesium sulfate. Evaporation and chromatography (silica gel, methylene chloride-methanol 100:3 to 100:10 as the eluents) gave 20 mg of product. $^1$HNMR (300 Hz, Cl$_3$CD) δ (ppm): 8.13 (br. s, 1H), 7.01 (d, J=1.3 Hz, 1H), 6.91 (d, J=1.3 Hz, 1H), 4.65 (d, J=10.4 Hz, 1H), 4.57 (d, J=10.4 Hz, 1H), 4.35 (q, J=7.1 Hz, 2H), 4.09 (q, J=7.1 Hz, 2H), 3.69 (s, 3H), 1.38 (t, J=7.1 Hz, 3H), 1.21 (t, J=7.1 Hz, 3H). $^{13}$CNMR (75 Hz, Cl$_3$CD) δ (ppm): 171.2, 159.6, 147.5, 138.9, 128.8, 122.8, 117.2, 85.8, 80.3, 62.2, 62.1, 34.0, 14.2, 14.1. MS (ESI) m/z 343 (M+1, 100), 365 (M+Na, 7).

Example 26

Preparation of 2,2-Dimethyl-3,4-dihydro-2H-[1,4]thiazine-3,5-dicarboxylic acid

To a solution of L-penicillamine (298 mg, 2.0 mmol) in water (5 mL) and acetonitrile (5 mL) was added ethyl 3-bromopyruvate (0.25 mL, 390 mg, 2.0 mmol) slowly. To the resulted mixture was added sodium bicarbonate aqueous solution till the pH about 5. Acetonitrile was removed under vacuum and some more water was added. The solution was extracted with methylene chloride. The water phase was separated and freeze-dried under high vacuum. The residue was chromatographed (silica gel, methylene chloride-methanol-acetic acid 100:5:0.3 to 100:10:0.3) to give 150 mg of product (yield 31%). $^1$HNMR (300 Hz, D$_3$COD) δ (ppm) 6.17 (s, 1H), 4.23 (q, J=7.1 Hz, 2H), 3.79 (s, 1H), 1.48 (s, 3H), 1.31 (t, J=7.1 Hz, 3H), 1.29 (s, 3H). $^{13}$CNMR (75 Hz, D$_3$COD) δ (ppm) 173.8, 164.0, 128.0, 102.4, 64.1, 62.2, 41.2, 28.3, 25.2, 14.7 ppm. MS (ESI) m/z 268 (M+Na, 100), 246 (M+1, 5).

Example 27

Preparation of 4-[2-[2-(Adamantan-1-ylmethoxycarbonyl)-2-oxo-ethylsulfanyl]-1-(carboxymethyl-carbamoyl)-ethylcarbamoyl]-2-amino-butyric acid A solution of 10 mmol of 1-admantan-1-yl-methanol, 5 mmol of bromo pyruvic acid, 20 mg of TsOH in 80 mL of benzene was heated to reflux under azeotropic condition for 6 to 12 h under nitrogen atmosphere. After cooling, the solvent was removed under reduced pressure. The residue was chromatographed to afford the bromo pyruvate ester intermediate.

The above prepared pyruvate ester intermediate(1 mmol) was dissolved in 5–10 mL of acetonitrile. This solution was then slowly added to a solution of 1 mmol of glutathione in 10 mL of deionized water under vigorous stirring. Upon the completion of the addition, the resulting mixture was stirred for 3–8 h. The reaction was quenched by adding 50 mL water and washed with ether (3×20 mL). The aqueous layer was filtered through a C18 pad and freeze-dried. The crude product was chromatographed using reverse phase column using a manual gradient from 100% water to 70/30 water/acetonitrile to afforded a white sticky solid. MS (ESI) m/z 542 (M+H, 100), 560 (M+H$_2$O, 40).

Example 28

Preparation of 1-[3-(2-Ethoxycarbonyl-2-oxo-ethylsulfanyl)-2-methyl-propionyl]-pyrrolidine-2-carboxylic acid This compound is prepared using similar procedure described in Example 4. $^1$H-NMR (300 Hz, D$_3$COD) δ (ppm) 6.37 (s, 0.35H), 4.43 (dd, 1H), 4.21 (q, 2H), 3.73 (m, 3H), 2.75–3.16 (m, 3H), 2.21 (m, 1H), 2.03 (m, 3H), 1.31 (t, 3H), 1.16 (dd, 3H). MS (ESI) m/z 332 (M+H, 100).

Example 29

29A. Preparation of 2-Amino-4-[1-carboxy-2-(2-ethoxycarbonyl-2-oxo-ethylsulfanyl)-ethylcarbamoyl]-butyric acid To a solution of degassed and nitrogen purged 1-carboxy-3-(1-carboxy-2-mercapto-ethylcarbamoyl)-propyl-ammonium; trifluoro-acetate (50 mg, 85%, 0.12 mmol) in 1:1 acetonitrile and water (2 mL) was added of ethyl bromo pyruvate (14.6 μL). The reaction was allowed to stir for 1 hour before it was stopped and extracted with ether. The water phase was then directly filtered through a short solid phase column and placed on the lyopholyzer overnight to yield white crystals (55 mg, 95% yield). $^1$HNMR (300 Hz, D$_3$COD) δ (ppm) 6.37 (s, 0.15H), 4.62 (m, 1H), 4.23 (q, 2H), 3.92 (m, 1H), 2.83–3.30 (m, 2.4H), 2.56 (m, 2H), 2.17 (m, 2H), 1.31 (t, 3H).

29B. Other Compounds of Formulae Ia and II

By following the procedures of Example 29A and substituting 1-carboxy-3-(1-carboxy-2-mercapto-ethylcarbamoyl)-propyl-ammonium; trifluoro-acetate with (2-amino-3-mercapto-propionylamino)-acetic acid and 2-amino-4-[1-(ethoxycarbonylmethyl-carbamoyl)-2-mercapto-ethylcarbamoyl]-butyric acid, respectively, there are obtained the following:

3-[2-Amino-2-(carboxymethyl-carbamoyl)-ethylsulfanyl]-2-oxo-propionic acid ethyl ester White crystals (97% yield). $^1$HNMR (300 MHz, D$_3$COD) δ (ppm): 6.42 (s, 0.36H), 4.61 (m, 1H), 4.14–4.27 (m, 4H), 4.01 (m, 1H), 3.95 (s, 2H), 2.80–3.20 (m, 2.56H), 2.60 (m, 2), 2.20 (m, 2H), 1.26 (tt, 6H).

2-Amino-4-[1-(ethoxycarbonylmethyl-carbamoyl)-2-(2-ethoxycarbonyl-2-oxo-ethylsulfanyl)-ethylcarbamoyl]-butyric acid White solid (41% yield). $^1$HNMR (300 MHz, D$_3$COD) δ (ppm): 6.42 (s, 0.36H), 4.38 (dd, 1H), 4.28 (q, 2H), 2.95–3.54 (m, 2H), 1.27 (t, 3H). MS (ESI) m/z 293 (M+H, 100).

Example 30

2-Amino-4-[1-(carboxymethyl-carbamoyl)-2-(2-ethoxycarbonyl-2-hydroxyimino-ethylsulfanyl)-ethylcarbamoyl]-butyric acid 30A. Formula Ib where A is γ-Glu-CysX-Gly, W=NOR$^a$ where R$^a$ is H, and Z=OR where R is Ethyl 2-Amino-4-[1-(carboxymethyl-carbamoyl)-2-(2-ethoxycarbonyl-2-oxo-ethylsulfanyl)-ethylcarbamoyl]-butyric acid (1.0 mmol) was dissolved in 10 mL water, to which was added, at ambient temperature, a solution of (1.2 mmol, 1.2 eq) hydroxylamine hydrochloride. The mixture was agitated for 24 hrs. LC/MS of the reaction aliquot indicated the completion of the reaction. The mixture was then loaded onto a C18 reversed-phase column and eluted with acetonitrile and water, each containing 0.2% TFA (0 to 10 min, 5% acetonitrile; 10 to 50 min, 60% acetonitrile; 60 to 70 min, 100% acetonitrile). The fractions containing pure compound were pooled, vacuum distilled at 30° C. to one fourth of the volume and lyophilized to obtain the corresponding oxime as its TFA salt.

The oxime TFA salt (1.0 mmol) in 20 mL of water was treated with 1.2 mmols of dilute (1.0 M) HCl at 0° C. and the resulting clear solution was freeze-dried to obtain the desired title compound, 2-amino-4-[1-(carboxymethyl-carbamoyl)-2-(2-ethoxycarbonyl-2-hydroxyimino-ethylsulfanyl)-ethylcarbamoyl]-butyric acid, as a white solid. $^1$H NMR (D$_2$O): δ 1.28 (t, J=6.0 Hz, 3H), 2.10–2.27 (m, 2H), 2.50–2.59 (m, 2H), 2.82–3.06 (m, 2H), 3.64 (q, J=15.0 Hz, 2H), 3.97 (s, 2H), 4.06 (t, J=6.0 Hz, 1H), 4.29 (q, J=6.0 Hz), 4.58–4.64 (m, 1H). MS (ESI) m/z: 437 (M+H, 100%).

30B. Formula Ib where A is γ-Glu-CysX-Gly, W=NOR$^a$ where R$^a$ is H, and Z=OR where R is n-Butyl Similarly, by following the procedure of Example 30A and substituting 2-amino-4-[1-(carboxymethyl-carbamoyl)-2-(2-ethoxycarbonyl-2-oxo-ethylsulfanyl)-ethylcarbamoyl]-butyric acid with 2-amino-4-[2-(2-butoxycarbonyl-2-oxo-ethylsulfanyl)-1-(carboxymethyl-carbamoyl)-ethylcarbamoyl]-butyric acid there is obtained the following compound: 2-Amino-4-[2-(2-butoxycarbonyl-2-hydroxyimino-ethylsulfanyl)-1-(carboxymethyl-carbamoyl)-ethylcarbamoyl]-butyric acid; compound with HCl; $^1$H NMR (D$_2$O): δ 0.60–0.75 (m, 3H), 1.05–1.22 (m, 2H), 1.40–1.55 (m, 2H), 1.92–2.15 (m, 2H), 2.35–2.55 (m, 2H), 2.26–2.27 (m, 1H), 2.80–2.92 (m, 1H), 3.43 (q, J=12 Hz, 2H), 3.80 (s, 2H), 3.85–3.99 (m, 1H), 4.01–4.15 (m, 2H), 4.40–4.55 (m, 1H). MS(ESI) m/z: 465 (M+H, 100%), 466 (M+2H, 25%).

30B. Formula Ib Varying $R^a$

Similarly, by following the procedure of Example 30A and substituting hydroxylamine HCl with another substituted hydroxylamine there are obtained the following compounds:

2-Amino-4-[1-(carboxymethyl-carbamoyl)-2-(2-ethoxycarbonyl-2-methoxyimino-ethylsulfanyl)-ethylcarbamoyl]-butyric acid; $^1$H NMR (D$_2$O): δ 1.28 (t, J=9.0 Hz, 3H), 2.10–2.23 (m, 2H), 2.51–2.59 (m, 2H), 2.70–2.89 (m, 1H), 2.95–3.05 (m, 1H), 3.57–3.64 (m, 2H), 3.84 (s, 1H), 3.88–4.16 (m, 6H), 4.32 (q, J=9.0 Hz, 2H), 4.54–4.0 (m, 1H).

2-Amino-4-[1-(carboxymethyl-carbamoyl)-2-(2-ethoxycarbonyl-2-phenoxyimino-ethylsulfanyl)-ethylcarbamoyl]-butyric acid; compound with HCl; $^1$H NMR (D$_2$O): δ 1.15 (t, J=6.9 Hz, 3H), 2.0–2.14 (m, 2H), 2.21–2.50 (m, 2H), 2.65–2.80 (m, 2H), 2.81–2.98 (m, 2H), 3.6 (brs, 2H), 3.65–3.99 (m, 3H), 4.10–4.21 (m, 2H), 4.45–4.60 (m, 1H), 6.84–7.30 (m, 5H). MS(ESI) m/z: 513 (M+H, 100%), 514 (M+2H, 30%).

2-Amino-4-[2-(2-benzyloxyimino-2-ethoxycarbonyl-ethylsulfanyl)-1-(carboxymethyl-carbamoyl)-ethylcarbamoyl]-butyric acid; compound with HCl; $^1$H NMR (D$_2$O): δ 1.05 (t, J=9.0 Hz, 3H), 1.99–2.20 (m, 2H), 2.31–2.50 (m, 2H), 2.52–2.71 (m, 2H), 2.73–2.97 (m, 2H), 3.20–3.48 (m, 2H), 3.60–4.15 (m, 5H), 4.31–4.50 (m, 1H), 5.03 (s, 2H), 6.95–7.20 (m, 5H). MS(ESI) m/z: 527 (M+H, 100%), 528 (M+2H, 30%).

2-Amino-4-{1-(carboxymethyl-carbamoyl)-2-[2-ethoxycarbonyl-2-(4-nitro-benzyloxyimino)-ethylsulfanyl]-ethylcarbamoyl}-butyric acid; $^1$H NMR (D$_2$O): δ 1.08 (t, J=6 Hz, 3H), 2.0–2.20 (m, 2H), 2.35–2.60 (m, 2H), 2.62–2.76 (m, 1H), 2.80–3.10 (m, 1H), 3.40–3.61 (m, 2H), 3.70–4.21 (m, 5H), 4.50 (brs, 1H), 5.16 (s, 2H), 7.27 (d, J=9.0 Hz, 2H), 7.80 (d, J=9.0 Hz, 2H). MS(ESI) m/z: :572 (M+H, 100%), 573 (M+2H, 30%).

4-[2-(2-Allyloxyimino-2-ethoxycarbonyl-ethylsulfanyl)-1-(carboxymethyl-carbamoyl)-ethylcarbamoyl]-2-amino-butyric acid; compound with di-HCl; $^1$H NMR (D$_2$O): δ 1.20 (t, J=7.2 Hz, 3H), 2.08–2.20 (m, 2H), 2.45–2.60 (m, 2H), 2.65–2.80 (m, 1H), 2.90–3.06 (m, 1H), 3.50–3.64 (m, 2H), 3.90 (s, 2H), 4.10 (t, J=6.9 Hz, 1H), 4.22 (q, J=7.2 Hz, 2H), 4.49–4.54 (m, 1H), 4.70 (d, J=7.0 Hz, 2H), 5.15–5.30 (m, 2H), 5.80–6.10 (m, 1H). MS(ESI) m/z: 477 (M+H, 100%), 478 (M+2H, 30%).

2-Amino-4-[2-(2-tert-butoxyimino-2-ethoxycarbonyl-ethylsulfanyl)-1-(carboxymethyl-carbamoyl)-ethylcarbamoyl]-butyric acid; compound with di-HCl; $^1$H NMR (D$_2$O): δ 1.10–1.20 (m, 12H), 2.03–2.25 (m, 2H), 2.40–2.56 (m, 2H), 2.63–2.75 (m, 1H), 2.90–3.16 (m, 1H), 3.56–3.78 (m, 2H), 3.88 (s, 2H), 4.20 (t, J=6.9 Hz, 1H), 4.30 (q, J=7.2 Hz, 2H), 4.40–4.56 (m, 1H). MS(ESI) m/z: 493 (M+H, 100%), 494 (M+2H, 30%).

2-Amino-4-[1-(carboxymethyl-carbamoyl)-2-(2-ethoxycarbonyl-2-ethoxyimino-ethylsulfanyl)-ethylcarbamoyl]-butyric acid; compound with di-HCl; $^1$H NMR (D$_2$O): δ 1.15 (t, J=7.2 Hz, 3H), 1.19 (t, J=7.2 Hz, 3H), 1.10–1.30 (m, 2H), 1.50–1.62 (m, 2H), 1.72–1.87 (m, 1H), 2.0–2.10 (m, 1H), 2.61 (d, J=6 Hz, 2H), 2.96 (s, 2H), 3.10 (t, J=9.0, 1H), 3.21–3.34 (m, 4H), 3.55–3.26 (m, 1H). MS(ESI) m/z: 465 (M+H, 100%), 466 (M+2H, 30%).

30C. Formula Ib Varying R and $R^a$

Similarly, by following the procedure of Example 30A and substituting 2-amino-4-[1-(carboxymethyl-carbamoyl)-2-(2-ethoxycarbonyl-2-oxo-ethylsulfanyl)-ethylcarbamoyl]-butyric acid with 2-amino-4-[2-(2-butoxycarbonyl-2-oxo-ethylsulfanyl)-1-(carboxymethyl-carbamoyl)-ethylcarbamoyl]-butyric acid and hydroxylamine HCl with another substituted hydroxylamine there are obtained the following compounds:

2-Amino-4-[2-(2-butoxycarbonyl-2-methoxyimino-ethylsulfanyl)-1-(carboxymethyl-carbamoyl)-ethylcarbamoyl]-butyric acid; $^1$H NMR (DMSO-d$_6$): δ 0.90 (t, J=6.0 Hz, 3H), 1.25–1.42 (m, 2H), 1.5–1.72 (m, 2H), 1.95–2.14 (m, 2H), 2.20–2.80 (m, 4H), 2.82–3.03 (m, 1H), 3.4–3.69 (m, 3H), 3.7–3.82 (m, 2H), 3.85–4.0 (m, 4H), 4.12–4.25 (m, 2H), 4.46–4.65 (m, 1H). MS(ESI) m/z: 479 (M+H, 100%), 480 (M+2H, 30%)

2-Amino-4-[2-(2-benzyloxyimino-2-butoxycarbonyl-ethylsulfanyl)-1-(carboxymethyl-carbamoyl)-ethylcarbamoyl]-butyric acid; $^1$H NMR (DMSO-d$_6$): δ 0.90 (t, J=6.0 Hz, 3H), 1.30–1.45 (m, 2H), 1.52–1.70 (m, 2H), 2.10 (brs, 2H), 2.30–2.55 (m, 2H), 2.66–2.81 (m, 1H), 2.90–3.05 (m, 1H), 3.50–3.75 (m, 2H), 3.77–3.81 (m, 2H), 3.87 (brs, 1H), 4.10–4.23 (m, 2H), 4.45–4.68 (m, 1H), 5.28 (s, 3H), 7.30 (brs, 5H). MS(ESI) m/z: 555 (M+H, 100%), 556 (M+2H, 30%)

Example 31

Alternative Synthesis of 2-Amino-4-[1-(carboxymethyl-carbamoyl)-2-(2-ethoxycarbonyl-2-hydroxyimino-ethylsulfanyl)-ethylcarbamoyl]-butyric acid A mixture of bromopyruvic acid ethyl ester (390 mg) and hydroxyamine hydrochloride (1.05 eq) was stirred for 3 h at rt. The white solid was filtered and washed with water and dried (420 mg). To glutathione (307 mg) in degassed water (10 mL) was added above made oxime, 3-bromo-2-hydroxyimino-propionic acid ethyl ester (1 eq) in small portions. After 3 h, the reaction was washed with EtOAc (10 mL) and freeze-dried to afford 2-amino-4-[1-(carboxymethyl-carbamoyl)-2-(2-ethoxycarbonyl-2-hydroxyimino-ethylsulfanyl)-ethylcarbamoyl]-butyric acid as a fluffy white solid (179–6, 410 mg). $^1$H NMR (D$_2$O): δ 1.28 (t, J=6.0 Hz, 3H), 2.10–2.27 (m, 2H), 2.50–2.59 (m, 2H), 2.82–3.06 (m, 2H), 3.64 (q, J=15.0 Hz, 2H), 3.97 (s, 2H), 4.06 (t, J=6.0 Hz, 1H), 4.29 (q, J=6.0 Hz), 4.58–4.64 (m, 1H).

Example 32

1-{3-[2-(4-Amino-4-carboxy-butyrylamino)-2-(carboxymethyl-carbamoyl)-ethylsulfanyl]-2-oxo-propionyl}-pyrrolidine-2-carboxylic acid methyl ester 32A. Formula Ic where A is γ-Glu-CysX-Gly, W is =O, and Z is NR$^b$R$^c$ Forming a 5-Membered Acyl-substituted Ring To a solution of proline HCl salt (452 mg, 3.5 mmol) in a mixed solvent of 3 mL of acetonitrile and 5 mL of DCM in an ice bath was added dropwise a chilled triethylamine solution (353 mg, 3.5 mmol) with stirring. Upon completion of the triethylamine, the resulting suspension was allow to stir for 5 min and stored in the ice bath.

To 740 mg (4 mmol) of bromopyruvic acid dissolved in 5 mL of acetonitrile in an ice bath was added slowly the above prepared amino acid. Upon the completion of the amino acid addition, EDC (1-(3-dimethylaminopropyl)-3-ethylcarbodiimide hydrochloride)(806 mg, 4.2 mmol) was added to the mixture in small portions with vigorous stirring. The ice bath was removed and the mixture was allowed to stir for 20 min at rt. The reaction was quenched by adding 40 mL of water and the mixture was extracted with ethylacetate (3×30 mL). The organic layers were dried over $Na_2SO_4$ followed by solvent removal under reduced pressure. The residue was chromatographed using hexanes/ethylacetate (2:1) to afford a thick yellow oil (473 mg, 46%).

A solution of glutathione (2-amino-4[1-(carboxymethyl-carbamoyl)-2-mercapto-ethylcarbamoyl]-butyric acid)(368 mg, 1.2 mmol) in 5 mL of water was degassed through high vacuuming and argon purging. To this solution, the above prepared amide in 1.5 mL acetonitrile was added with vigorous stirring. The reaction was monitored with periodic MS checking until the glutathione was completely consumed (3 h). The reaction was quenched by adding 40 mL of water and the resulting mixture was extracted with ethylacetate (2×30 mL) and hexanes (2×20 mL). The aqueous solution was then filtered through a cotton pad and freeze-dried to afford 1-{3-[2-(4-amino-4-carboxy-butyrylamino)-2-(carboxymethyl-carbamoyl)-ethylsulfanyl]-2-oxo-propionyl}-pyrrolidine-2-carboxylic acid methyl ester; compound with HBr;as a yellow sticky solid (642 mg, 91%). $^1$H-NMR (D2O, 300 MHz) δ (ppm): 4.85–4.70 (m, 0.5H), 4.47–4.38 (m, 1.5H), 3.93 (t, J=6.5 Hz, 1H), 3.85 (s, 2H), 3.66–3.43 (m, 5.7H), 2.91–2.63 (m, 2H), 2.44 (m, 2H), 2.20–1.80 (m, 6H; MS(ESI) m/z: 505 (M+H$^+$, 100).

32B. Formula Ic Varying NR$^b$ R$^c$

Similarly, by following the procedure of Example 32A and substituting proline with another heterocyclic amine there is obtained the following compounds:

2-Amino-4-{1-(carboxymethyl-carbamoyl)-2-[3-(4-methyl-piperidin-1-yl)-2,3-dioxo-propylsulfanyl]-ethylcarbamoyl}-butyric acid. $^1$H-NMR (D2O, 300 MHz) δ (ppm): 4.51 (m, 1H), 4.17–4.13 (m, 1H), 3.95–3.91 (m, 3H), 3.71–3.60 (m, 1.6H), 3.55–3.42 (m, 1H), 3.09 (m, 1H), 2.98–2.90 (m, 1H), 2.85–2.72 (m, 2H), 2.48 (m, 2H), 2.13 (m, 2H), 1.70–1.57 (m, 3H), 1.06 (m, 2H), 0.85–0.83 (m, 3H). MS(ESI) m/z: 475 (M+H$^+$, 100).

2-Amino-4-[1-(carboxymethyl-carbamoyl)-2-(2,3-dioxo-3-pyrrolidin-1-yl-propylsulfanyl)-ethylcarbamoyl]-butyric acid; $^1$H-NMR (D2O, 300 MHz) δ (ppm): 4.56 (dd, J=8.2, 5.1 Hz, 1H), 4.04(t, J=6.6 Hz, 1H), 3.98 (s, 2H), 3.79 (s, 1H), 3.61 (t, J=5.6 Hz, 2H), 3.46 (t, J=5.6 Hz, 2H), 3.00 (dd, J=14.0, 5.1 Hz, 1H), 2.87 (dd, J=14.0, 8.7Hz, 1H), 2.56 (m, 2H), 2.19 (m, 2H), 1.89 (m, 4H). MS(ESI) m/z: 447 (M+H$^+$, 100).

2-Amino-4-[1-(carboxymethyl-carbamoyl)-2-(3-morpholin-4-yl-2,3-dioxo-propylsulfanyl)-ethylcarbamoyl]-butyric acid; MS(ESI) m/z: 463 (M+H$^+$, 100).

2-Amino-4-[1-(carboxymethyl-carbamoyl)-2-(2,3-dioxo-3-piperidin-1-yl-propylsulfanyl)-ethylcarbamoyl]-butyric acid; $^1$H-NMR (D2O, 300 MHz) δ (ppm): 4.49 (dd, J=8.3, 5.0 Hz, 1H), 3.69–3.61 (m, 3.5H), 3.41 (t, J=5.7 Hz, 2H), 3.28 (t, J=5.5 Hz, 2H), 2.92 (dd,J=14.0, 5.0 Hz, 1H), 2.77 (dd,J=14.0, 8.6 Hz, 1H), 2.39 (m, 2H), 2.01 (q, J=7.3 Hz, 2H), 1.57–1.43 (m, 6H). MS(ESI) m/z: 461 (M+H$^+$, 100).

Example 33

2-Amino-4-[1-(carboxymethyl-carbamoyl)-2-(2-dimethylcarbamoyl-2-oxo-ethylsulfanyl)-ethylcarbamoyl]-butyric acid 33A. Formula Ic where A is γ-Glu-CysX-Gly. W is =O, and Z is NR$^b$R$^c$ where R$^b$ and R$^c$ are Methyl To 185 mg (1 mmol) of bromopyruvic acid dissolved in 2 mL of DMF cooled in a ice bath, was added slowly a solution of N,N-dimethylamine in DCM (43 mg in 2 mL). The ice bath was removed and the mixture was allowed to warm to room temperature. To this mixture was simultaneously added Bop-Cl (Bis(2-oxo-3-oxasolidinyl) phosphonic chloride) (279 mg, 1.1 mmol) and triethylamine (106 mg, 1.05 mmol) with triethylamine addition slightly ahead over a period of 15 min. Upon the completion of the reagent addition, the reaction was allowed to stir for another 25 min before being quenched by addition of 40 mL water and 40 ethylacetate. After stirring for 2 min, the layers were separated, the organic layer was washed with water (2×20 mL), and the combined aqueous layers were back-extracted with ethylacetate (40 mL). The combined organic layers were dried over $Na_2SO_4$ and concentrated. The crude product was chromatographed with EtOAc/Hexanes to afford a pale yellow oil (88 mg, 48%).

A solution of glutathione (170 mg, 0.55 mmol) in 2 mL of water was degassed through high vacuuming and argon purging. To this solution, amide (128 mg, 0.66 mmol, prepared as above) in 1 mL acetonitrile was added with vigorous stirring. The reaction was monitored with periodic MS checking until the GSH was completely consumed (1.5). The reaction was quenched by adding 30 mL of water and the resulting mixture was extracted with ethylacetate (2×20 mL) and hexanes (2×15 mL). The aqueous solution was then filtered through a cotton pad and freeze-dried to afford a pale yellow sticky solid of 2-amino-4-[1-(carboxymethyl-carbamoyl)-2-(2-dimethylcarbamoyl-2-oxo-ethylsulfanyl)-ethylcarbamoyl]-butyric acid hydrobromide salt (262 mg, 95% yield, 179–91). The above product was purified by RP-LC and converted to HCl salt using a 0.1 M HCl solution. The purified product was obtained as a pale yellow sticky solid. $^1$H-NMR (D2O, 300 MHz) δ (ppm): 4.45 (dd, J=8.3, 5.2 Hz, 1H), 3.94 (t, J=6.6 Hz, 1H), 3.86 (s, 2H), 3.66–3.64 (m, 1.6H), 2.92–2.71 (m, 2H), 2.90 (s, 3H), 2.84 (s, 3H), 2.53–2.36 (m, 2H), 2.18–1.99 (m, 2H).), MS(ESI) m/z: 421 (M+M$^+$, 100).

33B. Formula Ic Varying NR$^b$R$^c$

Similarly, by following the procedure of Example 33A and substituting of N,N-dimethylamine with another amine there are obtained the following compounds:

2-Amino-4-[1-(carboxymethyl-carbamoyl)-2-(2-diethylcarbamoyl-2-oxo-ethylsulfanyl)-ethylcarbamoyl]-butyric acid $^1$H-NMR (D2O, 300 MHz) δ (ppm): 4.45 (dd, J=8.4, 5.2 Hz, 1H), 3.92 (t, J=6.5 Hz, 1H), 3.85 (s, 2H), 3.66–3.64 (m, 1.7H), 3.27 (q, J=7.2 Hz, 2H), 3.19 (q, J=7.1 Hz, 2H), 2.92–2.71 (m, 2H), 2.44 (m, 2H), 2.08 (m, 2H), 1.07–0.97 (m, 6H). MS(ESI) m/z: 449 (M+H$^+$, 100).

2-Amino-4-(1-(carboxymethyl-carbamoyl)-2-{2-[2-(4-hydroxy-phenyl)-1-methoxycarbonyl-ethylcarbamoyl]-2-oxo-ethylsulfanyl}-ethylcarbamoyl)-butyric acid; $^1$H-NMR (D2O, 300 MHz) δ (ppm):7.13–7.07 (m, 5H), 6.81–6.76 (m, 2H), 6.29 (s, 0.1H), 4.67 (dd, J=8.8, 5.4 Hz, 1), 4.52–4.46 (m, 1H), 4.03 (t, J=6.3 Hz, 1H), 3.97 (s, 2H), 3.72–3.66 (m, 3.4H), 3.17 (dd, J=14.4, 5.0 Hz, 1H), 3.00–2.90 (m, 2H), 2.78–2.66 (m, 2H), 2.56–2.49 (m, 2H), 2.18 (m, 2H); MS(ESI) m/z: 571 (M+H$^+$, 100), 589 (M+H$_2$O+H$^+$, 45), 601 (M+MeOH+H$^+$, 32).

2-{3-[2-(4-Amino-4-carboxy-butyrylamino)-2-(carboxymethyl-carbamoyl)-ethylsulfanyl]-2-oxo-propionylamino}-3-methyl-pentanoic acid methyl ester $^1$H-NMR (D2O, 300 MHz) δ (ppm): 4.56 (dd, J=8.5, 5.1 Hz, 1H), 4.28–4.20(m, 1H), 3.85–3.82 (m, 3H), 3.66–3.61 (m, 3.4H), 2.99–2.71 (m, 3.1H), 2.46–2.39 (m, 2H), 2.09–2.03 (m, 2H), 1.90–1.84 (m, 1H), 1.35–1.25 (m, 1H), 1.15–1.02 (m, 1H), 0.79–0.71 (m, 6H). MS(ESI) m/z: 535 (M+H$^+$, 100), (M+H2O+H$^+$, 20), (M+MeOH+H$^+$, 40).

2-Amino-4-[1-(carboxymethyl-carbamoyl)-2-(2-octylcarbamoyl-2-oxo-ethylsulfanyl)-ethylcarbamoyl]- butyric acid; ¹H-NMR (D2O, 300 MHz) δ (ppm): 6.20 (s, 0.02H), 4.47–4.39 (m, 1H), 3.78–3.64 (m, 3H), 3.38 (m, 0.8H), 3.15–3.05 (m, 2H), 2.90–2.82 (m, 1H), 2.65–2.55 (m, 1H), 2.49 (m, 1 H), 2.32–2.25 (m, 2H), 1.95–1.84 (m, 2H), 1.46–1.37 (m, 2H), 1.28–1.15 (m, 10H), 0.83 (t, J=13 Hz, 3H). MS(ESI) m/z: 505 (M+H$^+$, 100), 523 (M+H$_2$O+H$^+$, 45), 537 (M+MeOH+H$^+$, 38).

2-Amino-4-[1-(carboxymethyl-carbamoyl)-2-(2-ethylcarbamoyl-2-oxo-ethylsulfanyl)-ethylcarbamoyl]-butyric acid; MS(ESI) m/z: 421 (M+H$^+$, 100)

2-Amino-4-{1-(carboxymethyl-carbamoyl)-2-[2-(1-methoxycarbonyl-2-phenyl-ethylcarbamoyl)-2-oxo-ethylsulfanyl]-ethylcarbamoyl}-butyric acid; ¹H-NMR (D2O, 300 MHz) δ (ppm): 7.23–7.09 (m, 5H), 6.15 (s, 0.05H), 4.63–4.58 (m, 1H), 4.48–4.33 (m, 1H), 3.93–3.89 (m, 1H), 3.86–3.80 (m, 2H), 3.61–3.43 (m, 3H), 3.21–3.12 (m, 1H), 2.97–2.87 (m, 1H), 2.84–2.55 (m, 3H), 2.44–2.36 (m, 2H), 2.1–2.02 (m, 2H); MS (ESI) m/z: 555 (M+H$^+$, 100), 573 (M+H$_2$O+H$^+$, 36), 587 (M+MeOH+H$^+$, 85).

2-Amino-4-[1-(carboxymethyl-carbamoyl)-2-(2-cyclohexylcarbamoyl-2-oxo-ethylsulfanyl)-ethylcarbamoyl]-butyric acid; ¹H-NMR (D2O, 300 MHz) δ (ppm): 6.18 (s, 0.05H), 4.44–4.39 (m, 1H), 3.94 (t, J=6.5 Hz, 1H), 3.85 (s, 2H), 3.65 (s, 0.6H), 3.54–3.41 (m, 1H), 2.97–2.71 (m, 3H), 2.47–2.41 (m, 2H), 2.12–2.03 (m, 2H), 1.66–1.1.42 (m, 5H), 1.22–0.97 (m, 5H); MS(ESI) m/z: 475 (M+H$^+$, 100), 493 (M+H$_2$O+H$^+$, 52), 507 (M+MeOH+H$^+$, 15).

2-Amino-4-[2-(2-benzylcarbamoyl-2-oxo-ethylsulfanyl)-1-(carboxymethyl-carbamoyl)-ethylcarbamoyl]-butyric acid; ¹H-NMR (D2O, 300 MHz) δ (ppm):7.26–7.16 (m, 5H), 4.69–4.36 (m, 1H), 4.30–4.27 (m, 2H), 3.91 (t, J=13.2 Hz, 1H), 3.81 (s, 2H), 3.64 (s, 0.5H), 2.86–2.80 (m, 2H), 2.70–2.64 (m, 1H), 2.06 (m, 2H); MS(ESI) m/z: 483 (M+H$^+$, 100), 501 (M+H$_2$O+H$^+$, 64), 515 (M+MeOH+H$^+$, 52).

2-Amino-4-[1-(carboxymethyl-carbamoyl)-2-(2-hexylcarbamoyl-2-oxo-ethylsulfanyl)-ethylcarbamoyl]-butyric acid; ¹H-NMR (D2O, 300 MHz) δ (ppm): 6.19 (s, 0.02H), 4.47–4.40 (m, 1H), 3.90–3.85 (m, 3H), 3.65 (d, J=2.5 Hz, 0.6H), 3.15–3.05 (m, 2H), 2.97–2.71 (m, 3H), 2.46–2.40 (m, 2H), 2.11–2.01 (m, 2H), 1.39–1.32 (m, 2H), 1.18–1.08 (m, 6H), 0.72–0.68 (m, 3H). MS(ESI) m/z: 477 (M+H$^+$, 100), 495 (M+H$_2$O+H$^+$, 68), 509 (M+MeOH+H$^+$, 70).

Example 34

2-Amino-4-[1-(carboxymethyl-carbamoyl)-2-(2-hydroxyimino-3-oxo-3-piperidin-1-yl-propylsulfanyl)-ethylcarbamoyl]-butyric acid To a cooled (0° C.) solution of 3-bromopyruvic acid (0.835 g, 0.005 mol) in acetonitrile (8 mL) was added a pre-cooled (0° C.) solution of piperidine (0.341 g, 0.004 mol) in CH$_2$Cl$_2$ (3 mL) slowly drop-wise during 5 min. EDC was then added pinch-wise during 5 min. and the mixture was stirred at the same temperature for 10 min. and the mixture slowly warmed to room temperature. Quenching of the reaction with 10 mL of cold water, extraction with ethylacetate (2×25 mL) followed by concentration and flash chromatography over silica gel afforded the desired product, 3-bromo-1-piperidin-1-yl-propane-1,2-dione as a brown oil. The product was carried forward to the next step without assessing yield and purity.

To a cooled (0° C.) solution of glutathione (500 mg, 1.595 mmol) in water (15 mL) was added bromopyruvic amide (obtained from the above reaction) in acetonitrile (10 mL) slowly drop-wise during 5 min. and the mixture stirred at the same temperature for 1 hr and slowly warmed to room temperature and continued stirring overnight. LC/MS indicated the formation of the desired product, 2-amino-4-[1-(carboxymethyl-carbamoyl)-2-(2,3-dioxo-3-piperidin-1-yl-propylsulfanyl)-ethylcarbamoyl]-butyric acid. The mixture was purified by MPLC to obtain a pale yellow solid as its TFA salt 400 mg, (43.7%).

2-Amino-4-[1-(carboxymethyl-carbamoyl)-2-(2,3-dioxo-3-piperidin-1-yl-propylsulfanyl)-ethylcarbamoyl]-butyric acid as its TFA salt (400 mg, 0.696 mol) was dissolved in 8 mL of water to which was added 1.3 eq. of solid NH$_2$OH.HCl at 0° C. and the homogeneous solution was left standing over-night. LC/MS indicated that the reaction was incomplete. An additional 1 eq. of NH$_2$OH.HCl was added at room temperature and the homogeneous solution was left standing overnight. LC/MS indicated complete conversion of the starting amide to the corresponding oxime. The aqueous mixture was then passed through reversed-phase C18 column using water and acetonitrile mixture as gradient eluent. The pure fractions were pooled, concentrated under vacuum at room temperature to one fourth of the volume and finally freeze-dried to obtain 2-amino-4-[1-(carboxymethyl-carbamoyl)-2-(2-hydroxyimino-3-oxo-3-piperidin-1-yl-propylsulfanyl)-ethylcarbamoyl]-butyric acid as its TFA salt (390 mg, 95.1%).

To a cooled (0° C.) solution of the above TFA salt (390 mg, 0.662 mmol) in 10 mL of water was added a pre-cooled aqueous 1N HCl (0.662 mol) and the homogeneous solution was freeze-dried to obtain the HCl salt of the product as a white solid (380 mg, quantitative). The structure was in agreement with its LC/MS and 1H NMR data. ¹H NMR (D$_2$O) δ 4.57–4.40 (m, 1H), 3.59 (t, 6.6 Hz, 1H), 3.58 (s, 2H), 3.52–3.25 (brs, 1H), 2.59–2.51 (m, 2H), 2.45–2.32 (m, 2H), 2.10–1.59 (m, 2H), 1.45 (brs, 6H).

Example 35

3-[1-(Carboxymethylcarbamoyl)ethylsulfanyl]-2-hydroxyacrylic acid ethyl ester

35A. Formula Ia where A is N-(propionyl)glycine, X is S, and Z is —O-Ethyl

A solution of N-(2-mercaptopropionyl)glycine (1.17 g, 7.17 mmol) and ethyl bromopyruvate (1 mL, 7.17 mmol, 90% purity) in acetonitrile (30 mL) was stirred at room temperature for 3 h. After removal of the solvent, the residue was dissolved in a mixed solvent of ethanol (15 mL) and water (15 mL). After the pH was adjusted to 7–8 with satd. NaHCO$_3$ solution, the mixture was stirred at room temperature overnight. The mixture was acidified to pH 1–2 with concentrated hydrochloric acid and then rotary evaporated to dryness. The residue was purified by column chromatography eluted with EtOAc giving 3-[1-(carboxymethylcarbamoyl)ethylsulfanyl]-2-hydroxyacrylic acid ethyl ester as yellow solid (1.06 g, yield 53.3%). ¹H NMR (CDCl$_3$, 300.16 MHz) δ (ppm): 9.10 (broad s, 1H), 7.22 (d, J=0.9 Hz, 1H), 4.62 (d, J=17.7 Hz, 1H), 4.53 (d, J=17.7 Hz, 1H), 4.28 (q, J=7.1 Hz, 2H), 3.47 (qd, J=6.2 & 0.9 Hz, 1H), 1.48 (d, J=6.2 Hz, 3H) and 1.30 (t, J=7.1 Hz, 3H). ¹³C NMR (CDCl$_3$, 75.48 MHz) δ (ppm): 174.02, 165.84, 160.57, 130.27, 120.20, 62.04, 46.76, 37.11, 14.45 and 14.09. MS (ESI) m/z: 260 (M$^+$—OH, 100).

35B. Formula Ia where A is 2,3-Dihydroxy-propyl, X is S, and Z is —O-Ethyl

Similarly, by following the procedure of Example 35A and substituting N-(2-mercaptopropionyl)glycine with 3-mercapto-1,2-propanediol, there is obtained the following compound:

3-(2,3-dihydroxypropylsulfanyl)-2-hydroxyacrylic acid ethyl ester. $^1$H NMR (CDCl$_3$, 300.16 MHz) δ (ppm): 6.70 (d, J=1.1 Hz, 1H), 4.23 (q, J=7.1 Hz, 2H), 4.17–4.11 (m, 1H), 3.82 (d, J=5.1 Hz, 2H), 2.99–2.88 (m, 2H) and 1.30 (t, J=7.1 Hz, 3H). MS (ESI) m/z: 205 (M$^+$—OH, 100), 227 (M$^+$—H$_2$O+Na, 51) and 431 [2(M$^+$—H$_2$O)+Na, 29].

Example 36

2-Oxo-3-(4-oxo-3,4-dihydro-quinazolin-2-ylsulfanyl)-propionic acid ethyl ester

An homogeneous solution of 2-mercapto-3H-quinazolin-4-one (1.30 g, 7.17 mmol) and ethyl bromopyruvate (1 mL, 7.17 mmol, 90% purity) in DMF (30 mL) was stirred at room temperature for 6 h. Triethylamine (5 mL) was added to the solution and the mixture was stirred at room temperature for 36 h. The mixture was acidified to pH 1–2 with concentrated hydrochloric acid and then rotary evaporated to dryness. The residue was separated by column chromatography eluted with EtOAc giving the title compound as yellow solid (0.231 g, yield 11.0%). $^1$H NMR (DMSO-d$_6$, 300.16 MHz) δ (ppm): 8.05 (dd, J=7.9 & 1.4 Hz, 1H), 8.01 (s, 1H), 7.81 (td, J=8.3 & 1.5 Hz, 1H), 7.53 (d, J=8.2 Hz, 1H), 7.46 (td, J=7.5 & 1.4 Hz, 1H), 4.21 (q, J=7.1 Hz, 2H), 3.82 (d, J=12.2 Hz, 1H), 3.46 (d, J=12.2 Hz, 1H) and 1.18 (t, J=7.1 Hz, 3H). $^{13}$C NMR (DMSO-d$_6$, 75.48 MHz) δ (ppm): 168.06, 159.54, 159.26, 149.07, 135.98, 126.85, 126.74, 126.36, 119.09, 91.33, 62.79, 37.92 and 14.31. MS (ESI) m/z: 293 (M$^+$+H, 100).

Example 37

3-(Benzoselenazol-2-ylsulfanyl)-2-oxo-propionic acid ethyl ester

To a suspension of 2-mercaptobenzselenazole (418 mg, 2 mmol) in 4 mL of MeCN and 4 mL of dichloromethane with vigorous stirring was added dropwise, ethyl bromopyruvate (290 mg, 2 mmol). The resulting mixture was stirred for 5 h. It was allowed to settle for 30 min and then filtered. The solid was washed with EtOAc/hexanes (1:1, 2×8 mL) and dried in high vacuum to afford 3-(benzoselenazol-2-ylsulfanyl)-2-oxo-propionic acid ethyl ester as a white powder (582 mg, 89%). $^1$H-NMR (DMSO-d6, 300 MHz) δ (ppm): 8.14–8.10 (m, 1H), 7.95–7.92 (m, 0.7H), 7.75–7.73 (m, 0.3H), 7.52–7.45 (m, 1H), 7.36–7.30 (m, 1H), 7.07 (s, 0.7H), 4.69 (s, 0.6), 4.37–4.27 (m, 2H), 1.32 (t, J=7 Hz, 3H). MS(ESI) m/z: 330(M+H$^+$, 55), 348 M$^+$+H$_2$O, 58 ), 362 (M$^+$+MeOH, 100).

Example 38

Determination of Activity Utilizing Neuronal Cell Stress Assay

A. Isolation and Culture of Primary Hippocampal Neuronal Cells.

The following materials are employed:
Neurobasal/B27i: Neurobasal medium (available from Invitrogen, San Diego, Calif.) with 1× B27 supplement (Invitrogen), 0.5 μL-glutamine, 25 μM L-glutamic acid, and 1× Penicillin/Streptomycin.
Hank's Basic Salt Solution (HBSS, Ca/Mg-free) is prepared by preparing 1× Hanks CMF (Gibco) supplemented with HEPES (10 mM, pH 7.3), sodium bicarbonate (0.35%), 1× Penicillin/Streptomycin, and 1 mM MEM sodium pyruvate.
Poly-D-lysine (Sigma, St. Louis, Mo.), 50 μg/ml solution.
Sigmacote (Sigma, St. Louis, Mo.).
Plastic Culture Flasks (T75 cm$^2$) or 24-well cell culture plates treated with Poly-D-Lysine (Sigma, St. Louis, Mo.).

A pregnant female mouse (E18-E19) is euthanized with CO$_2$ followed by removal of the uterus, which is then placed in a sterile plastic petri dish. The embryos are removed from the sac, and the embryonic brains removed and immersed in cold (4° C.) Buffered Salt Solution (HBSS; Ca/Mg free; Life Technologies) in a small petri dish. Hippocampi are then removed from the brains under a dissecting microscope and placed on a paraffin-covered dish. The meninges are stripped away and the dissected hippocampi are collected in a small petri dish in HBSS. The hippocampi are transferred to a 15-ml centrifuge tube (normally 10–12 brains) filled with HBSS. The tube containing the brains is centrifuged at 1000 rpm for 2 min in a tabletop centrifuge. The supernatant is removed, 2 ml of HBSS is added to the hippocampi in the tube, and the resulting suspension is triturated 2 times each with long-tipped siliconized glass pipettes having progressively smaller apertures, starting with a pipette with a standard size opening (approximately 1.0 mm diameter), following with one having an aperture of half standard size (approximately 0.5 mm diameter), then with one having an aperture about one-half that size (0.25 mm diameter). The suspension is then centrifuged again at 1000 rpm for 2 min in a tabletop centrifuge, the supernatant is discarded, and 2 ml of Neurobasal/B27i (with antibiotics) is added to the tube. The trituration procedure described above is then repeated on this suspension.

The density of cells is determined on a small aliquot of cells using standard counting procedures and correcting for cell viability by trypan blue stain exclusion. Using this procedure, the expected yield is 3×10$^5$–6×10$^5$ cells/brain. Cells are then added to PDL-coated 24 well plates, flasks or MetTek dishes in Neurobasal/B27I at a density of about 1.5×10$^6$ cells (T75 flask) or about 100,000 cells/well of a 24-well plate. Plated cells are incubated at 37° C. in an atmosphere of 5% CO$_2$/95% O$_2$. Media is renewed after 3–4 days by replacing half of it with fresh Neurobasal/B27m medium, containing 5 μM cytosine arabinoside (Ara-C). Seven to eight days from the initial culture, the media is renewed again, by removing one-half or it and replacing with an equal amount of fresh Neurobasal/B27m medium (without Ara-C).

B. Hippocampal Anoxia-Reoxygenation Cell Death Assay.

This assay is used to induce ischemia by anoxia-reoxygenation in cultured hippocampal neuronal cells. Test compounds are added to assess potency and efficacy against ischemia-induced neuronal cell injury and cell death.

The following materials are employed:
Neurobasal media, NoG neurobasal media, B27 supplement and B27 Supplement minus AO (Invitrogen).
Neurobasal/B27 medium is prepared with 2× B27 minus AO supplement, 0.5 mM L-glutamine and 0.25× penicillin/streptomycin.
Cell Tracker Green was obtained from Molecular Probes and a fresh 5 μM solution was prepared from 10 mM stock just before use.
NoG-Neurobasal contains NoG neurobasal medium plus 0.5 mM glucose, 0.1 mM L-glutamine and 0.25× Penicillin/Streptomycin.
Primary hippocampal neuronal cells were prepared according to the methods described above and were cultured in poly-D-lysine coated 24 well plates for 10–11 days prior to use.
Deoxygenated LoG-Neurobasal medium (100 ml) is prepared by pre-equilibrating the medium in a T150 cm$^2$ flask in a hypoxic chamber overnight. Following pre-incubation under hypoxic conditions, the LoG-Neurobasal media is lightly bubbled with 100% $N_2$ for 30 min to completely deoxygenate the media. An additional 20 ml LoG-Neurobasal is pre-equilibrated in a T75 $cm^2$ flask and 100 ml Neurobasal/B27AO is incubated in a normal incubator (5% $CO_2$) overnight. Reoxygenated medium is prepared by placing medium overnight in the culture incubator (5% $CO_2$/95% $O_2$) prior to use.

Existing culture medium (Neurobasal/B27m) is removed from the cells by aspiration. Cells are washed once with 2 ml/well (24-well culture plates) of glucose free-BSS. Neurons are replenished 10–11 days after initial culture with deoxygenated LoG-Neurobasal (1 ml per well for each well of a 24-well plate). Test compounds are added directly to each well (3 concentrations of the compound plus positive control, each in triplicate). Most test compounds are dissolved in 100% DMSO; concentrations are adjusted such that the final concentration of DMSO in the cell media never exceeded 0.5%. Plates containing cells with test compounds are placed in a hypoxic chamber for 5 hr with plate lids ajar. For normoxia controls, pre-equilibrated normoxic LoG-Neurobasal medium is added to each well of cells, and the plate is replaced in the normal culture incubator for 5 hr. After 5 hr of hypoxia, the existing media is carefully aspirated off, and 2 mL of new, reoxygenated (pre-equilibrated) Neurobasal/B27AO is added to each well. The same test compounds (in the same the concentrations) are added back into the corresponding wells. Plates are placed in the cell culture incubator (5% $CO_2$/95% $O_2$) and reoxygenated for 20–24 hr. After reoxygenation for 20–24 hr, live neurons are quantitated using the cell tracker green fluorescence method, described below.

To test for cell viability, existing culture medium is aspirated from each well of the 24 well plates, and neurons are washed once with 2 ml of HBSS (pH 7.4, prewarmed to 30–37° C.). To each well is added one milliliter of 5 $\mu$M Cell Tracker Green fluorescent dye dissolved in HBSS. Plates are placed in the dark at room temperature for 15 minutes, and are then washed with two milliliters of HBSS. One milliliter of HBSS is then added to each well, and fluorescent cells are counted using a fluorescent microscope. Significantly increased cell viability compared to control cells is indicative of a protective compound.

Results

When tested as described above, compounds of the present invention, including:

2-amino-4-[1-(carboxymethyl-carbamoyl)-2-(2-hexyloxycarbonyl-2-oxo-ethylsulfanyl)-ethylcarbamoyl]-butyric acid, 2-amino-4-[1-(carboxymethyl-carbamoyl)-2-(2-ethoxycarbonyl-2-oxo-ethylsulfanyl)-ethylcarbamoyl]-butyric acid, 2-amino-4-[1-(carboxymethyl-carbamoyl)-2-(2-carboxy-2-oxo-ethylsulfanyl)-ethylcarbamoyl]butyric acid, 2-amino-4-[1-(carboxymethyl-carbamoyl)-2-(2-ethoxycarbonyl-2-oxo-ethylsulfanyl)-ethylcarbamoyl] butyric acid, 2-amino-4-[2-(2-butoxycarbonyl-2-methoxyimino-ethylsulfanyl)-1-(carboxymethyl-carbamoyl)-ethylcarbamoyl]-butyric acid or the HCl salt thereof, 2-amino-4-[2-(2-benzyloxyimino-2-butoxycarbonyl-ethylsulfanyl)-1-(carboxymethyl-carbamoyl)-ethylcarbamoyl]-butyric acid or the HCl salt thereof, 2-amino-4-[1-(carboxymethyl-carbamoyl)-2-(2-ethoxycarbonyl-2-hydroxyimino-ethylsulfanyl)-ethylcarbamoyl]-butyric acid, 2-amino-4-[2-(2-benzyloxyimino-2-ethoxycarbonyl-ethylsulfanyl)-1-(carboxymethyl-carbamoyl)-ethylcarbamoyl]-butyric acid or the HCl slat thereof, 2-amino-4-{1-(carboxymethyl-carbamoyl)-2-[2-ethoxycarbonyl-2-(4-nitro-benzyloxyimino)-ethylsulfanyl]-ethylcarbamoyl}-butyric acid, 2-Amino-4-{1-(carboxymethyl-carbamoyl)-2-[3-(4-methyl-piperidin-1-yl)-2,3-dioxo-propylsulfanyl]-ethylcarbamoyl}-butyric acid, 2-Amino-4-[1-(carboxymethyl-carbamoyl)-2-(2-hydroxyimino-3-oxo-3-piperidin-1-yl-propylsulfanyl)-ethylcarbamoyl]-butyric acid, 2-Amino-4-[1-(carboxymethyl-carbamoyl)-2-(2-diethylcarbamoyl-2-oxo-ethylsulfanyl)-ethylcarbamoyl]-butyric acid 2-Amino-4-[1-(carboxymethyl-carbamoyl)-2-(2,3-dioxo-3-piperidin-1-yl-propylsulfanyl)-ethylcarbamoyl]-butyric acid, 2-Amino-4-{1-(carboxymethyl-carbamoyl)-2-[2-(1-methoxycarbonyl-2-phenyl-ethylcarbamoyl)-2-oxo-ethylsulfanyl]-ethylcarbamoyl}-butyric acid, 2-Amino-4-[1-(carboxymethyl-carbamoyl)-2-(2-cyclohexylcarbamoyl-2-oxo-ethylsulfanyl)-ethylcarbamoyl]-butyric acid, 2-Amino-4-[2-(2-benzylcarbamoyl-2-oxo-ethylsulfanyl)-1-(carboxymethyl-carbamoyl)-ethylcarbamoyl]-butyric acid, 2-Amino-4-[1-(carboxymethyl-carbamoyl)-2-(3-morpholin-4-yl-2,3-dioxo-propylsulfanyl)-ethylcarbamoyl]-butyric acid, 3-(1H-benzoimidazol-2-ylsulfanyl)-2-oxo-propionic acid ethyl ester, 3-(5-nitro-benzoimidazol-2-ylsulfanyl)-2-oxo-propionic acid ethyl ester, and 3-(5-methoxy-benzoimidazol-2-ylsulfanyl)-2-oxo-propionic acid ethyl ester, provided protection against stressor-induced cell death in at least about 30% up to about 85% of the cells tested, at concentrations ranging from about 1 to about 350 $\mu$M.

Example 39

Myocyte Calcium-Contractility Assay

A. Isolation and Culture of Primary Neonate Myocytes.
The following materials are employed:

10× Heart Dissection Solution (HDS) contains the following components (g/l) in tissue grade water: NaCl, 68;HEPES, 47.6; $NaH_2PO_4$, 2; Glucose, 10; KCl, 4; $MgSO_4$, 1, pH adjusted to 7.4. Prior to filter sterilization of diluted (1×HDS) solution, 10 mg phenol red is added to each 500 milliliters of medium.

Transferrin and Bovine Insulin (available from Life Technologies) are resuspended at a concentration of 4 mg/ml in tissue culture grade water.

DMEM-F12-DMEMF12, powder, 1:1 containing glutamine and pyridoxine hydrochloride (available from Life Technologies). To one liter equivalent of the powder is added 2.43 g of sodium bicarbonate and 10 ml of 100× Penicillin/Streptomycin in 950 ml of tissue culture grade water with stirring. The pH is adjusted to 7.2 with 1M HCl and volume adjusted to 1 liter. The solution is filter sterilized, followed by the addition of 2.5 ml of 4 mg/ml Transferrin, 250 $\mu$l 4 mg/ml Insulin and 30.7 mg of bromodeoxyuridine.

DMEM-F12-5% FBS is also prepared for pre-coating the tissue culture plates and initial suspension of the cardiomyocyte pellet.

Collagenase solution—57.1 mg of collagenase is resuspended in 140 ml 1×HDS.

Tissue culture ware is pre-coated with DMEM-F12-5% FBS by incubating 50 μl per well of a 96-well plate and 0.5 ml per 24-well plate at 37° C.

Two-day old rat pups are removed from their mothers and placed in a sterile container. Pups are dipped quickly into 70% alcohol, then decapitated and the body placed in an empty sterile tissue culture dish. An incision is made starting at the neck and progressing towards the belly, cuffing through the sternum. The heart is removed and placed in a tissue culture dishes containing 1×HDS. The atria are trimmed, and the remaining ventricles are placed into a separate tissue culture dish containing 1×HDS, where they are sectioned into 3–4 pieces each. Ventricles are then transferred to a sterile 250 ml glass flask and the 1×HDS is removed. Twenty milliliters of pre-warmed collagenase solution is added to the ventricles, followed by incubation at 37° C. with shaking. After 20 minutes, the collagenase solution is removed and replaced with 20 ml fresh pre-warmed collagenase. Incubation is continued for an additional 20 minutes. At the end of the incubation, any tissue chunks are allowed to settle prior to removing the collagenase (containing the isolated cardiomyocytes) from the disrupted tissue pieces. The isolated myocytes are added to a 50 ml Falcon tube containing 2 ml Fetal Bovine Serum (FBS). The remaining tissue pieces are subjected to a second digestion by adding 20 ml fresh pre-warmed collagenase and incubating as above for 20 minutes. This second digest is then centrifuged at 1000 rpm for 5 minutes (tabletop centrifuge). The resulting supernatant is discarded, and the cell pellet is suspended with 4 ml FBS. The resulting cell suspension is placed in the incubator at 37° C. This step is repeated several additional times to harvest additional material.

Percoll gradients are prepared by adding 2.5 ml of 10×HDS to 22.5 ml of Percoll (Life Technologies) with mixing (Percoll Stock). Top Gradient solution (11 ml Percoll Stock and 14 ml 1×HDS) and Bottom Gradient solution (13 ml Percoll Stock and 7 ml 1×HDS) are prepared. Four milliliters of the Top Gradient solution is transferred into 6×15 ml sterile Falcon tubes. Three milliliters of the Bottom Gradient solution is placed in each tube by inserting a serological pipette to the bottom of the tube and slowly adding the liquid.

All the digests (6) are pooled in one 50 ml Falcon tube and centrifuged on a tabletop centrifuge at 1000 rpm for 10 minutes. The supernatant is discarded, and the cell pellet is resuspended in 12 ml of 1×HDS. Two milliliters of the cell suspension is added to the top of each gradient. The gradient tubes are then centrifuged at 3000 rpm for 30 minutes without braking in a Beckman Allegra 6 centrifuge (GH 3.8A rotor). Following centrifugation, the cells segregate into two sharp bands at the two interfaces. The lower band of the two bands is enriched for cardiomyocytes; there is also a cardiomyocyte pellet at the bottom of the tube. The upper band is enriched for fibroblasts and other non-cardiomyocytes. The upper portion of the gradient is aspirated down to just above the cardiomyocyte layer. The cardiomyocyte layer is then carefully removed along with the pellet, and the two fractions are pooled in a sterile 50 ml Falcon tube, along with corresponding fractions from additional gradient tube; then 1×HDS is added to a total volume of about 50 ml. The tube is centrifuged at 1000 rpm for 10 minutes. The supernatant is discarded and resuspended in 10 ml 1×HDS. A further 40 ml of 1×HDS is added and the centrifugation step is repeated. The cell pellet is resuspended carefully but thoroughly in 50 ml of DMEMF12-5% FBS.

A small aliquot of the cell suspension is counted in a hemocytometer. The DMEM/F12-FBS coating medium is aspirated from the tissue culture dishes. The cardiomyocytes are added to the dishes at a plating density of $7.5\times10^4$/well per 96-well in 200 μL and $6\times10^4$/well per 24-well in 1 ml. The cultures are incubated at 37° C. with 5% $CO_2$ overnight. The original medium is removed, and add fresh DMEM/F12-5% FBS is added to each culture, prior to incubation at 37° C. with 5% $CO_2$ for a further 48 hours, before use.

B. Contractility Assay

The following materials are employed:

Complete DMEM-F12: DMEM/F12, powder, 1:1 containing glutamine and pyridoxine hydrochloride (available from Life Technologies—Invitrogen Life Technologies, Carlsbad, Calif.). Powder sufficient to prepare one liter of buffer and 2.43 g of sodium bicarbonate is mixed into 950 ml of tissue culture grade water. The pH is adjusted to 7.2 with 1M HCl and the remaining water added to make 1 liter. Following filter sterilization, 10 ml of 100× Penicillin/Streptomycin, 2.5 ml of 4 mg/ml Transferrin, 250 μl 4 mg/ml Insulin and 30.7 mg of bromodeoxyuridine are added, and the mixture is incubated at 37° C. prior to use.

1 mM glucose in DMEM is made from DMEM without L-glutamine, without glucose, without sodium pyruvate (available from Life Technologies).

20 μM Fluo-4: Cell permanent AM ester of Fluo-4 (available as a dry powder to be stored at −20° C., from Molecular Probes—Eugene, Oreg.). This fluorescent dye is light sensitive and should be made up fresh at 1 mM in DMSO prior to use to prevent light degradation.

Neonatal cardiomyocytes are isolated as described above. The cardiomyocytes are plated in 96-well format (black clear-bottomed plates) at a density of $7.5\times10^4$ per well and grown for 2 days in the presence of 5% FBS prior to use in the assay.

Physiological ischemia is simulated by placing the cardiomyocytes in an anaerobic chamber (0% $O_2$, 85% $N_2$, 5% $CO_2$ & 10% $H_2$) in DMEM containing 1 mM glucose. Positive control cells are treated with DMEM-F12 containing 25 mM Glucose, which protects against the anoxia.

The test compounds are made up in DMEM-1 mM glucose in 96 deep-well mother plates and appropriately diluted for use in the assay. The media is removed from the cells and replaced with 200 μl of either DMEM-F12 or 1 mM DMEM with or without test compounds. The plates are then placed inside a 37° C. incubator in the anaerobic chamber and incubated for 16 hours. The plates are then removed and reoxygenated by the addition of pre-warmed DMEM-F12 containing 5% FBS. Since the anoxic treatment may damage and/or kill the cells, causing them to dislodge from the bottom of the wells gentle aspiration of media is required at this step. The cells are then placed in a normal incubator at 37° C. and incubated for two hours to allow the cells to reoxygenate.

A working solution of 20 μM Fluo-4 is added to pre-warmed 1×HBSS. The cells are loaded with Fluo-4 by first removing media from the cells and replacing with 100 μl of 20 μM Fluo-4. Unloaded control cells are treated in parallel with 1×HBSS alone. All cells are then incubated at 37° C. for 30 minutes. Before fluorescence measurements are made, the cells are washed in indicator-free medium (HBSS) to remove any dye that is non-specifically associated with the cell surface. Cells are then incubated for an additional 20 minutes at room temperature. Basal Fluo-4 fluorescence is measured using the 485 nm excitation and 538 nm emission filter pair on a microplate flourometer (Fluorskan™, Thermo Labsystems Oy, Helsinki, Finland). Each well is read for 60 ms to obtain a baseline reading, then removed from the fluorimeter and stimulated to contract by addition of 1×HBSS (which contains 1.3 mM $CaCl_2$), followed by incubation at 37° C. for 90 minutes. A second fluorescence reading is then taken. Difference in pre vs. post stimulation fluorescence readings is indicative of activity.

Results

When tested as described above, compounds of the present invention, administered at concentrations of about 100 $\mu$M to about 1000 $\mu$M, including:

2-amino-4-[1-(carboxymethyl-carbamoyl)-2-(2-oxo-2-pentyloxycarbonyl-ethylsulfanyl)-ethylcarbamoyl]-butyric acid, 2-amino-4-[1-(carboxymethyl-carbamoyl)-2-(2-ethoxycarbonyl-2-oxo-ethylsulfanyl)-ethylcarbamoyl]-butyric acid, 2-Amino-4-[1-(carboxymethyl-carbamoyl)-2-(2,3-dioxo-3-piperidin-1-yl-propylsulfanyl)-ethylcarbamoyl]-butyric acid, 2-Amino-4-[1-(carboxymethyl-carbamoyl)-2-(3-morpholin4-yl-2,3-dioxo-propylsulfanyl)-ethylcarbamoyl]-butyric acid, 3-(1H-benzoimidazol-2-ylsulfanyl)-2-oxo-propionic acid ethyl ester, 3-(5-chloro-benzothiazol-2-ylsulfanyl)-2-oxo-propionic acid ethyl ester, 3-(5-nitro-benzoimidazol-2-ylsulfanyl)-2-oxo-propionic acid ethyl ester, and 3-(5-methoxy-benzoimidazol-2-ylsulfanyl)-2-oxo-propionic acid ethyl ester, showed the presence of calcium transients in about 25 to about 90% of the cells, with amounts indicative of ability guard against ischemic damage and allow the cells to maintain their contractile function.

Example 40

Rat Middle Cerebral Artery Occlusion (MCAO) Model of Cerebral Ischemia

A. Animal Preparation

Male Wistar rats (Harlan, Ind.) weighing 300–350 g are commonly used in these experiments. Animals are allowed free access to water and commercial rodent diet under standard laboratory conditions. Room temperature is maintained at 20–23° C. and room illumination is on a 12/12-hour light/dark cycle. Animals are acclimatized to the laboratory environment 5 to 7 days prior to the study, and fasted (with free access to water) overnight before surgery.

B. Middle Cerebral Artery Occlusion (MCAO)

Anesthesia is maintained by inhalation of 3.0% isoflurane (Aerrane, Front Dodge, Iowa) in 0.8% oxygen. The animal's neck is shaved and sterilized before operation. Body temperatures are controlled and maintained at 37.5° C.+/−1 degree via external heating and cooling devices. To lower the body temperature, animals are placed in a cooling chamber that uses ice to cool circulating air. Throughout the study the body temperature is recorded using a temperature transponder (BMDS Inc., Seaford, Del.) implanted subcutaneously at the time of MCAO between the rat shoulder blades, which allows the user to read the body temperature via a pocket scanner (BMDS Inc., Seaford, Del.). The body temperature can also be taken by inserting the temperature probe into the animal's rectum. Body temperature is recorded every hour for 6 hours post-occlusion, but temperature is measured more frequently to facilitate maintaining the animals' normothermic temperature.

Animals are subjected to two hours MCAO using a modified intraluminal filament technique, as follows. A midline incision on the ventral part of the neck is made to expose external and internal carotid arteries. The right external and common carotid arteries are ligated by a suture (silk 5/0, Carlisle Laboratories, Farmers Branch, Tex.) and the right internal artery is temporarily ligated using a microvascular clip (Fine Science Tool Inc., Foster City, Calif.). A small incision is made in the common carotid artery. A nylon filament, its tip rounded by heating, is prepared from a fishing line (Stren Fishing Lines, Wilmington, Del.) and is inserted from the right common carotid artery. The filament is advanced into the internal carotid artery 18–20 mm from the point of bifurcation of internal and external arteries and a suture is tightly ligated around the filament. Two hours post occlusion, animals are re-anesthetized to allow reperfusion for the remaining of the experiment by removal of the filament.

C. Drug Administration

Test compounds can be administered by any of a number of routes, such as those described below. Compounds can be administered before, during or after occlusion, as appropriate to the protocol.

a) Intracerebroventricular (ICV) Infusion The anesthetized animal is placed on a stereotaxic apparatus (Harvard Apparatus, S. Natick, Mass.). Anesthesia is maintained by inhalation of 3.0% isoflurane (Aerrane, Front Dodge, Iowa) in 0.8% oxygen throughout the entire procedure. The scalp is shaved and sterilized prior to surgery. A midline sagittal incision about 3 cm long is made slightly behind the eyes to expose the skull. The skull is scraped with a rounded end spatula to remove periosteal connective tissue. A bur hole is placed 1.5 mm lateral, 1 mm posterior to the left of the bregma to mark the left lateral ventricle. A brain infusion cannula (ALZET—Alza, Palo Alto, Calif.) is inserted 4 mm deep into the hole. The desired depth is adjusted by attaching spacers to the cannula. The cannula, attached to a 4-cm silastic catheter (Helix Medical Inc., Carpinteria, Calif.), is fixed in place with dental cement (Ketac-cement, Norristown, Pa.). The catheter is either attached to a primed osmotic pump placed subcutaneously between the shoulder blades for permanent infusion or to a syringe for a short infusion.

b) Intravenous (IV) Osmotic Pump Implantation into the jugular vein

Anesthesia is maintained by inhalation of 3.0% isoflurane (Aerrane, Front Dodge, Iowa) in 0.8% oxygen throughout the entire procedure. The animal's neck is shaved and sterilized before operation. A midline incision is made on the ventral part of the neck to exposes the jugular vein. The vein is isolated and ligated with a suture (silk 5/0, Carlisle Laboratories, Farmers Branch, Tex.) rostral to the point of the incision and a microvascular clip (Fine Science Tool Inc., Foster City, Calif.) is placed close to the heart. A small incision is made between the two ligations. A 2-cm silastic catheter (Helix Medical Inc.) attached to a PE-60 tube (Becton. Dickinson and Co. Sparks, Md.) connected to an ALZET (Alza, Palo Alto, Calif.) pump is introduced and advanced 2 mm into the jugular vein toward the heart. The microvascular clip is removed and the catheter is secured in place with a suture (silk 5/0, Carlisle Laboratories, Farmers Branch, Tex.). The pump is placed into a pocket made subcutaneously between the shoulder blades, allowing the catheter to reach over neck to the jugular vein with sufficient slack to permit free movement of neck and head.

c) IV infusion via femoral vein Anesthesia is maintained by inhalation of 3.0% isoflurane (Aerrane, Front Dodge, Iowa) in 0.8% oxygen throughout the entire procedure. The exterior site of the right femoral vein is shaved and sterilized prior to surgery. A 3-cm incision is made in the right groin region and the femoral vein is isolated. A small incision is made on the femoral vein, temporarily ligated with a microvascular clip, to introduce and advance a polyethylene (PE-50) catheter (Becton Dickinson and Co. Sparks, Md.). The catheter is secured in place with suture (silk 510, Carlisle Laboratories, Farmers Branch, Tex.). The other end of the catheter is attached to a syringe filled with the heparinized saline for the bolus injection. Using a hemostat, a pocket is made subcutaneously on the back of the animal so the PE catheter can be brought up to the exteriorization point at the nape of the neck for either a bolus injection or a continuous injection by an osmotic pump.

d) Intraperitoneal (IP) Injection An awake rat is held in a standard hand hold position, a 23 3/4G needle is injected into the lower right quarter of the abdomen past the peritoneum, slightly off the midline. To avoid organ injection, the plunger of the syringe is slightly pulled back. If no fluid is withdrawn, the content of the syringe is delivered into the abdominal cavity.

e) Gavage feeding A standard rat gavage tube (Popper & Sons Inc., NY) is attached to a 3-cc hypodermic syringe. The animal is held by the shoulder in a vertical position. The feeding tube is placed into the mouth then advanced until it reaches the stomach (the approximate insertion length of the tube was measured prior to the feeding). The content of the syringe is slowly delivered, and then the tube is withdrawn.

D. Behavioral Assessment

One hour after MCAO, the animal is gently held by its tail and observed for forelimb flexion. Then the animal is placed on the floor to be observed for walking pattern; only the animals that score 3 on the Bederson grading system (Table 1) are included in the study.

TABLE 1

Bederson Grading System for Neurological Evaluation

| Neurological deficit | Grading | Behavioral observation |
|---|---|---|
| Normal | grade 0: | No observable deficit |
| Moderate | grade 1: | forelimb flexion |
| Severe | grade 2: | forelimb flexion, decreased resistance to lateral push |
|  | grade 3: | forelimb flexion, decreased resistance to lateral push, circle to paretic side |

E. Evaluation of Ischemic Damage

Twenty-four hours post-MCAO, or longer in some experiments, animals are sacrificed by $CO_2$ asphyxiation (dry ice). The brain is quickly removed from the skull, using standard procedures, rinsed in chilled saline solution, and placed on a rat brain tissue slicer (ASI instrument, MI). Seven 2-mm thick coronal slices are cut from each brain using razor blades. The slices are immersed in 0.9% saline containing 1.0% 2,3,5-triphenyltetrazolume chloride (TTC) (Sigma Chemical Co., St. Louis, Mo.) and incubated in a 37° C. water bath for 30 minutes.

After staining, each 2-mm slice is photographed with a TMC-7 camera (JH Technologies, Ca) which is directly connected to a desktop PC to capture and save the image of each brain slice. This image is used for the measurements of the regions of interest using a computer-based image processing system (Metamorph).

To measure each area, the region of interest is selected using a freehand selection tool, the area is automatically computed by selecting the measure command. The measurements for primary regions of interest are right hemisphere, left hemisphere, total infarct, subcortical infarct, total penumbra and subcortical penumbra. After all regions of interest are measured for all seven slices of the brain, they are sorted by slice number and the corresponding regions of interest using an Excell macro called statistic final. This macro also calculates the cortical penumbra, cortical infarct and total ischemic damage for each slice; the corresponding areas of each rat brain are added together to produce a single measurement for each area. Since the ipsilateral hemisphere is swollen following MCAO, edema volume is calculated and reported as the volumetric differences between the right and left hemispheres of each brain slice. Using the % of hemispheric swelling all the volumes are corrected for the edema.

The volume of the damage is determined using the calculations below for each rat's brain.

| Measurement | Equation | Corrected Value(s) |
|---|---|---|
| Cortical Penumbra (C.P.) | Total Penumbra - Suboortical Penumbra | Total Penumbra (T.P.$_{corr}$) = (T.P. × % H.S./100) <br> C.P.$_{corr}$ = C.P. − (C.P. × % H.S./100) <br> S.P.$_{corr}$ = S.P. − (S.P. × % H.S./100) |
| Cortical Infarct | Total Infarct- Subcortical Infarct | T.I.$_{corr}$ = T.I. − (T.I. × % H.S./100) <br> S.I.$_{corr}$ = S.I.−(S.I. × % H.S./100) <br> C.I.$_{corr}$ = C.I. − (C.I. × % H.S./100) |
| Total Ischemic Damage (T.I.D.) | Total Penumbra + Total Infarct | T.I.D.$_{corrected}$ = T.I.D. − (T.I.D. × % H.S./100) |
| Total Volume (mm$^3$) | Each value is multiplied by 2 (the thickness of the tissue). | |
| Edema Volume | The volumetric differences between the sum of right and left hemispheres determines the edema volume. | |
| % Hemispheric swelling (H.S.) | Edema × 100/left hemisphere | |

F. Statistical Analysis

Sample size is chosen to achieve a 90% probability of significant results. The measurements representing the same region of interest in seven slices of each rat's brain are added together to yield a single measurement for total infarct, subcortical infarct, cortical infarct, total penumbra, subcortical penumbra, cortical penumbra, total ischemic damage and edema in each animal. Group data are presented as means+/−SEM. Differences at the level of $p<0.05$ are considered statistically significant. Between groups, comparisons of each region of interest are carried out by unpaired student t test (between two groups) or one way ANOVA followed by post hoc Bonferroni's multiple comparisons or by the nonparametric Dunnett's test (between control and the drug treated groups).

Results

When tested as described above, compounds of the present invention, including:

2-amino-4-[1-(carboxymethyl-carbamoyl)-2-(2-hexyloxycarbonyl-2-oxo-ethylsulfanyl)-ethylcarbamoyl]-butyric acid, 2-amino-4-[1-(carboxymethyl-carbamoyl)-2-(2-carboxy-2-oxo-ethylsulfanyl)-ethylcarbamoyl]butyric acid, 2-amino-4-[1-(carboxymethyl-carbamoyl)-2-(2-ethoxycarbonyl-2-oxo-ethylsulfanyl)-ethylcarbamoyl] butyric acid, 2-amino-4-[2-(2-butoxycarbonyl-2-methoxyimino-ethylsulfanyl)-1-(carboxymethyl-carbamoyl)-ethylcarbamoyl]-butyric acid or the HCl salt thereof, 2-amino-4-[2-(2-benzyloxyimino-2-butoxycarbonyl-ethylsulfanyl)-1-(carboxymethyl-carbamoyl)-ethylcarbamoyl]-butyric acid or the HCl salt thereof, 2-amino-4-[1-(carboxymethyl-carbamoyl)-2-(2-ethoxycarbonyl-2-hydroxyimino-ethylsulfanyl)-ethylcarbamoyl]-butyric acid, 2-amino-4-[1-(carboxymethyl-carbamoyl)-2-(2-ethoxycarbonyl-2-methoxyimino-ethylsulfanyl)-ethylcarbamoyl]-butyric acid 2-Amino-4-[1-(carboxymethyl-carbamoyl)-2-(2-hydroxyimino-3-oxo-3-piperidin-1-yl-propylsulfanyl)-ethylcarbamoyl]-butyric acid, 2-Amino-4-[1-(carboxymethyl-carbamoyl)-2-(2,3-dioxo-3-piperidin-1-yl-propylsulfanyl)-ethylcarbamoyl]-butyric acid, 2-Amino-4-{1-(carboxymethyl-carbamoyl)-2-[2-(1-methoxycarbonyl-2-phenyl-ethylcarbamoyl)-2-oxo-ethylsulfanyl]-ethylcarbamoyl}-butyric acid, 3-(1H-benzoimidazol-2-ylsulfanyl)-2-oxo-propionic acid ethyl ester, 3-(5-nitro-benzoimidazol-2-ylsulfanyl)-2-oxo-propionic acid ethyl ester, 3-(5-methoxy-benzoimidazol-2-ylsulfanyl)-2-oxo-propionic acid ethyl ester, and 3-(4,5-dihydro-thiazol-2-ylsulfanyl)-2-oxo-propionic acid ethyl ester, provided a reduction in total infarct volume of at least about 20% up to about 80% at doses in the range of less than about 1 µg/kg to less than about 10 mg/kg.

Example 41

Model of Myocardial Infarction: Left Coronary Ligation (Rat)

Male Sprague-Dawley weighing 250–320 g are allowed free access to water and commercial rodent diet under standard laboratory conditions. Room temperature is maintained at 20–23° C. and room illumination is on a 12/12-hour light/dark cycle. Animals are acclimatized to the laboratory environment 5 to 7 days prior to the study and are fasted overnight prior to surgery.

Surgical Procedure for Acute Studies: Rats are anaesthetized with Urethane (1.2–1.5 gm/kg). Core body temperature is maintained at 37° C. by using a heating blanket. The surgical area is shaved, and a ventral midline incision is made to expose the trachea and jugular area. A catheter (PE50) is placed in the jugular for administration of compound and maintenance anesthesia. The trachea is incised and a 14–16-gauge modified intravenous catheter is inserted and tied in place as an endotracheal tube. The animal is placed in right lateral recumbency and initially placed on a Harvard ventilator with a tidal volume of 5–10 ml/kg. 100% $O_2$ is delivered to the animals by the ventilator. ECG electrodes are placed to record a standard Lead II ECG. The surgical site is cleaned with alcohol swab, and a skin incision is made over the rib cage over the $4^{th-5th}$ intercostal space. The underlying muscles are dissected with care to avoid the lateral thoracic vein, to expose the intercostal muscles. The chest cavity is entered through the $4^{th-5th}$ intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. A piece of tubing is placed over the suture to form an occluder. The coronary artery is occluded for 30 minutes by sliding the tube towards the heart until resistance is felt and holding it in place with a vascular clamp. The ECG is monitored for S-T changes indicative of ischemia. After 30 minutes, the occluder is removed, leaving the suture in place. The ECG is monitored for the first 10 minutes of reperfusion. The rat is transferred to the pressure control ventilator for the remainder of the protocol. The rats are ventilated by a small animal ventilator with a peak inspiratory pressure of 10–15 cm $H_2O$ and respiratory rate 60–110 breaths/min. The heart is allowed to reperfuse for 90 minutes.

Surgical procedure for 24 hour study: Rats are anaesthetized with Ketamine/Xylazine IP (95 and 5 mg/kg) and intubated with a 14–16-gauge modified intravenous catheter. Anesthesia level is checked every 15 minutes by toe pinch. Core body temperature is maintained at 37° C. by using a heating blanket. The surgical area is shaved and scrubbed. A ventral midline incision is made to expose the jugular vein. A catheter (PE50) is placed in the jugular for administration of compound and maintenance anesthesia. The animal is placed in right lateral recumbency and initially placed on a ventilator with a tidal volume of 5–10 ml/kg $H_2O$ or a pressure controlled ventilator with a peak inspiratory pressure of 8–15 cm $H_2O$ and respiratory rate 60–110 breaths/min. 100% $O_2$ is delivered to the animals by the ventilator. ECG electrodes are placed to record a standard Lead II ECG. The surgical site is cleaned with surgical scrub and alcohol. A skin incision is made over the rib cage over the $4^{th-5th}$ intercostal space. The underlying muscles are dissected with care to avoid the lateral thoracic vein, to expose the intercostal muscles. The chest cavity is entered through $4^{th-5th}$ intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. A piece of tubing is placed over the suture to form an occluder. The coronary artery is occluded for 30 minutes by sliding the tube towards the heart until resistance is felt and holding it in place with a vascular clamp. The ECG is monitored for S-T changes indicative of ischemia. After 30 minutes, the occluder is removed, leaving the suture in place. The ECG is monitored for the first 10 minutes of reperfusion. The incision is closed in three layers. The IV catheter is removed or tunneled under the skin and exteriorized between the shoulder blades to allow for blood withdrawal or further drug therapy. The rat is ventilated until able to ventilate on its own. The rats are extubated and recovered on a heating pad. Once awake, they are returned to their cage(s). Animals may receive Buprenorphine (0.01–0.05 mg/kg SQ) for post-operative analgesia. After the designated reperfusion time (24 hours) the animals are anesthetized and the hearts removed under deep anesthesia.

Treatment Protocols

Diet Animals are fed a custom diet prior to or after coronary ligation. The length of treatment varies with the study. Doses are calculated based on the average consumption of 15 gms of feed per day for a 300 gm rat. Rat weights are monitored during the study. Feed not consumed is weighed to estimate consumption rates.

Gavage Animals are dosed orally by gavage. Length and frequency of treatment vary with the study. A standard rat gavage tube (Popper & Sons Inc, NY) is attached to a 3-cc hypodermic syringe. The animal is held by the shoulder in a vertical position. The feeding tube is placed into the mouth then advanced until it reaches the stomach (the approximate insertion length of the tube is measured prior to the feeding). The content of the syringe is slowly delivered, and then the tube is withdrawn.

IV Treatment A ventral incision is made to expose the jugular area. A catheter (PE50) is placed in the jugular vein for administration of compound. Animals are dosed by bolus injection and/or continuous infusion. The time and duration of treatment varies with the protocol.

Tissue Processing

After reperfusion, each animal receives 200 units of heparin IV under general anesthesia and the heart is removed and placed in cold saline. After removal the coronary artery is ligated with the suture that is already in place. The heart is placed on a perfusion apparatus and Evans Blue dyed is infused delineate the area at risk. The heart is then cut into five 2-mm thick transverse slices from apex to base. The slices are incubated in 1% triphenyltetrazolium chloride (TTC) in 0.9% saline for 20 minutes at 37° C. Tetrazolium reacts with NADH in the presence of dehydrogenase enzymes causing viable tissue to stain a deep red color and that is easily distinguished from the infarcted pale-unstained necrotic tissue. The slices are placed apex side down in the lid of a small petri dish for the staining procedure. The bottom of the dish is placed over the slices to keep them flat. The slices are photographed in order from apex to base, with the base side up. The areas of infarcted tissue, area at risk and the whole left ventricle are determined using a computerized image analysis system. The total area for each region is added together to give a total for the entire heart. Infarct size is expressed both as a percentage of the total ventricle and the area at risk.

Statistical Analysis

Group data is represented as means +/− SEM. Comparisons between treatment groups are made using ANOVA with p<0.05 considered significant. Post hoc comparisons may be made using either Dunnett's test or Tukey's test.

Results

When tested as described above, compounds of the present invention, including:

2-amino-4-[1-(carboxymethyl-carbamoyl)-2-(2-ethoxycarbonyl-2-oxo-ethylsulfanyl)-ethylcarbamoyl] butyric acid, 2-amino-4-[2-(2-butoxycarbonyl-2-methoxyimino-ethylsulfanyl)-1-(carboxymethyl-carbamoyl)-ethylcarbamoyl]-butyric acid or the HCl salt thereof, 2-amino-4-[2-(2-benzyloxyimino-2-butoxycarbonyl-ethylsulfanyl)-1-(carboxymethyl-carbamoyl)-ethylcarbamoyl]-butyric acid or the HCl salt thereof, 2-amino-4-[1-(carboxymethyl-carbamoyl)-2-(2-ethoxycarbonyl-2-hydroxyimino-ethylsulfanyl)-ethylcarbamoyl]-butyric acid, 2-Amino-4-[1-(carboxymethyl-carbamoyl)-2-(2,3-dioxo-3-piperidin-1-yl-propylsulfanyl)-ethylcarbamoyl]-butyric acid, and 3-(5-chloro-benzothiazol-2-ylsulfanyl)-2-oxo-propionic acid ethyl ester, show activity in the range of about 15% to about 55% infarct size reduction.

Example 42

Evaluations of Sensorimotor Behavior

A. Fore and Hindlimb Grip Strength Test in Rats

Animals with cerebral infarction induced by transient or permanent unilateral occlusion of the middle cerebral artery (MCA) and sham-operated rats are tested for grip strength, a standard model of neuromuscular function and sensorimotor integration, using a Computerized Grip Strength Meter for Rats (Dual Stand Model, Columbus Instruments, Columbus, Ohio).

Animals are moved into the testing room for 30 minutes before testing. Prior to testing, each gauge is calibrated with a set of known weights and the apparatus is adjusted for the size of animal, according to manufacturer's instructions. The forelimb measurements are carried out with the meter in the tension peak mode to freeze the reading as the subject is pulled away from the grip bar. The hindlimb measurements are carried out with the meter in the compression peak mode to freeze the reading as the subject's hindlimbs are pulled over the bar toward the meter. Each animal is hand-held by the investigator as pulled past the grip bars, using a consistent technique, leaving the fore and hind limbs free to grasp the grip bars.

Testing is carried out on postoperative day 2 and repeated, in a blind-randomized fashion, twice weekly for a defined interval. Typically, three successive readings are taken for each animal with an intertrial interval long enough to record the data and zero both meters for the next trail.

B. Rota-Rod Test in Rats

Apparatus: Rota-Rod Treadmill for Rats (7750 Accelerating Model, from UGO BASILE, COMERIO-ITALY).

Procedure: Animals with cerebral infarction induced by transient or permanent unilateral occlusion of the middle cerebral artery (MCA) and sham-operated rats are tested in this study, using a Rota-Rod Treadmill for Rats (7750 Accelerating Model, UGO Basile, Comerio, Italy). The animals are moved into the testing room 30 minutes before testing. Every rat receives 2–3 training runs of 1–2 minutes at intervals of 2–3 hours before testing.

The cylinder on the apparatus is set in motion before placing the rats in position. The motor is set at a constant selected speed in 7700 on RESET mode, and the rats are placed, one by one, in their sections.

Testing is carried out on postoperative day 2 and repeated, in a blind-randomized fashion, twice weekly for a defined interval. Typically, three successive readings are taken for each animal with an intertrial interval long enough to record the data and zero both meters for the next trail.

The compounds of the present invention show activity when tested by this method.

Example 43

Model of Congestive Heart Failure

Experimental Preparation

225–275 g male Sprague-Dawley CD (Charles River) rats are used for this experiment. Animals are allowed free access to water and commercial rodent diet under standard laboratory conditions. Room temperature is maintained at 20–23° C. and room illumination is on a 12/12-hour light/dark cycle. Animals are acclimatized to the laboratory environment 5 to 7 days prior to the study. The animals are fasted overnight prior to surgery.

Animals are anaesthetized with ketamine/xylazine (95 mg/kg and 5 mg/kg) and intubated with a 14–16-gauge modified intravenous catheter. Anesthesia level is checked by toe pinch. Core body temperature is maintained at 37° C. by using a heating blanket. The surgical area is clipped and scrubbed. The animal is placed in right lateral recumbency and initially placed on a ventilator with a peak inspiratory pressure of 10–15 cm $H_2O$ and respiratory rate 60–110 breaths/min. 100% $O_2$ is delivered to the animals by the ventilator. ECG electrodes are placed to record a standard Lead II ECG. The surgical site is scrubbed with surgical scrub and alcohol. An incision is made over rib cage over the $4^{th}$–$5^{th}$ intercostal space. The underlying muscles are dissected with care to avoid the lateral thoracic vein, to expose the intercostal muscles. The chest cavity is entered through $4^{th}$–$5^{th}$ intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. The coronary artery is occluded by tying the suture around the artery. The ECG is monitored for S-T changes indicative of ischemia. If the animal develops ventricular fibrillation, gentle cardiac massage is used to convert the animal to a normal rhythm. The incision is closed in three layers. The rat is ventilated until are able to ventilate on their own. The rats are extubated and recovered on a heating pad. Animals receive buprenorphine (0.01–0.05 mg/kg SQ) for post operative analgesia. Once awake, they are returned to their cage. Animals are monitored daily for signs of infection or distress. Infected or moribund animals are euthanized. Animals are weighed once a week.

Treatment Protocols

Diet Animals are fed a custom diet prior to or after coronary ligation. The length of treatment will vary with the study. Doses are calculated based on the average consumption of feed per day. Rat weights are monitored during the study. Feed not consumed is weighed to estimate consumption rates.

Gavage Animals are dosed orally by gavage. Length and frequency of treatment will vary with the study. A standard rat gavage tube (Popper & Sons Inc, NY) is attached to a 3-cc hypodermic syringe. The animal is held by the shoulder in a vertical position. The feeding tube is placed into the mouth then advanced until it reaches the stomach (the approximate insertion length of the tube is measured prior to the feeding). The content of the syringe is slowly delivered, and then the tube is withdrawn.

Drinking Water Compound can also be dissolved in the drinking water. Water consumption is monitored. In the case of a bitter tasting compound, flavoring agents may be added to the water of both vehicle and treated groups. In the case of insoluble compounds, solubilizing agents may be used (i.e. 0.015% cremophor.0.015% alcohol).

Alzet Pumps Alzet pumps can be implanted using aseptic techniques into the peritoneum or subcutaneously behind the shoulder blades. Pumps are implanted using Isoflurane anesthesia. Serial implantation can be used for extended studies.

Measurements

In vivo After 6–12 weeks the animals are anesthetized with Ketamine/Xylazine (95 mg/kg and 5 mg/kg), and a catheter is placed in the right carotid artery and advanced into the left ventricle for hemodynamic measurements. The catheter is attached to a pressure transducer calibrated against a mercury manometer immediately prior to use. Recordings are made by a DATAQ data analysis system. Pressure traces are recorded and analyzed for heart rate, left ventricular systolic and diastolic pressure, left ventricular developed pressure, and dP/dt max and min. An average of at least five peaks is used to determine values for left ventricular systolic and end diastolic pressure. Left ventricular developed pressure is determined by subtracting end diastolic pressure from left ventricular systolic pressure. Heart rate is determined from the frequency spectrum of a 5 second sample. After measurements are taken, 2 ml blood is removed and placed in serum and plasma tubes for possible analysis.

Ex vivo After removal, the heart is placed in cold saline to stop the beating, then trimmed and weighed. Heart weight is presented as total weight and as a percentage of total body weight. After removal of the heart, lungs and liver are weighed and dried overnight for determination of wet to dry ratios.

The heart is sliced and slice #3 is incubated in 1% triphenyltetrazolium chloride (TTC) in 0.9% saline for 20 minutes at 37° C. Tetrazolium reacts with NADH in the presence of dehydrogenase enzymes causing viable tissue to stain a deep red color that is easily distinguished from the infarcted pale-unstained necrotic tissue. The slice is placed apex side down in the lid of a small petri dish for the staining procedure. The bottom of the dish is placed over the slice to keep it flat. The slice is photographed. The areas of infarcted tissue, left and right ventricle are determined using a computerized image analysis system. Infarct size is expressed as a percentage of the total ventricle. Total areas of the left and right ventricle are measured. The remaining sections are divided into right and left ventricle and frozen for TBARS and glutathione assays.

Statistical Analysis

Group data is presented as means +/− SEM. Comparisons between treatment groups are made using ANOVA with p<0.05 considered significant. Post hoc comparisons use either Dunnett's test or Tukey's test. Survival curves are generated using Graph Pad Prism. For each X value (time) Prism shows the fraction still alive. It also shows standard error. Prism calculates survival fractions using the product limit or Kaplan-Meier method.

The compounds of the present invention, administered in the drinking water in concentrations ranging from 10 mg/L to 1000 mg/L with treatment initiated 1 week following ligation, show activity when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

We claim:

1. The compound selected from:
   3-(5-chloro-benzothiazol-2-ylsulfanyl)-2-hydroxyimino-propionic acid ethyl ester,
   2-hydroxyimino-3-(5-methoxy-1H-benzoimidazol-2-ylsulfanyl)-propionic acid ethyl ester, and
   3-(1H-benzoimidazol-2-ylsulfanyl)-2-hydroxyimino-propionic acid ethyl ester,
or a single tautomer, single stereoisomer, a mixture of tautomers and/or stereoisomers, or a pharmaceutically acceptable salt thereof.

2. A pharmaceutical formulation comprising a compound of claim 1 and a pharmaceutically acceptable excipient.

3. The compound selected from:
   3-(1H-benzoimidazol-2-ylsulfanyl)-2-oxo-propionic acid,
   2-oxo-3-(4-oxo-3,4-dihydro-quinazolin-2-ylsulfanyl)-propionic acid ethyl ester,
   3-(benzoselenazol-2-ylsulfanyl)-2-oxo-propionic acid ethyl ester,
   3-(1H-benzoimidazol-2-ylsulfanyl)-2-oxo-propionic acid ethyl ester, 3-(5-chloro-benzothiazol-2-ylsulfanyl)-2-oxo-propionic acid ethyl ester, 3-(5-methoxy-benzoimidazol-2-ylsulfanyl)-2-oxo-propionic acid ethyl ester, and 3-(4,5-dihydro-thiazol-2-ylsulfanyl)-2-oxo-propionic acid ethyl ester, or a single tautomer, single stercoisomer, a mixture of tautomers and/or stereoisomers, or a pharmaceutically acceptable salt thereof.

4. A pharmaceutical formulation comprising a compound of claim 3 and a pharmaceutically acceptable excipient.

* * * * *

UNITED STATES PATENT AND TRADEMARK OFFICE
CERTIFICATE OF CORRECTION

PATENT NO. : 6,900,218 B2
DATED : May 31, 2005
INVENTOR(S) : Bing Wang, Guy Miller and Satyanarayana Janagani It is certified that error appears in the above-identified patent and that said Letters Patent is hereby corrected as shown below:

<u>Column 86,</u>
Lines 46 and 59, "The compound selected from:" should be -- A compound selected from: --.

Signed and Sealed this

Ninth Day of August, 2005

JON W. DUDAS
*Director of the United States Patent and Trademark Office*